United States Patent
Iwata et al.

(10) Patent No.: US 11,273,155 B2
(45) Date of Patent: Mar. 15, 2022

(54) COMBINATION OF ANTIBODY-DRUG CONJUGATE AND IMMUNE CHECKPOINT INHIBITOR

(71) Applicant: DAIICHI SANKYO COMPANY, LIMITED, Tokyo (JP)

(72) Inventors: Tomomi Iwata, Tokyo (JP); Chiaki Ishii, Tokyo (JP); Teiji Wada, Tokyo (JP); Saori Ishida, Tokyo (JP); Yasuki Kamai, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 209 days.

(21) Appl. No.: 16/467,614

(22) PCT Filed: Dec. 11, 2017

(86) PCT No.: PCT/JP2017/044426
§ 371 (c)(1),
(2) Date: Jun. 7, 2019

(87) PCT Pub. No.: WO2018/110515
PCT Pub. Date: Jun. 21, 2018

(65) Prior Publication Data
US 2019/0314362 A1   Oct. 17, 2019

(30) Foreign Application Priority Data

| Dec. 12, 2016 | (JP) | ............................ JP2016-240442 |
| May 16, 2017 | (JP) | ............................ JP2017-097067 |
| Sep. 25, 2017 | (JP) | ............................ JP2017-183149 |

(51) Int. Cl.
| *A61K 31/4745* | (2006.01) |
| *A61K 47/20* | (2006.01) |
| *A61P 35/00* | (2006.01) |
| *C07K 16/32* | (2006.01) |
| *A61K 47/68* | (2017.01) |
| *A61P 35/02* | (2006.01) |
| *A61K 9/00* | (2006.01) |
| *C07K 16/28* | (2006.01) |

(52) U.S. Cl.
CPC ........ *A61K 31/4745* (2013.01); *A61K 9/0019* (2013.01); *A61K 47/20* (2013.01); *A61K 47/6803* (2017.08); *A61P 35/02* (2018.01); *C07K 16/2818* (2013.01); *C07K 16/32* (2013.01)

(58) Field of Classification Search
CPC ............ A61K 31/4745; A61K 47/6803; A61K 9/0019; A61K 47/20; A61P 35/02; C07K 16/2818; C07K 16/32
USPC .................................................. 424/133.1
See application file for complete search history.

(56) References Cited

U.S. PATENT DOCUMENTS

| 5,480,968 | A | 1/1996 | Kraus et al. |
| 5,677,171 | A | 10/1997 | Hudziak et al. |
| 5,821,337 | A | 10/1998 | Carter et al. |
| 5,834,476 | A | 11/1998 | Terasawa et al. |
| 5,837,673 | A | 11/1998 | Tsujihara et al. |
| 5,892,043 | A | 4/1999 | Tsujihara et al. |
| 5,968,511 | A | 10/1999 | Akita et al. |
| 6,214,345 | B1 | 4/2001 | Firestone et al. |
| 6,291,671 | B1 | 9/2001 | Inoue et al. |
| 6,835,807 | B1 | 12/2004 | Susaki et al. |
| 7,041,818 | B2 | 5/2006 | Susaki et al. |
| 7,449,184 | B2 | 11/2008 | Allison et al. |
| 7,585,491 | B2 | 9/2009 | Govindan |

(Continued)

FOREIGN PATENT DOCUMENTS

| CA | 2927832 A1 | 11/2011 |
| CA | 2815154 A1 | 2/2012 |
| CA | 2859255 A1 | 6/2013 |

(Continued)

OTHER PUBLICATIONS

Acchione et al., Impact of linker and conjugation chemistry on antigen binding, Fc receptor binding and thermal stability of model antibody-drug conjugates, mAbs, 2012, pp. 362-372—(12 pages).
Adams et al., "Humanization of a recombinant monoclonal antibody to produce a therapeutic HER dimerization inhibitor, pertuzumab," Cancer Immunol. Immunother. 55:717-727 (2006).

(Continued)

*Primary Examiner* — Yan Xiao
(74) *Attorney, Agent, or Firm* — Foley & Lardner LLP

(57) ABSTRACT

A pharmaceutical composition and a therapeutic method wherein an antibody-drug conjugate and an immune checkpoint inhibitor are administered in combination, and the antibody-drug conjugate is an antibody-drug conjugate in which a drug-linker represented by the following formula (wherein A represents the connecting position to an antibody) is conjugated to the antibody via a thioether bond; and a pharmaceutical composition and a therapeutic method for use in treatment of a disease that can be ameliorated through an antitumor immunity-activating effect wherein the antibody-drug conjugate is included.

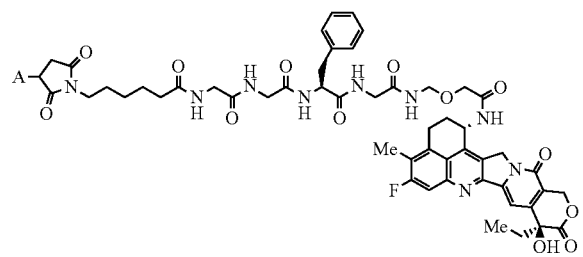

25 Claims, 15 Drawing Sheets
Specification includes a Sequence Listing.

(56) References Cited

U.S. PATENT DOCUMENTS

| | | |
|---|---|---|
| 7,833,979 B2 | 11/2010 | Sullivan et al. |
| 7,837,980 B2 | 11/2010 | Alley et al. |
| 7,999,083 B2 | 8/2011 | Govindan et al. |
| 8,226,945 B2 | 7/2012 | Ebens et al. |
| 8,268,319 B2 | 9/2012 | Govindan |
| 8,425,912 B2 | 4/2013 | Govindan |
| 8,394,607 B2 | 9/2013 | Ebens et al. |
| 8,524,865 B2 | 9/2013 | Ebens et al. |
| 8,741,291 B2 | 6/2014 | Bhat et al. |
| 8,802,820 B2 | 8/2014 | Chamberlain et al. |
| 8,907,071 B2 | 12/2014 | Sullivan et al. |
| 8,968,741 B2 | 3/2015 | Ebens et al. |
| 9,808,537 B2 | 11/2017 | Masuda et al. |
| 9,850,312 B2 | 12/2017 | Agatsuma et al. |
| 9,872,924 B2 | 1/2018 | Naito et al. |
| 10,195,288 B2 | 2/2019 | Masuda et al. |
| 10,227,417 B2 | 3/2019 | Agatsuma et al. |
| 10,383,878 B2 | 8/2019 | Hettmann et al. |
| 2003/0148931 A1 | 8/2003 | Takahashi et al. |
| 2003/0166513 A1 | 9/2003 | Imura et al. |
| 2004/0185053 A1 | 9/2004 | Govindan |
| 2005/0123536 A1 | 6/2005 | Law et al. |
| 2005/0228007 A1 | 10/2005 | Jagtap et al. |
| 2005/0271671 A1 | 12/2005 | Griffiths |
| 2005/0276812 A1 | 12/2005 | Ebens, Jr. et al. |
| 2006/0018899 A1 | 1/2006 | Kao et al. |
| 2006/0193865 A1 | 8/2006 | Govindan |
| 2007/0071764 A1 | 3/2007 | Sullivan et al. |
| 2008/0050310 A1 | 2/2008 | Ebens et al. |
| 2008/0131363 A1 | 6/2008 | Govindan et al. |
| 2008/0161245 A1 | 7/2008 | Kratz et al. |
| 2008/0305044 A1 | 12/2008 | McDonagh et al. |
| 2009/0274713 A1 | 11/2009 | Chari et al. |
| 2009/0286258 A1 | 11/2009 | Kaur et al. |
| 2009/0291093 A1 | 11/2009 | Govindan |
| 2010/0068181 A1 | 3/2010 | Paliwal et al. |
| 2010/0120816 A1 | 5/2010 | Fontana et al. |
| 2011/0045587 A1 | 2/2011 | Sullivan et al. |
| 2011/0059076 A1 | 3/2011 | Mcdonagh et al. |
| 2011/0070248 A1 | 3/2011 | Ichikawa et al. |
| 2011/0229406 A1 | 9/2011 | Hettmann et al. |
| 2011/0293513 A1 | 12/2011 | Govindan et al. |
| 2012/0121615 A1 | 5/2012 | Flygare et al. |
| 2012/0171201 A1 | 7/2012 | Sapra |
| 2012/0201809 A1 | 8/2012 | Bhat et al. |
| 2012/0328634 A1 | 12/2012 | Govindan |
| 2013/0089872 A1 | 4/2013 | Nakamura et al. |
| 2013/0123178 A1 | 5/2013 | Dimarchi et al. |
| 2013/0216561 A1 | 8/2013 | Govindan |
| 2014/0004078 A1 | 1/2014 | Govindan |
| 2015/0297748 A1 | 10/2015 | Masuda et al. |
| 2015/0352224 A1 | 12/2015 | Naito et al. |
| 2016/0279259 A1 | 9/2016 | Masuda et al. |
| 2016/0287722 A1 | 10/2016 | Govindan |
| 2016/0297890 A1 | 10/2016 | Agatsuma et al. |
| 2016/0333112 A1* | 11/2016 | Naito .............. A61K 47/6803 |
| 2017/0021031 A1 | 1/2017 | Hettmann et al. |
| 2019/0151328 A1 | 5/2019 | Hettmann et al. |

FOREIGN PATENT DOCUMENTS

| | | |
|---|---|---|
| CN | 1227499 A | 9/1999 |
| CN | 1764478 A | 4/2006 |
| CN | 101023100 A | 8/2007 |
| CN | 102481364 A | 5/2012 |
| EP | 0 495 432 A1 | 7/1992 |
| EP | 0 737 686 A1 | 10/1996 |
| EP | 0 916 348 A1 | 5/1999 |
| EP | 1 155 702 A1 | 11/2001 |
| EP | 2 594 589 A1 | 5/2013 |
| EP | 2 799 452 A1 | 11/2014 |
| EP | 2 907 824 A1 | 8/2015 |
| EP | 2 910 573 A1 | 8/2015 |
| JP | H05-059061 A | 3/1993 |
| JP | 06-087746 A | 3/1994 |
| JP | H08-337584 A | 12/1996 |
| JP | H10-095802 A | 4/1998 |
| JP | H11-071280 A | 3/1999 |
| JP | H11-092405 A | 4/1999 |
| JP | 2002-060351 A | 2/2002 |
| JP | 2005-511627 A | 4/2005 |
| JP | 2006-511526 A | 4/2006 |
| JP | 2007-527872 A | 10/2007 |
| JP | 2008-521828 A | 6/2008 |
| JP | 2009-538629 A | 11/2009 |
| JP | 2010-513524 A | 4/2010 |
| JP | 2011-519864 A | 7/2011 |
| JP | 2011-524001 A | 8/2011 |
| JP | 2012-509259 A | 4/2012 |
| JP | 2012-100671 A | 5/2012 |
| JP | 2013-534535 A | 9/2012 |
| JP | 2013-500253 A | 1/2013 |
| JP | 2013-534906 A | 9/2013 |
| JP | 2017-503784 A | 2/2017 |
| KR | 1020010052385 A | 6/2001 |
| KR | 1020110044808 A | 4/2011 |
| RU | 2404810 C2 | 7/2008 |
| RU | 2450008 C2 | 5/2012 |
| TW | I232930 | 5/2005 |
| TW | 200817434 A | 4/2008 |
| WO | WO-97/46260 A1 | 12/1997 |
| WO | WO-00/25825 A1 | 5/2000 |
| WO | WO-00/37504 A2 | 6/2000 |
| WO | WO-01/00244 A2 | 1/2001 |
| WO | WO-01/14424 A2 | 3/2001 |
| WO | WO-02/00734 A1 | 1/2002 |
| WO | WO-03/013602 A1 | 2/2003 |
| WO | WO-03/015826 A1 | 2/2003 |
| WO | WO-03/043583 A2 | 5/2003 |
| WO | WO-03/074566 A2 | 9/2003 |
| WO | WO-2005/112919 A2 | 12/2005 |
| WO | WO-2006/065533 A2 | 6/2006 |
| WO | WO-2006/092230 A2 | 9/2006 |
| WO | WO-2006/121168 A1 | 11/2006 |
| WO | WO-2007/077028 A2 | 7/2007 |
| WO | WO-2008/100624 A2 | 8/2008 |
| WO | WO-2008/116219 A2 | 9/2008 |
| WO | WO-2008/144891 A1 | 12/2008 |
| WO | WO-2008/156712 A1 | 12/2008 |
| WO | WO-2010/077634 A1 | 7/2010 |
| WO | WO-2011/011474 A1 | 1/2011 |
| WO | WO-2011/021397 A1 | 2/2011 |
| WO | WO-2011/066389 A1 | 6/2011 |
| WO | WO-2011/068845 A1 | 6/2011 |
| WO | WO-2011/145744 A1 | 11/2011 |
| WO | WO-2011/155579 A1 | 12/2011 |
| WO | WO-2012/019024 A2 | 2/2012 |
| WO | WO-2012/064733 A2 | 5/2012 |
| WO | WO-2013/068946 A2 | 5/2013 |
| WO | WO-2013/077458 A1 | 5/2013 |
| WO | WO-2013/079174 A1 | 6/2013 |
| WO | WO-2013/163229 A1 | 10/2013 |
| WO | WO-2013/188740 A1 | 12/2013 |
| WO | WO-2014/057687 A1 | 4/2014 |
| WO | WO-2014/061277 A1 | 4/2014 |
| WO | WO-2014/107024 A1 | 7/2014 |
| WO | WO-2015/098099 A1 | 7/2015 |
| WO | WO-2015/115091 A1 | 8/2015 |
| WO | WO-2015/155976 A1 | 10/2015 |
| WO | WO-2015/146132 A1 | 10/2015 |
| WO | WO-2015/155998 A1 | 10/2015 |

OTHER PUBLICATIONS

Alimandi et al., "Cooperative signaling of ErbB3 and ErbB2 in neoplastic transformation and human mammary carcinomas," Oncogene 10:1813-1821 (1995)—9 Pages.

Allowance dated Jul. 4, 2017, in Japanese Patent Application No. 2016-117096.

Allowance issued in connection with Taiwanese Patent Application No. 104103127, dated Apr. 11, 2018.

(56) References Cited

OTHER PUBLICATIONS

Australian Intellectual Property Office, "Examination Report No. 2 for Standard Patent Application," Australian Patent Application No. 2014371934, dated Sep. 13, 2019.
Barginear et al., "Trastuzumab-DM1: A Review of the Novel Immuno-Conjugate for HER2-Overexpressing Breast Cancer," The Open Breast Cancer Journal 1:25-30 (2009).
Barok et al., Trastuzumab-DM1 is highly effective in preclinical models of HER2-positive gastric cancer, Cancer Letters, 2011, vol. 306, No. 2, pp. 172-179 (9 pages).
Baselga et al., "Phase II Study of Weekly Intravenous Recombinant Humanized Anti-p185HER2 Monoclonal Antibody in Patients with HER2/neu-Overexpressing Metastatic Breast Cancer," J. Clin. Oncol. 14(3)737-744 (Mar. 1996).
Basu et al., "The Epithelial/Carcinoma Antigen EGP-1 Recognized by Monoclonal Antibody RS7-3G11, is Phosphorylated on Serine 303," Int. J. Cancer 62(4):472-479 (1995).
Beck, Alain, "The Next Generation of Antibody-drug Conjugates Comes of Age," Discovery Medicine 10(53):329-339 (Oct. 16, 2010)—8 Pages.
Behrens et al., Methods for site-specific drug conjugation to antibodies, mAbs, 2014, vol. 6, No. 1, pp. 46-53.
Blok et al., "Cytoplasmic Overexpression of HER2: a Key Factor in Colorectal Cancer", Clinical Insights: Oncology, vol. 7, 2013 pp. 41-51.
Burke,Patrick J et al. Design, Synthesis, and Biological Evaluation of Antibody- Drug Conjugates Comprised of Potent Campothetchin Analogues , Bioconjugate Chemistry, Jun. 17, 2009. Vol.20 No.6 pp. 1242-1250.
Calabrese et al., "Assignment of TACSTD1 (alias TROP1, M4S1)to human chromosome 2p21 and refinement of mapping of TACSTD2 (alias TROP2, M1S1) to human chromosome 1p32 by in situ hybridization," Cytogenet Cell Genet. 92(1-2):164-165 (2001).
Canadian Examiner's Interview Summary issued in Canadian Patent Application No. 2885800 issued on Mar. 28, 2017.
Canadian Office Action dated Apr. 13, 2018 in corresponding application No. 2939802.
Chinese Office Action dated Nov. 1, 2016 in corresponding application No. 201380053256.2.
Chinese Office Action dated Nov. 8, 2019 for corresponding Application No. 201580019138.9—4 pages.
Chinese Office Action issued to corresponding App. No. 201480071134.0—dated Aug. 20, 2019 (5 pages).
Chinese Search Report dated Jun. 24, 2020 for corresponding Application No. 108114649.
Colombian Reconsideration Petition dated Mar. 15, 2018 in corresponding application No. NC2016/0000187—36 pages.
Coussens et al., "Tyrosine Kinase Receptor with Extensive Homology to EGF Receptor Shares Chromosomal Location with neu Oncogene," Science 230(4730):1132-1139 (Dec. 1985).
D. Loo et al: "Development of an Fc-Enhanced Anti-B7-H3 Monoclonal Antibody with Potent Antitumor Activity", Clinical Cancer Research, vol. 18, No. 14, Jul. 15, 2012 (Jul. 15, 2012), pp. 3834-3845, XP055092714, ISSN: 1078-0432, DOI: 10.1158/1078-0432.CCR-12-0715.
De Jager et al., "DX-8951f: Summary of Phase I Clinical Trials," Ann. N.Y. Acad. Sci. 922:260-273 (2000)—16 Pages.
Defazio et al., "Expression of c-erbB Receptors, Heregulin and Oestrogen Receptor in Human Breast Cell Lines," Int. J. Cancer 87:487-498 (2000)—12 Pages.
Di Fiore et al., "erbB-2 Is a Potent Oncogene When Overexpressed in NIH/3T3 Cells," Science 237:178-182 (Jul. 1987).
Dosio et al., "Antibody-targeted leucinostatin A", Journal of Controlled Release, No. 32, (1994), pp. 37-44.
El Sewedy et al., "Cloning of the Murine Trop2 Gene: Conservation of a PIP2-Binding Sequence in the Cytoplasmic Domain of Trop-2," Int. J. Cancer 75(2):324-330 (1998).
English-language translation of International Search Report issued in International Patent Application No. PCT/JP2015/002020 dated Jul. 20, 2015—4 Pages.

Esteva et al., A Phase II Study of Intravenous Exatecan Mesylate (DX-8951f) Administered Daily for 5 Days Every 3 Weeks to Patients with Metastatic Breast Carcinoma, American Cancer Society, 2003, 900-907.
European Search Report issued in corresponding application No. 15743738.5 dated Aug. 9, 2017.
Extended European Search Report dated Feb. 4, 2020 for corresponding Application No. 19206764.3.
Extended European Search Report dated May 10, 2017 in European Patent Application No. 14874745.4.
Extended European Search Report dated May 13, 2016, in European Patent Application No. 13847461.4.
Extended European Search Report dated May 6, 2016, in European Patent Application No. 13845596.9.
Extended European Search Report issued in European Patent Application No. 15776810.2 dated Aug. 11, 2017.
Faulk et al., "Antigens of human trophoblasts: A working hypothesis for their role in normal and abnormal pregnancies," Proc. Natl. Acad. Sci. USA 75(4):1947-1951 (1978).
Fendly et al., "Characterization of Murine Monoclonal Antibodies Reactive to Either the Human Epidermal Growth Factor Receptor or HER2/neu Gene Product," Cancer Research 50:1550-1558 (1990).
Final Office Action issued in U.S. Appl. No. 15/221,851 dated Nov. 13, 2017.
Fong et al., "High expression of TROP2 correlates with poor prognosis in pancreatic cancer," Br. J. Cancer 99(8):1290-1295 (2008).
Fong et al., "TROP2: a novel prognostic marker in squamous cell carcinoma of the oral cavity," Mod. Pathol. 21(2):186-191 (2008).
Fornaro et al., "Cloning of the Gene Encoding Trop-2, a Cell-Surface Glycoprotein Expressed by Human Carcinomas," Int. J. Cancer 62(5):610-618 (1995).
Fukushige et al., "Localization of a Novel v-erbB-Related Gene, c-erbB-2, on Human Chromosome 17 and Its Amplification in a Gastric Cancer Cell Line," Mol. Cell. Biol. 6(3):955-958 (1986).
Gomez-Monterrey et al., "Design, Synthesis, and Cytotoxic Evaluation of Acyl Derivatives of 3-Aminonaphtho[2,3-b]thiophene-4,9-dione, a Quinone-Based System," Journal of Medicinal Chemistry, 2011, 54(12):4077-4091, abstract.
Graus-Porta et al., "ERbB-2, the preferred heterodimerization partner of all ErbB receptors, is a mediator of lateral signaling," EMBO J. 16(7):1647-1655 (1997).
Gravalos et al., "HER2 in gastric cancer: a new prognostic factor and a novel therapeutic target," Ann. Oncol. 19:1523-1529 (2008).
Hardwick et al., "Immunohistochemical detection of p53 and c-erbB-2 in oesophageal carcinoma; no correlation with prognosis," Eur. J. Surg. Oncol. 23:30-35 (1997).
Hudis, M.D., Clifford A., "Trastuzumab—Mechanism of Action and Use in Clinical Practice," N. Engl. J. Med. 357(1):39-51 (2007).
Hudziak et al., "Increased expression of the putative growth factor receptor p185HER2 causes transformation and tumorigenesis of NIH 3T3 cells," Proc. Natl. Acad. Sci. USA 84:7159-7163 (1987).
I. Sullivan, et al."Osimertinib in the treatment of patients with epidermal growth factor receptor T790M mutation-positive metastatic non-small cell lung cancer: clinical trial evidence and experience", Therapeutic Advances in Respiratory Disease, vol. 10(6), pp. 549-565, 2016 (17 pages).
IN Office Action issued in the corresponding Indian Patent Application Ser. No. 201647013640, dated Jul. 19, 2019.
Inoue et al., "CM-Dextran-Polyalcohol-Camptothecin Conjugate: DE-310 with A Novel Carrier System and Its Preclinical Data," Polymer Drugs in the Clinical Stage, 145-153 (2003)—9 Pages.
International Search Report and Written Opinion for correspondence Application No. PCT/JP2018/007152 dated Apr. 24, 2018.
International Search Report for corresponding Application No. PCT/JP2014/006421 dated Mar. 17, 2015.
International Search Report for PCT/JP2013/006069, dated Dec. 17, 2013.
International Search Report for PCT/JP2013/006178, dated Dec. 17, 2013.
International Search Report issued in International Patent Application No. PCT/JP2015/000355 dated Apr. 21, 2015.

(56) References Cited

OTHER PUBLICATIONS

Japanese Notice Of Allowance dated Oct. 18, 2016 in corresponding application No. 2016-166850.
Japanese Office Action dated Dec. 6, 2016 in corresponding application No. 2016-540705.
Joto et al., "DX-8951F, A Water-Soluble Camptothecin Analog, Exhibits Potent Antitumor Activity Against a Human Lung Cancer Cell Line and its SN-38-Resistant Variant," Int. J. Cancer 72:680-686 (1997)—7 Pages.
K. Yonesaka, et al., "Anti-HER3 monoclonal antibody patritumab sensitizes refractory non-small cell lung cancer to the epidermal growth factor receptor inhibitor erlotinib",Oncogene vol. 35, pp. 878-886, 2016 (10 pages.
Kang et al., Engineering multivalent antibodies to target heregulin-induced HER3 signaling in breast cancer cells, mAbs, 2013, vol. 64, No. 1, pp. 15-29.
Kaptain et al., "Her-2/neu and Breast Cancer," Diagn. Mol. Pathol. 10(3):139-152 (2001).
Karunagaran et al., "ErbB-2 is a common auxiliary subunit of NDF and EGF receptors: implications for breast cancer," EMBO J. 15(2):254-264 (1996).
Kawakami et al.—"The anti-HER3 antibody patritumab abrogates cetuximab resistance mediated by heregulin in colorectal cancer cells", Oncotarget, vol. 5, No. 23, Dec. 5, 2014, 11847-11856—10 pages.
Kimio Yonesaka, "Anti-HER3 Antibody Patritumab Overcomes Resistance to EGFR Inhibitor in Non-small Cell Lung Cancer", The Japan Lung Cancer Society, vol. 55, pp. 948-955, 2015 (8 pages).
Korean Office Action dated May 1, 2018 in corresponding application No. 10-2016-7015961.
Korkaya et al., "HER2 regulates the mammary stem/progenitor cell population driving tumorigenesis and invasion," Oncogene 27:6120-6130 (2008).
Kraus et al., "Demonstration of ligand-dependent signaling by the erbB-3 tyrosine kinase and its constitutive activation in human breast tumor cells," Proc. Natl. Acad. Sci. USA 90:2900-2904 (Apr. 1993)—5 Pages.
Kraus et al., "Isolation and characterization of ERBB3, a third member of the ERBB/epidermal growth factor receptor family: Evidence for overexpression in a subset of human mammary tumors," Proc. Natl. Acad. Sci. USA 86:9193-9197 (Dec. 1989)—5 pages.
Kumazawa et al., "Antitumor activity of DX-8951f: a new camptothecin derivative," Exp. Opin. Invest. Drugs 7(4):625-632 (1998)—8 Pages.
Kumazawa et al., "DE-310, a novel macromolecular carrier system for the camptothecin analog DX-8951f: Potent antitumor activities in various murine tumor models," Cancer Sci. 95(2):168-175 (Feb. 2004)—8 Pages.
Kumazawa et al., "Potent and broad antitumor effects of DX-8951f, a water-soluble camptothecin derivative, against various human tumors xenografted in nude mice," Cancer Chemother. Pharmacol. 42:210-220 (1998)—11 Pages.
Linnenbach et al., "Sequence investigation of the major gastrointestinal tumor-associated antigen gene family, GA733," Proc. Natl. Acad. Sci. 86(1):27-31 (Jan. 1989).
Lipinski et al., "Human trophoblast cell-surface antigens defined by monoclonal antibodies," Proc. Natl. Acad. Sci. 78(8):5147-5150 (Aug. 1981).
McDonagh et al., "Engineered antibody-drug conjugates with defined sites and stoichiometries of drug attachment," Protein Engineering, Design & Selection, 2006, 19(7):299-307.
Mitsui et al., "A New Water-soluble Camptothecin Derivative, DX-8951f, Exhibits Potent Antitumor Activity against Human Tumors in vitro and in vivo," Jpn. J. Cancer Res. 86:776-782 (Aug. 1995)—7 Pages.
Moghaddas et al., "Whether HER2-positive non-breast cancers are candidates for treatment with Ado-trastuzumab emtansine?", J. Res Parm Pract, vol. 5(4), 2016 pp. 227-233.
Mühlmann et al., "TROP2 expression as prognostic marker for gastric carcinoma," J. Clin. Pathol. 62(2):152-158 (2009).

N. Masubuchi, "Pharmacokinetics of DE-310, a novel macromolecular carrier system for the camptothecin analog DX-8951f, in tumor-bearing mice," Pharmazie 59: 374-377 (2004).
N.V. Sergina, et al. "Escape from HER-family tyrosine kinase inhibitor therapy by the kinase-inactive HER3", Nature, vol. 445, pp. 437-441, 2007 (6 pages).
Naidu et al., "Expression of c-erbB3 protein in primary breast carcinomas," British Journal of Cancer 78(10): 1385-1390 (1998)—6 Pages.
Nakada et al., "Novel antibody drug conjugates containing exatecan derivative-based cytotoxic payloads," Bioorganic & Medical Chemistry Letters 26(6):1542-1545 (2016)—4 Pages.
Ning et al., "TROP2 expression and its correlation with tumor proliferation and angiogenesis in human gliomas," Neurol. Sci. 34(10):1745-1750 (2013).
Non-Final Office Action dated Apr. 5, 2019 for corresponding U.S. Appl. No. 15/821,697.
Non-Final Office Action issued in U.S. Appl. No. 14/435,114 dated Jul. 21, 2016.
Non-Final Office Action issued in U.S. Appl. No. 14/436,458 dated Jul. 19, 2016.
Non-Final Office Action issued in U.S. Appl. No. 15/180,203 dated Jul. 25, 2016.
Non-Final Office Action issued in U.S. Appl. No. 15/221,851 dated Jul. 7, 2017.
Non-Final Office Action issued in U.S. Appl. No. 15/821,662 dated Jan. 17, 2018.
Notice of Allowance dated Aug. 25, 2017 for corresponding U.S. Appl. No. 15/187,179.
Notice of Allowance dated May 18, 2017 for corresponding U.S. Appl. No. 15/187,179.
Notice of Allowance dated Nov. 2, 2018 for corresponding U.S. Appl. No. 15/821,662.
Notice of Allowance issued in U.S. Appl. No. 15/221,851 dated Jun. 13, 2018.
Ochi et al., "A possible mechanism for the long-lasting antitumor effect of the macromolecular conjugate DE-310: mediation by cellular uptake and drug release of its active camptothecin analog DX-8951," Cancer Chemotherapy and Pharmacology 55(4): 323-332 (2004).
Office Action dated Nov. 21, 2017 in corresponding application No. PCT/JP2017/036215.
Office Action dated Apr. 22, 2016, in Singapore Patent Application No. 11201502887W.
Office Action issued in Colombian Application No. NC2016/0000187 dated May 9, 2017. An English translation is provided.
Office Action issued in U.S. Appl. No. 15/187,179 dated Oct. 21, 2016.
Office Action with Search Report dated Aug. 29, 2017, in RU 2015113767.
Ogitani et al., "Wide application of a novel topoisomerase I inhibitor-based drug conjugation technology," Bioorganic & Medicinal Chemistry Letters, vol. 26, 2016, 5069-5072.
Oguma et al., Validation study of a method for assaying DE-310, a macromolecular carrier conjugate containing an anti-tumor camptothecin derivative, and the free drug in tumor tissue by high performance liquid chromatography/atmospheric pressure chemical ionization tandem mass spectrometry, Biomedical Chromatography, 2005, vol. 19, No. 1, pp. 19-26—(8 pages).
Ohmachi et al., "Clinical Significance of TROP2 Expression in Colorectal Cancer," Clin. Cancer Res. 12(10):3057-3063 (May 15, 2006).
Opposition dated May 3, 2017, against corresponding Colombian Patent Application No. NC2016/0000187.
Otto Soepenberg, "Liquid chromatographic assays for DE-310, a novel camptothecin analog, and two major enzymatic products in human matrices," Journal of Chromatography B, 799, 15-22 (2004).
P. Janne, et al., "Phase 1 study of the Anti-HER3 Antibody Drug Conjugate U3-1402 in Metastic or Unresectable EGFR-mutant NSCLC.", Journal of Thoracic Oncology, vol. 12, No. 11, Supp. Supplement 2, pp. S2290, abstract No. P3.04-013, Nov. 2017 (3 pages).

(56) References Cited

OTHER PUBLICATIONS

Plowman et al., "Molecular cloning and expression of an additional epidermal growth factor receptor-related gene," Proc. Natl. Acad. Sci. USA 87:4905-4909 (Jul. 1990)—5 Pages.
Ripani et al., "Human Trop-2 is a Tumor-Associated Calcium Signal Transducer," Int. J. Cancer 76(5):671-676 (1998).
Rowinsky, Preclinical and Clinical Development of Exatecan(DX-8951f), Camptothecins in Cancer Therapy, 2005, pp. 317-318 (25 pages).
Russian Office Action dated Mar. 5, 2019 in corresponding application No. 2016143351.
Russian Office Action dated Oct. 11, 2018 in corresponding application No. 2016123597—13 pages.
Shen et al., Conjugation site modulates the in vivo stability and therapeutic activity of antibody-drug conjugates, Nature Biotechnology, 2012, vol. 30, pp. 184-189.
Shiose et al., "Systematic Research of Peptide Spacers Controlling Drug Release from Macromolecular Prodrug System, Carboxymethyldextran Polyalcohol-Peptide-Drug Conjugates," Bioconjugate Chem. 20(1):60-70(2009).
Shiose et al., "Relationship between Drug Release of DE-310, Macromolecular Prodrug of DX-8951f, and Cathepsins Activity in Several Tumors," Biol. Pharm. Bull., 2007, 30(12):2365-2370.
Sievers et al., Antibody-Drug Conjugates in Cancer Therapy, Annual Review of Medicine, 2013, vol. 64, No. 1, pp. 15-29.
Slamon et al., "Human Breast Cancer: Correlation of Relapse and Survival with Amplification of the HER-2/neu Oncogene," Science 235:177-182 (1987).
Slamon et al., "Studies of the HER-2/neu Proto-oncogene in Human Breast and Ovarian Cancer," Science 244:707-712 (1989).
Sliwkowski et al., "Coexpression of erbB2 and erbB3 Proteins Reconstitutes a High Affinity Receptor for Heregulin." J. Biol. Chem. 269(20):14661-14665 (1994).
Sliwkowski et al., "Nonclinical Studies Addressing the Mechanism of Action of Trastuzumab (Herceptin)," Semin. Oncol. 26(4) Suppl. 12: 60-70 (Aug. 1999).
Soepenberg et al., "Phase I and Pharmacokinetic Study of DE-310 in Patients with Advanced Solid Tumors," Clin. Cancer Res. 11:703-711 (Jan. 15, 2005)—9 Pages.
Stepan et al., "Expression of Trop2 Cell Surface Glycoprotein in Normal and Tumor Tissues: Potential Implications as a Cancer Therapeutic Target," Journal of Histochemistry & Cytochemistry vol. 59, No. 7, pp. 701-710.
Taiwanese Office Action dated Jul. 30, 2018 in corresponding application No. 104111534.
Taiwanese Office Action issued in Taiwanese Patent Application No. 102136742 dated May 15, 2017.
Takiguchi et al., "Antitumor Effect of DX-8951, a Novel Camptothecin Analog, on Human Pancreatic Tumor Cells and Their CPT-11-resistant Variants Cultured in vitro and Xeografted in Nude Mice," Jpn. J. Cancer Res. 88:760-769 (Aug. 1997)—10 Pages.
Thomas M. Cardillo, "Humanized Anti-Trop-2 IgG-SN-38 Conjugate for Effective Treatment of Diverse Epithelial Cancers: Preclinical Studies in Human Cancer Xenograft Models and Monkeys," Clinical Cancer Research 17(10): 3157-3169 (2011).
Vogel et al., "Efficacy and Safety of Trastuzumab as a Single Agent in First-Line Treatment of HER2-Overexpressing Metastatic Breast Cancer," J. Clin. Oncol. 20(3):719-726 (Feb. 2002).
Wang et al., "Identification of Trop-2 as an oncogene and an attractive therapeutic target in colon cancers," Mol. Cancer Ther. 7(2):280-285 (Feb. 2008).
Wente et al., "DE-310, a macromolecular prodrug of the topoisomerase-I-inhibitor exatecan (DX-8951), in patients with operable solid tumors," Investigational New Drugs 23:339-347 (2005)—9 Pages.
Yano et al., "Comparison of HER2 gene amplification assessed by fluorescence in situ hybridization and HER2 protein expression assessed by immunohistochemistry in gastric cancer," Oncol. Rep. 15:65-71 (2006).
Extended European Search Report dated May 13, 2020 for corresponding European Patent Application No. 17882216.9.

Colino et al: "Two Distinct Mechanisms For Induction of Dendritic Cell Apoptosis in Response to Intact *Streptococcus pneumoniae*", The Journal of Immunology, vol. 171, No. 5, Aug. 19, 2003, pp. 2354-2365.
J. Hu et al: "The effects of chemotherapeutic drugs on human monocyte-derived dendritic cell differentiation and antigen presentation: The effect of chemotherapy drugs on immunotherapy", Clinical and Experimental Immunology, vol. 172, No. 3, Apr. 18, 2013, pp. 490-499.
Trivedi et al: "Tumor Antigen-Specific Monoclonal Antibodies and Induction of T-Cell Immunity", Seminars in Oncology, vol. 41, No. 5, Oct. 1, 2014, pp. 678-684.
Alley et al., "Antibody-drug conjugates: targeted drug delivery for cancer," Current Opinion in Chemical Biology, vol. 14, 2010, pp. 529-537.
Burris, III et al., "Phase II Study of the Antibody Drug Conjugate Trastuzumab-DM1 for the Treatment of Human Epidermal Growth Factor Receptor 2 (HER2)—Positive Breast Cancer After Prior HER2-Directed Therapy," Journal of Clinical Oncology, vol. 29, No. 4, Feb. 1, 2011, pp. 398-405.
Damle, Nitin K., "Tumour-targeted chemotherapy with immunoconjugates of calicheamicin," Expert Opin. Biol. Ther., vol. 4, No. 9, 2004, pp. 1445-1452.
Ducry et al., "Antibody—Drug Conjugates: Linking Cytotoxic Payloads to Monoclonal Antibodies," Bioconjugate Chem, vol. 21, 2010, pp. 5-13.
Abstract of: Iwata et al., "DS-8201a, a HER2-targeting antibody-drug conjugate, to elicit immune responses and benefits in combination with an anti-PD-1 antibody," Journal of Clinical Oncology, vol. 35, No. 15, suppl, May 2017, Abstract No. 1031. <URL: https://ascopubs.org/doi/abs/10.1200/JCO.2017.35.15_suppl.1031>.
John et al., "Anti-PD-1 Antibody Therapy Potently Enhances the Eradication of Established Tumors By Gene-Modified T Cells," Clinical Cancer Research, vol. 19, No. 20, Oct. 15, 2013, pp. 5636-5646.
Menon et al., "Advances in Cancer Immunotherapy in Solid Tumors," Cancers, vol. 8, No. 12, 106, 2016.
Muller et al., "Trastuzumab emtansine (T-DM1) renders HER2+ breast cancer highly susceptible to CTLA-4/PD-1 blockade," Science Translational Medicine, vol. 7, Issue 315, 315ra188, Nov. 2015.
Ogitani et al., "Bystander killing effect of DS-8201a, a novel anti-human epidermal growth factor receptor 2 antibody-drug conjugate, in tumors with human epidermal growth factor receptor 2 heterogeneity," Cancer Science, vol. 107, 2016, pp. 1039-1046.
Ogitani et al., "DS-8201a, A Novel HER2-Targeting ADC with a Novel DNA Topoisomerase I Inhibitor, Demonstrates a Promising Antitumor Efficacy with Differentiation from T-DM1," Clinical Cancer Research, vol. 22, No. 20, Oct. 15, 2016, pp. 5097-5108.
Pardoll, Drew M., "The blockade of immune checkpoints in cancer immunotherapy," Nature Reviews Cancer, vol. 12, 2012, pp. 252-264.
Senter et al., "The discovery and development of brentuximab vedotin for use in relapsed Hodgkin lymphoma and systemic anaplastic large cell lymphoma," Nature Biotechnology, vol. 30, No. 7, Jul. 2012, pp. 631-637.
Stagg et al., "Anti-ErbB-2 mAb therapy requires type I and II interferons and synergizes with anti-PD-1 oranti-CD137 mAb therapy," Proceedings of the National Academy of Sciences, vol. 108, No. 17, Apr. 2011, pp. 7142-7147.
Zawlik et al., "Immune checkpoints in aggressive breast cancer subtypes," Neoplasma, vol. 63, No. 5, 2016, pp. 768-773.
International Searching Authority, "International Search Report," issued in connection with International Patent Application No. PCT/JP2017/044426, dated Feb. 13, 2018.
International Searching Authority, "Written Opinion," issued in connection with International Patent Application No. PCT/JP2017/044426, dated Feb. 13, 2018.
Wolchok, Jedd D., "PD-1 Blockers," Cell, vol. 162, Aug. 2015, 937.

\* cited by examiner

[Figure 1]

SEQ ID NO: 1 - Amino acid sequence of heavy chain of humanized anti-HER2 antibody EVQLVESGGGLVQPGGSLRLSCAASGFNIKDTYIHWVRQAPGKGLEWVARIYPTNGYTRYADSV
KGRFTISADTSKNTAYLQMNSLRAEDTAVYYCSRWGGDGFYAMDYWGQGTLVTVSSASTKGPSV
FPLAPSSKSTSGGTAALGCLVKDYFPEPVTVSWNSGALTSGVHTFPAVLQSSGLYSLSSVVTVP
SSSLGTQTYICNVNHKPSNTKVDKKVEPKSCDKTHTCPPCPAPELLGGPSVFLFPPKPKDTLMI
SRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSP
GK

[Figure 2]

SEQ ID NO: 2 - Amino acid sequence of light chain of humanized anti-HER2 antibody DIQMTQSPSSLSASVGDRVTITCRASQDVNTAVAWYQQKPGKAPKLLIYSASFLYSGVPSRFSG
SRSGTDFTLTISSLQPEDFATYYCQQHYTTPPTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGEC

[Figure 3]

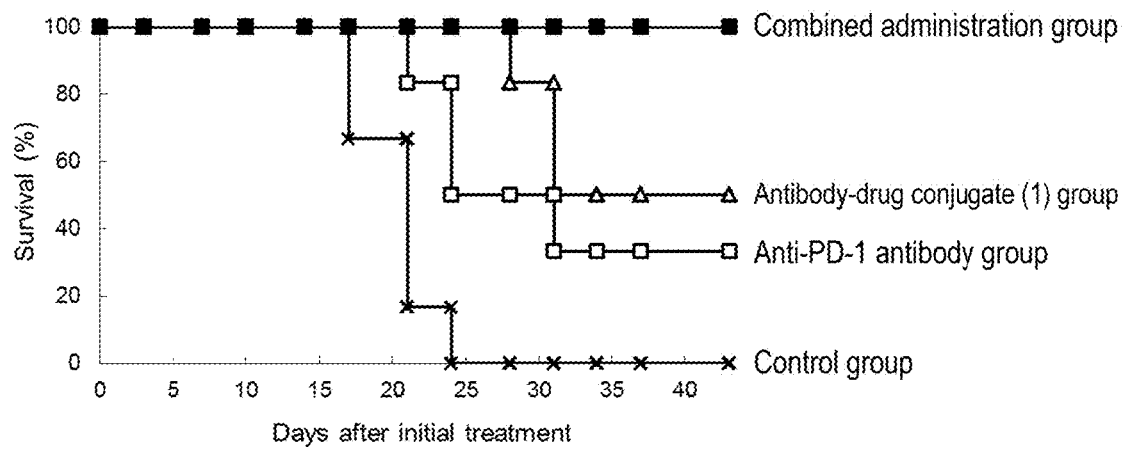

[Figure 4]
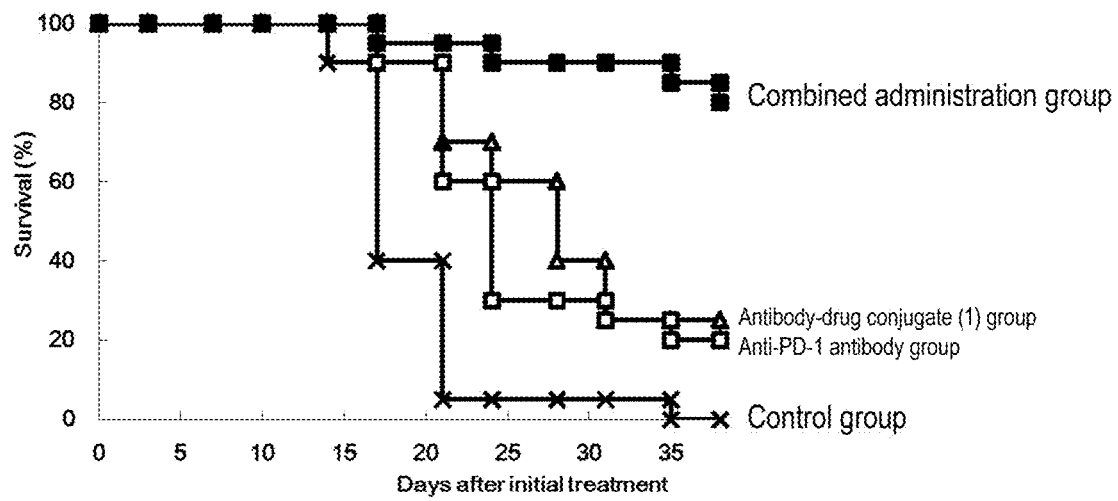
[Figure 5]
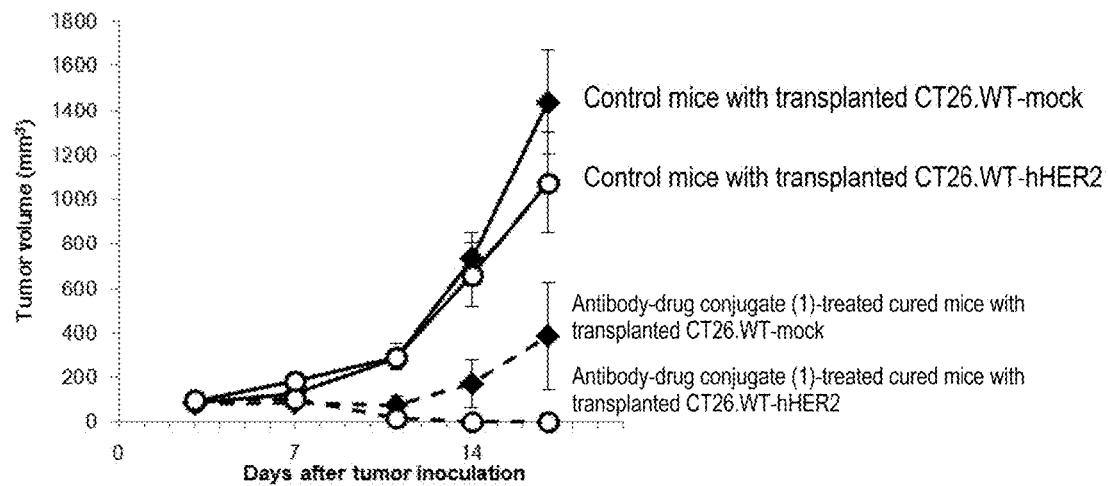

[Figure 6]
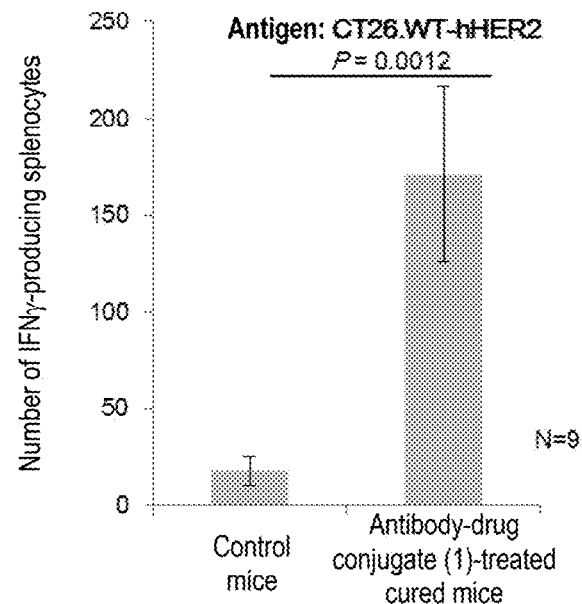
[Figure 7]
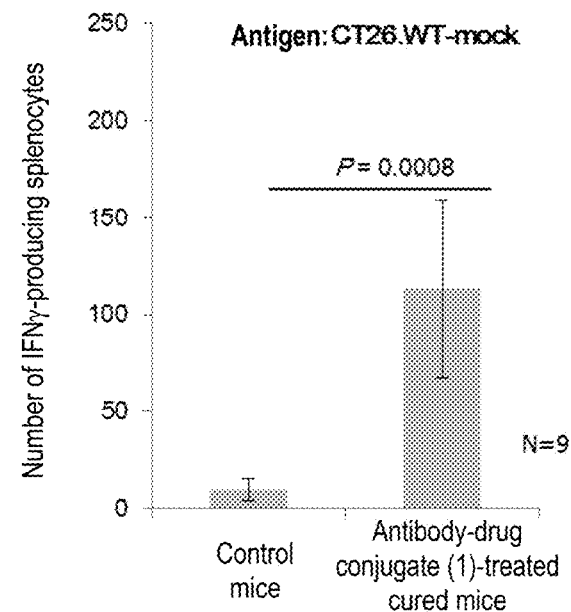

[Figure 8]
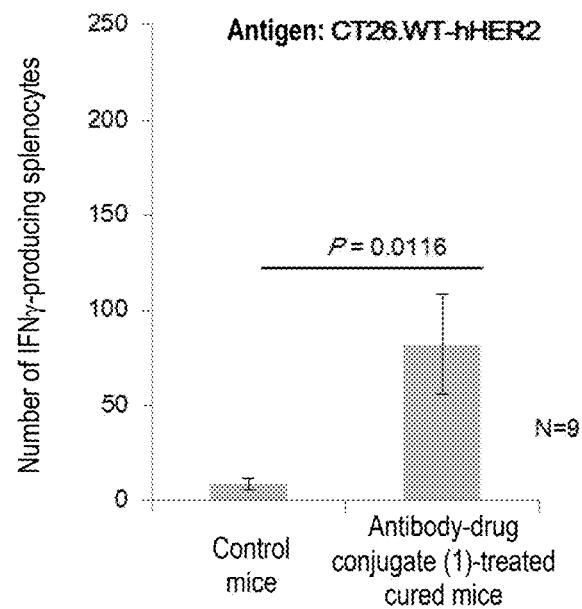
[Figure 9]
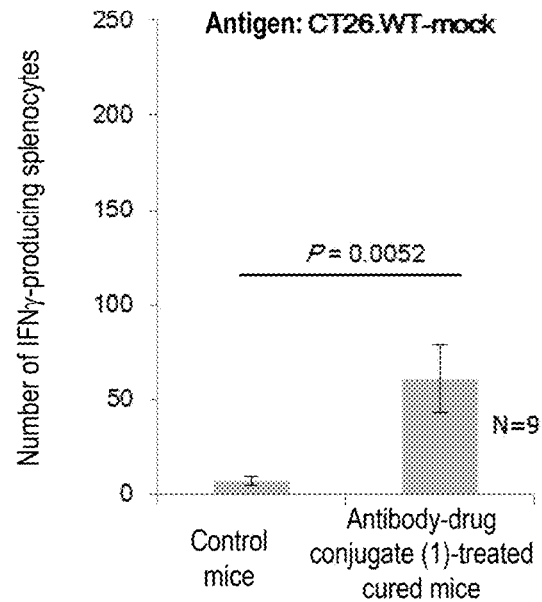

[Figure 10]
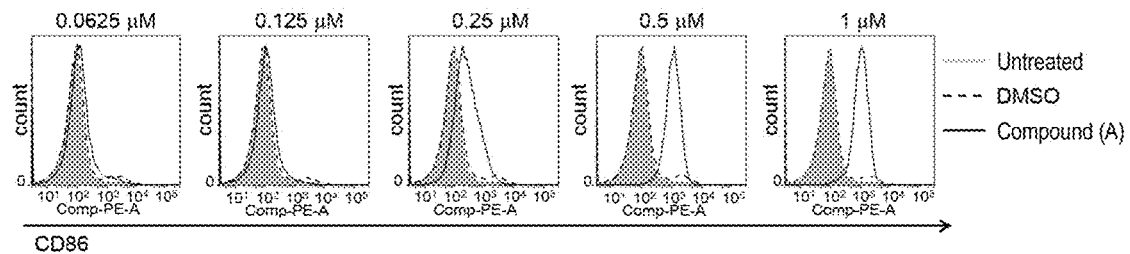
[Figure 11]
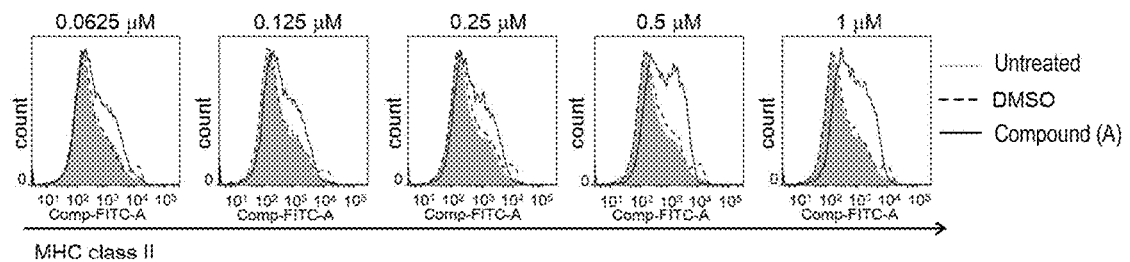
[Figure 12]
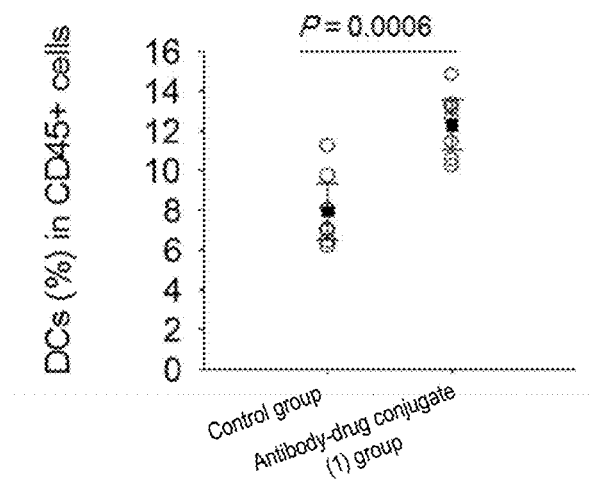

[Figure 13]
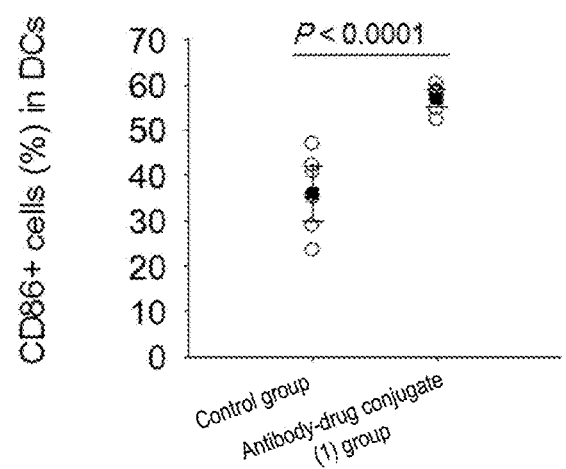
[Figure 14]
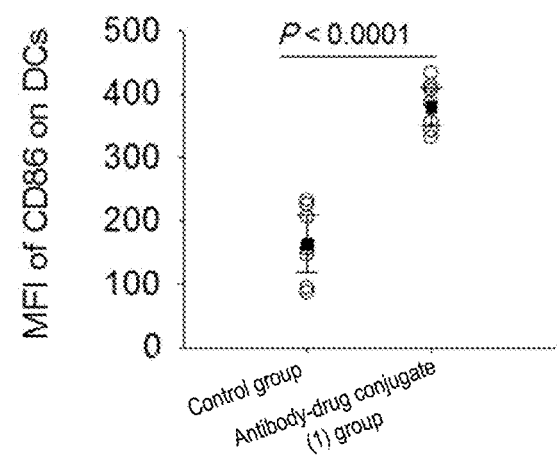

[Figure 15]
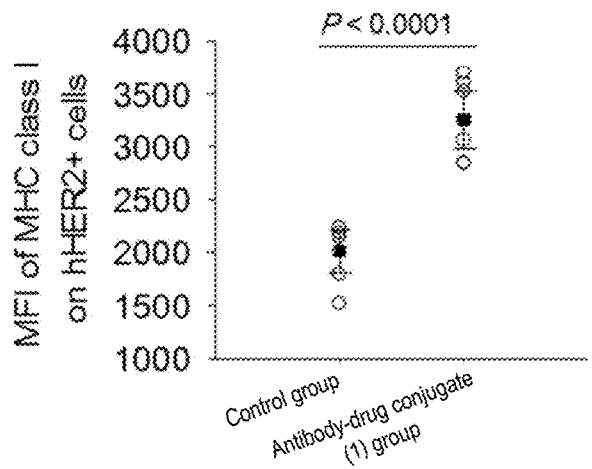
[Figure 16]
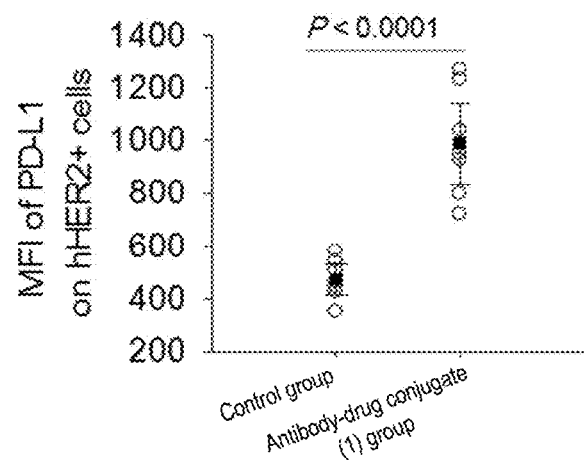

[Figure 17]
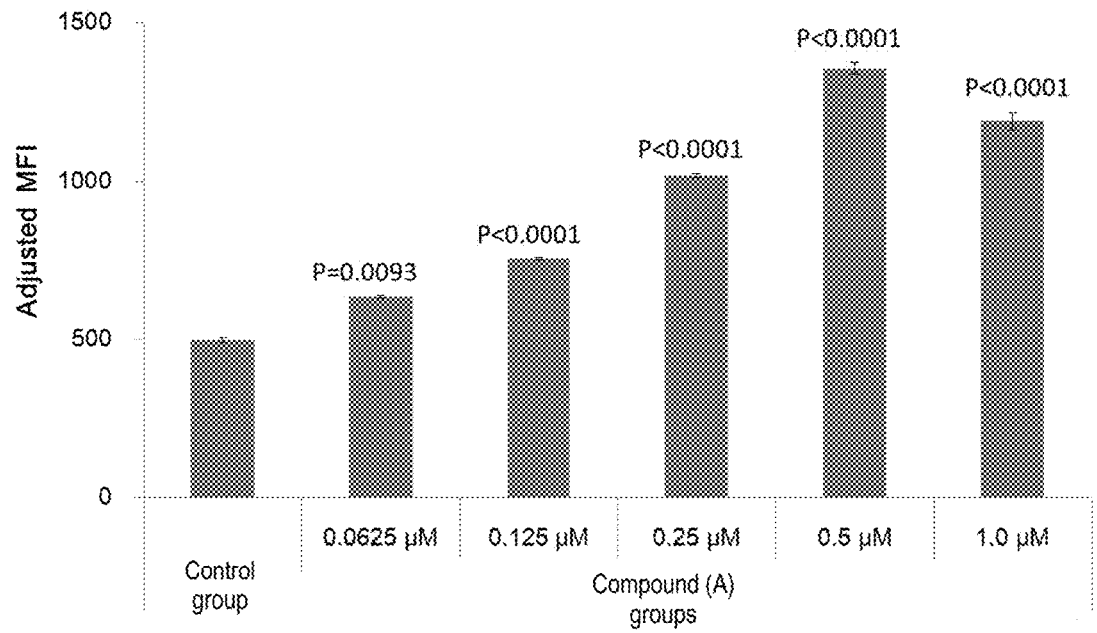
[Figure 18]
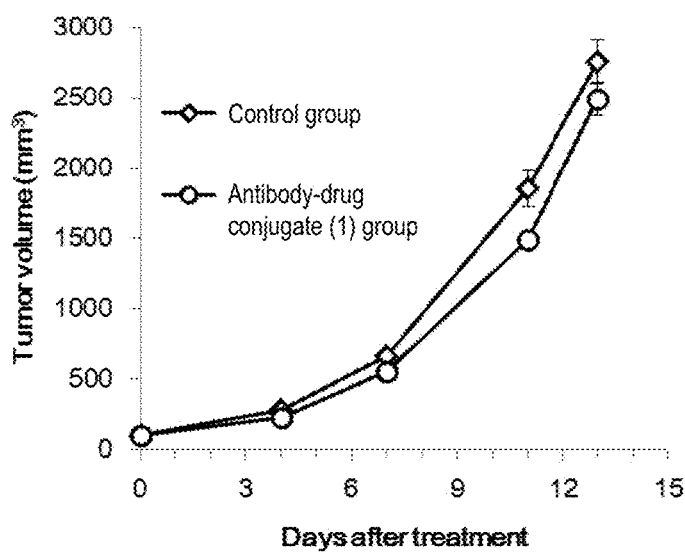

[Figure 19]
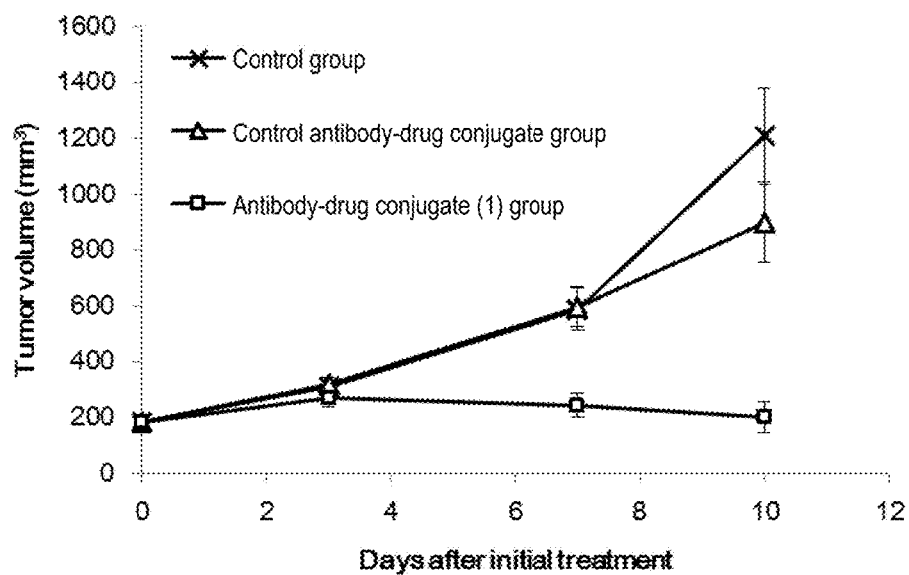
[Figure 20]
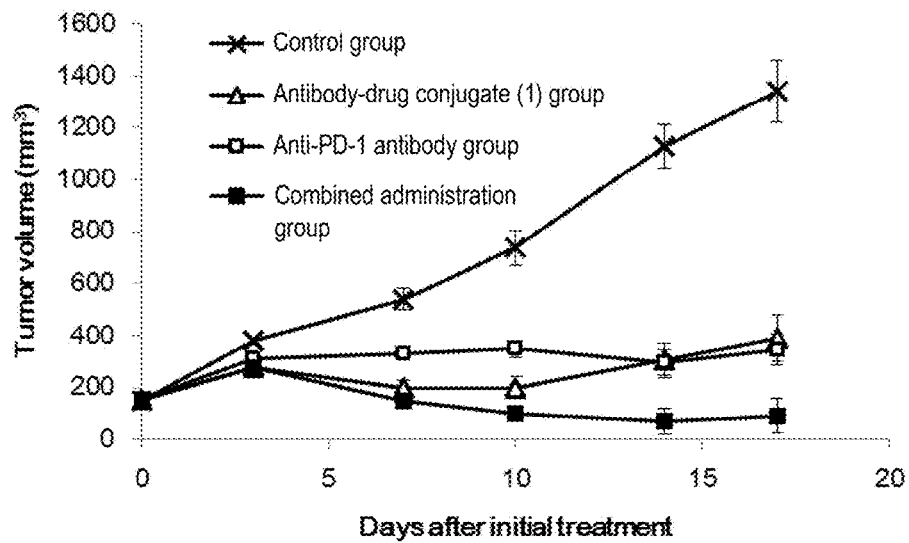

[Figure 21]
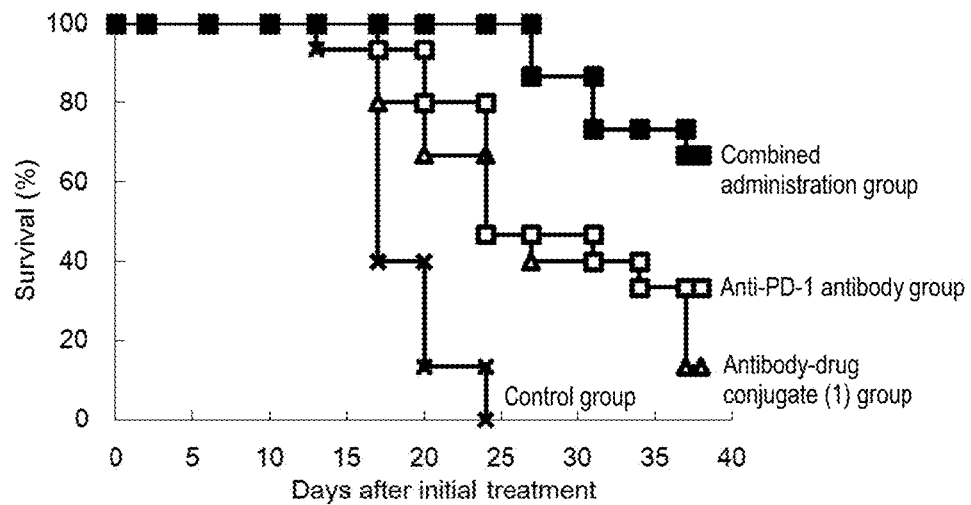
[Figure 22]
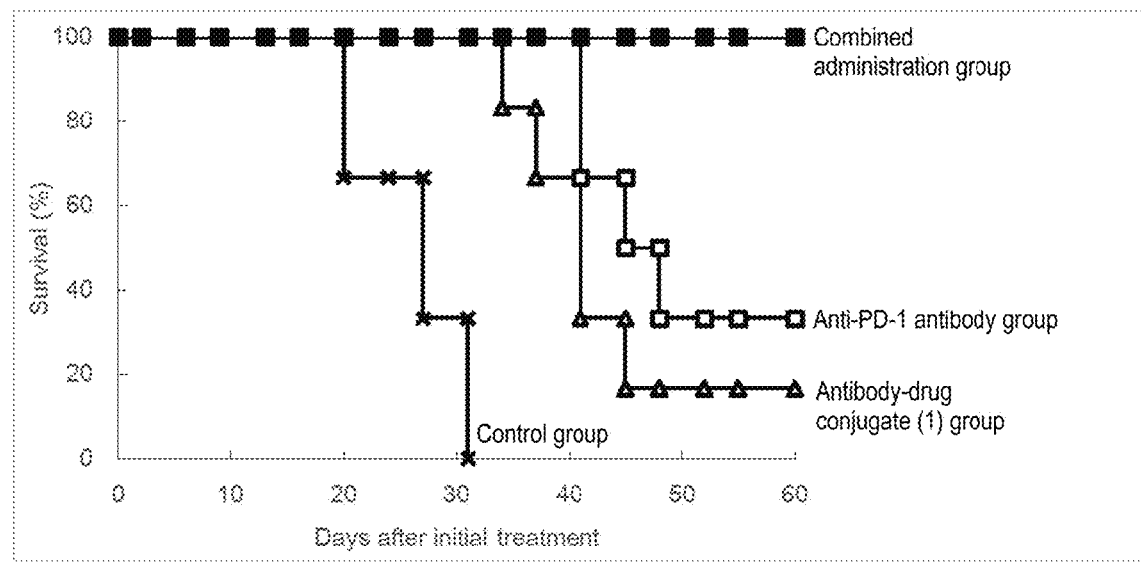

[Figure 23]
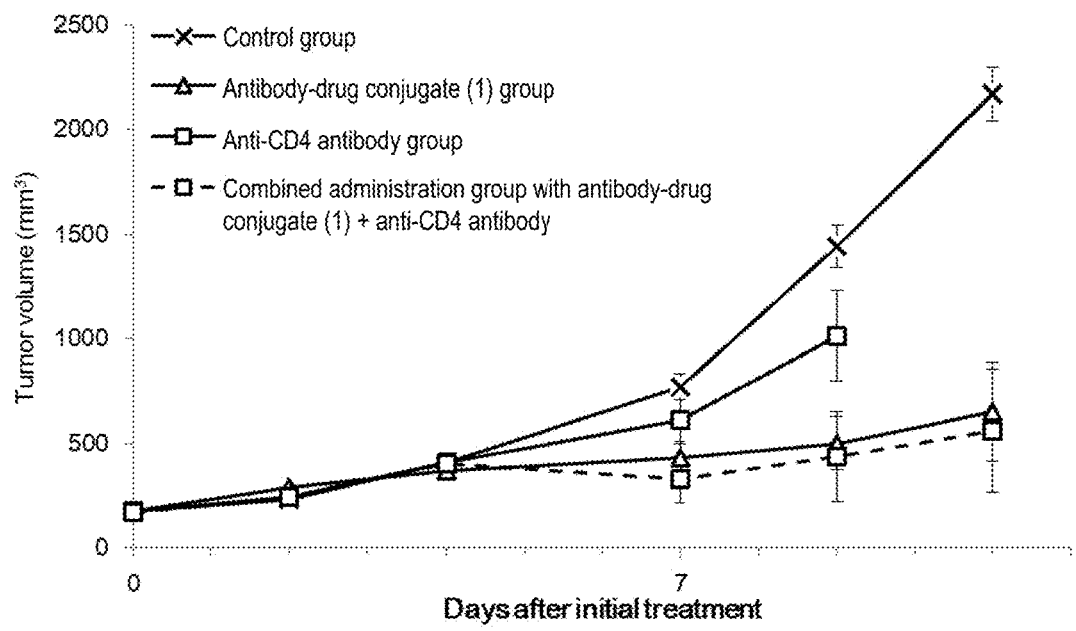
[Figure 24]
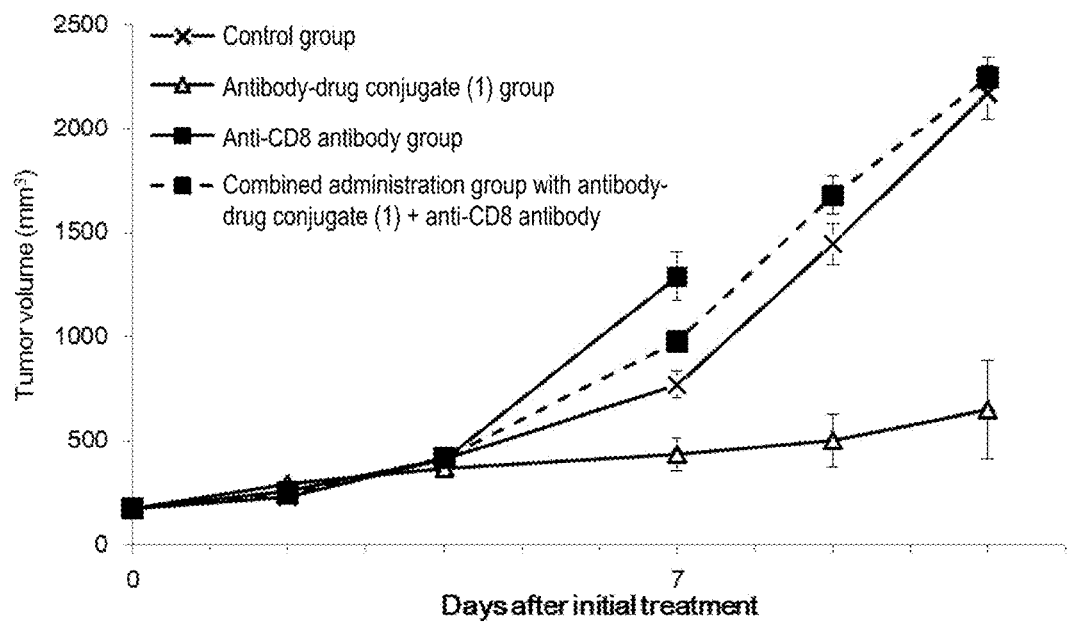

[Figure 25]
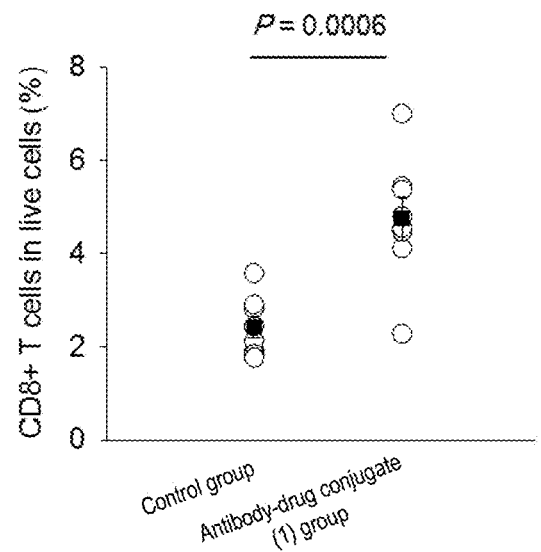
[Figure 26]
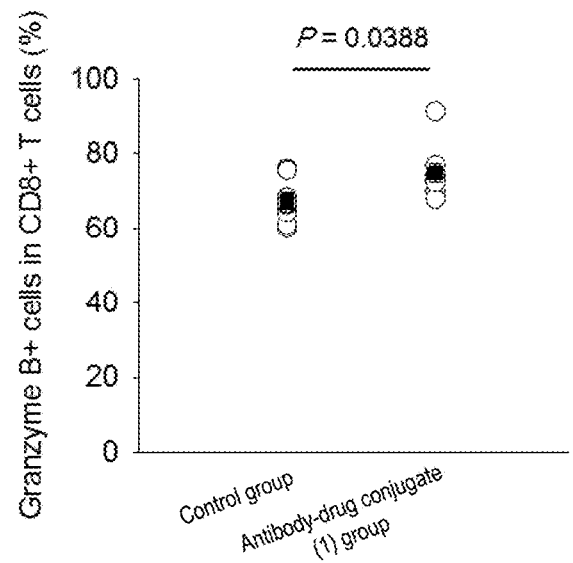

[Figure 27]
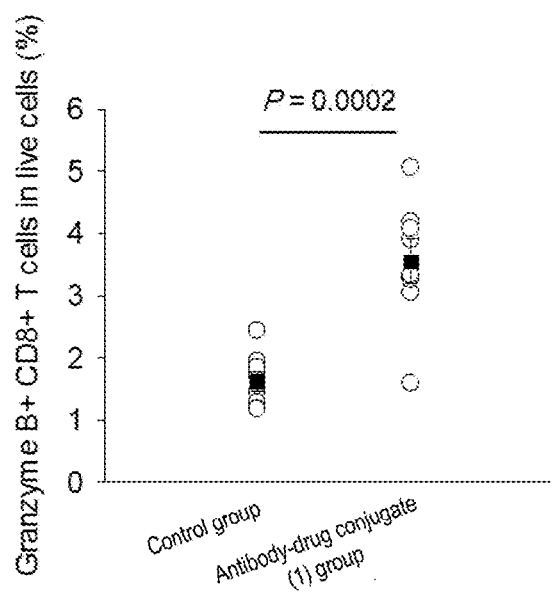
[Figure 28]
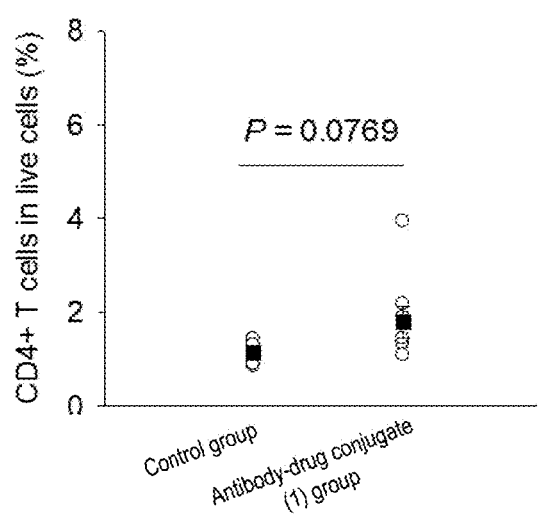

[Figure 29]
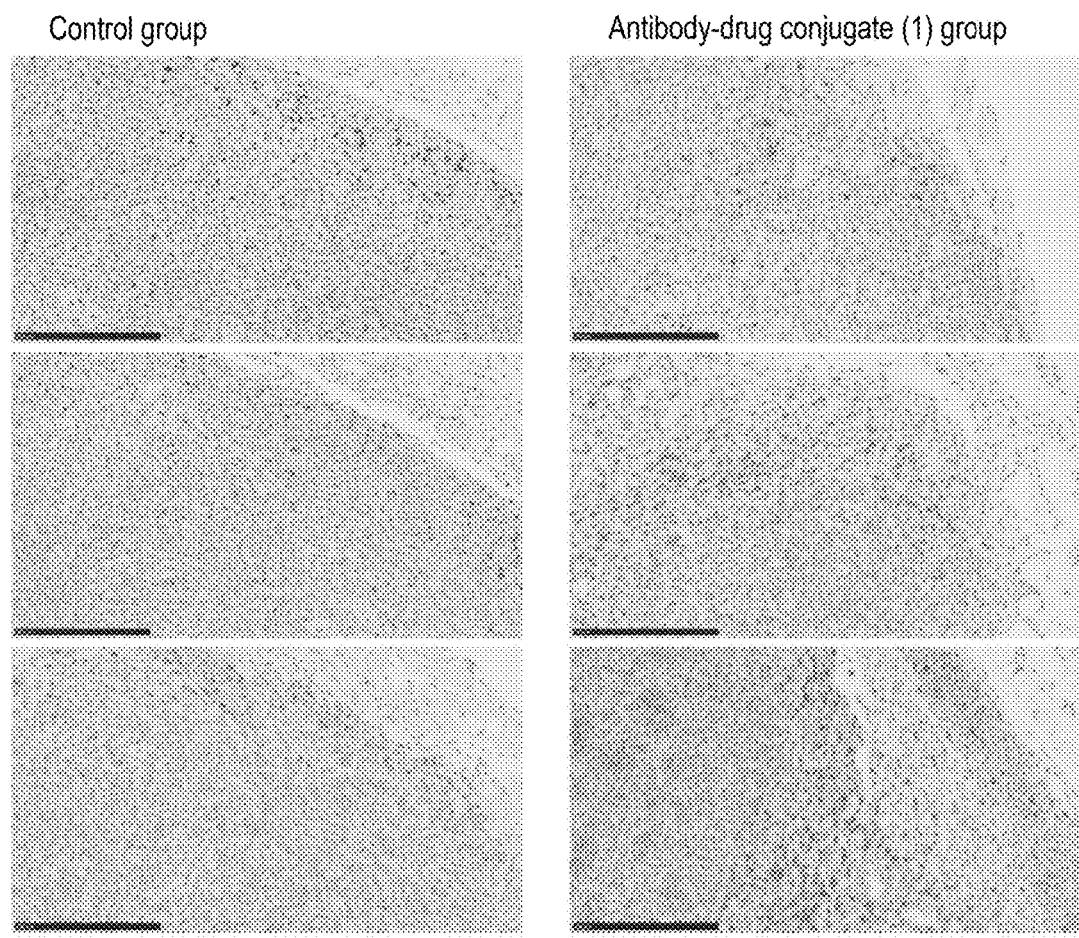
[Figure 30]
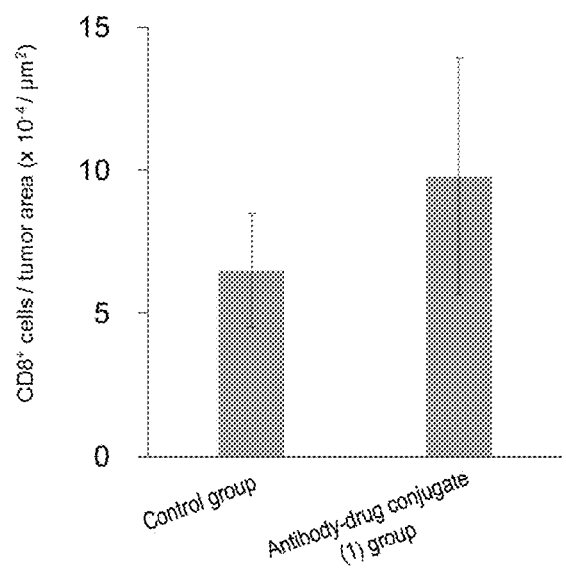

[Figure 31]
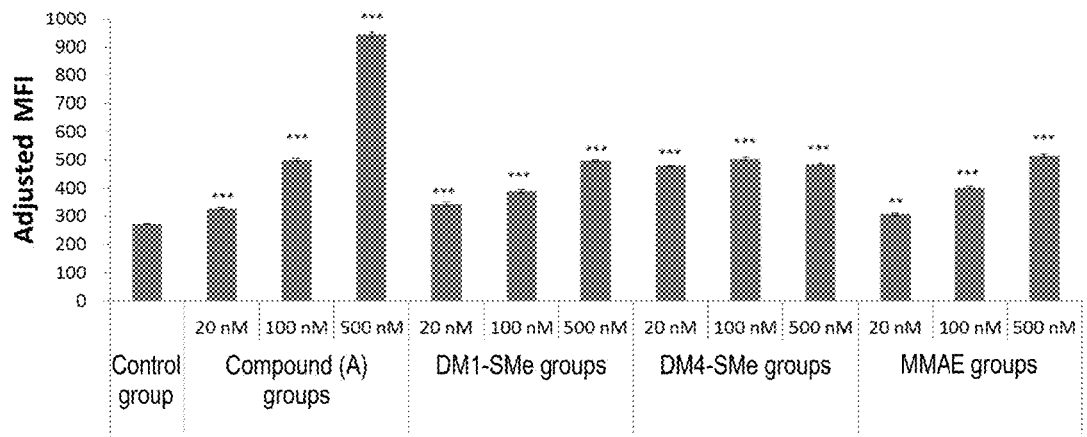
[Figure 32]
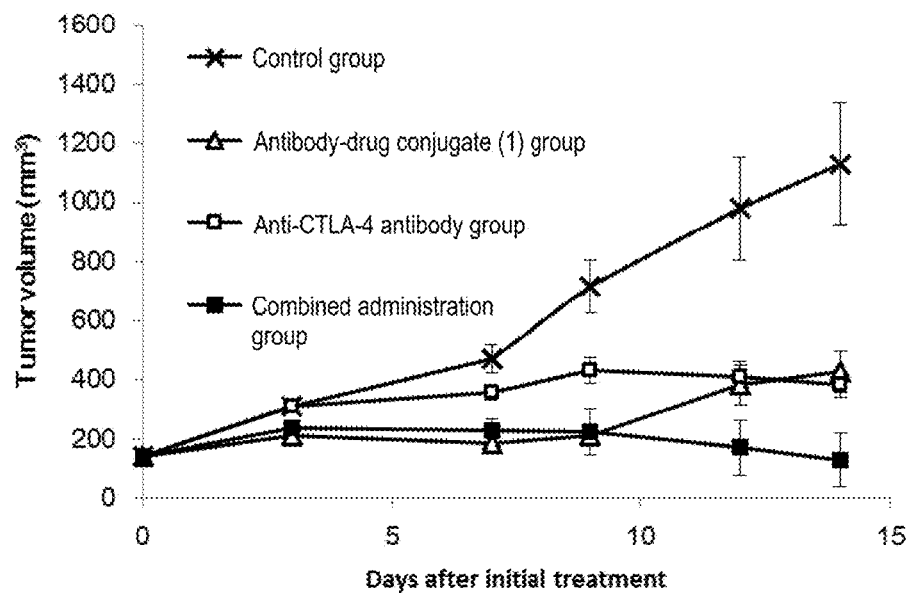

SEQUENCE LISTING

<160> NUMBER OF SEQ ID NOS: 2

<210> SEQ ID NO 1
<211> LENGTH: 450
<212> TYPE: PRT
<213> ORGANISM: Artificial Sequence
<220> FEATURE:
<223> OTHER INFORMATION: Heavy chain of humanized anti-HER2 antibody

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Light chain of humanized anti-HER2 antibody

```
<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

COMBINATION OF ANTIBODY-DRUG CONJUGATE AND IMMUNE CHECKPOINT INHIBITOR

RELATED APPLICATIONS

The present application claims priority under 37 U.S.C. § 371 to International Patent Application No. PCT/JP2017/044426, filed Dec. 11, 2017, which claims priority to and the benefit of Japanese Patent Application Nos. 2016-240442, filed on Dec. 12, 2016, 2017-097067, filed on May 16, 2017, and 2017-183149, filed on Sep. 25, 2017. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, is named 111119-0124 SL.txt and is 7 kb in size.

TECHNICAL FIELD

The present invention relates to a pharmaceutical composition and a therapeutic method wherein a specific antibody-drug conjugate and an immune checkpoint inhibitor are administered in combination, and a pharmaceutical composition and a therapeutic method for use in treatment of a disease that can be ameliorated through an antitumor immunity-activating effect wherein a specific antibody-drug conjugate is included.

BACKGROUND ART

An antibody-drug conjugate (ADC) having a drug with cytotoxicity conjugated to an antibody, whose antigen is expressed on the surface of cancer cells and which also binds to an antigen capable of cellular internalization, and therefore can deliver the drug selectively to cancer cells, is thus expected to cause accumulation of the drug within cancer cells and to kill the cancer cells (Non-Patent Literatures 1 to 5).

As one of such antibody-drug conjugates, an antibody-drug conjugate including an antibody and exatecan, which is a topoisomerase I inhibitor, as components is known (Patent Literatures 1 to 7). Among these, anti-HER2 antibody-drug conjugates (Non-Patent Literatures 6, 7), which exert a particularly superior antitumor effect and safety, are currently under clinical studies.

Immune checkpoint inhibitors are agents that inhibit the immune suppression system and activate antitumor immunity (Non-Patent Literatures 8 to 10). Known examples of immune checkpoint inhibitors include nivolumab (Patent Literature 8) and pembrolizumab (Patent Literature 9) each of which is an anti-PD-1 antibody; atezolizumab (Patent Literature 10), durvalumab (Patent Literature 11), and avelumab (Patent Literature 12), each of which is an anti-PD-L1 antibody; and ipilimumab (Patent Literature 13) and tremelimumab (Patent Literature 14), each of which is an anti-CTLA-4 antibody.

As a case in which an antibody-drug conjugate and an immune checkpoint inhibitor are administered in combination, a study on the use of trastuzumab emtansine (T-DM1) and an anti-CTLA-4/PD-1 antibody in combination is known (Non-Patent Literature 11).

CITATION LIST

Patent Literatures

Patent Literature 1: International Publication No. WO 2014/057687
Patent Literature 2: International Publication No. WO 2014/061277
Patent Literature 3: International Publication No. WO 2015/098099
Patent Literature 4: International Publication No. WO 2015/115091
Patent Literature 5: International Publication No. WO 2015/146132
Patent Literature 6: International Publication No. WO 2015/155976
Patent Literature 7: International Publication No. WO 2015/155998
Patent Literature 8: International Publication No. WO 2006/121168
Patent Literature 9: International Publication No. WO 2008/156712
Patent Literature 10: International Publication No. WO 2010/077634
Patent Literature 11: International Publication No. WO 2011/066389
Patent Literature 12: International Publication No. WO 2013/079174
Patent Literature 13: International Publication No. WO 2001/014424
Patent Literature 14: International Publication No. WO 2000/037504

Non-Patent Literatures

Non-Patent Literature 1: Ducry, L., et al., Bioconjugate Chem. (2010) 21, 5-13.
Non-Patent Literature 2: Alley, S. C., et al., Current Opinion in Chemical Biology (2010) 14, 529-537.
Non-Patent Literature 3: Damle N. K. Expert Opin. Biol. Ther. (2004) 4, 1445-1452.
Non-Patent Literature 4: Senter P. D., et al., Nature Biotechnology (2012) 30, 631-637.
Non-Patent Literature 5: Burris, III et al., J Clin Oncol 29: 398-405.
Non-Patent Literature 6: Ogitani Y. et al., Clinical Cancer Research (2016) 22(20), 5097-5108.
Non-Patent Literature 7: Ogitani Y. et al., Cancer Science (2016) 107, 1039-1046.
Non-Patent Literature 8: Menon S. et al., Cancers (2016) 8, 106.
Non-Patent Literature 9: Pardoll D M., Nat Rev Cancer (2012) 12, 252-264.
Non-Patent Literature 10: Wolchok J D., Cell (2015) 162, 937.
Non-Patent Literature 11: Muller P. et al., Science Translational Medicine (2015) 7(315), 315ra188.

SUMMARY OF INVENTION

Technical Problem

An object of the present invention is to provide a pharmaceutical composition and a therapeutic method which exert a particularly superior antitumor effect and safety through administering an antibody-drug conjugate and an immune checkpoint inhibitor in combination. Another object of the present invention is to provide a pharmaceutical composition and a therapeutic method for use in treatment of a disease that can be ameliorated through an antitumor immunity-activating effect wherein a specific antibody-drug conjugate is included.

Solution to Problem

The present inventors found that an excellent antitumor effect is exerted through administering a specific antibody-drug conjugate and an immune checkpoint inhibitor in combination; and further found that the antibody-drug conjugate has an antitumor immunity-activating effect.

Specifically, the present invention relates to the following.

[1] A pharmaceutical composition wherein an antibody-drug conjugate and an immune checkpoint inhibitor are administered in combination, and the antibody-drug conjugate is an antibody-drug conjugate in which a drug-linker represented by the following formula:

[Formula 1]

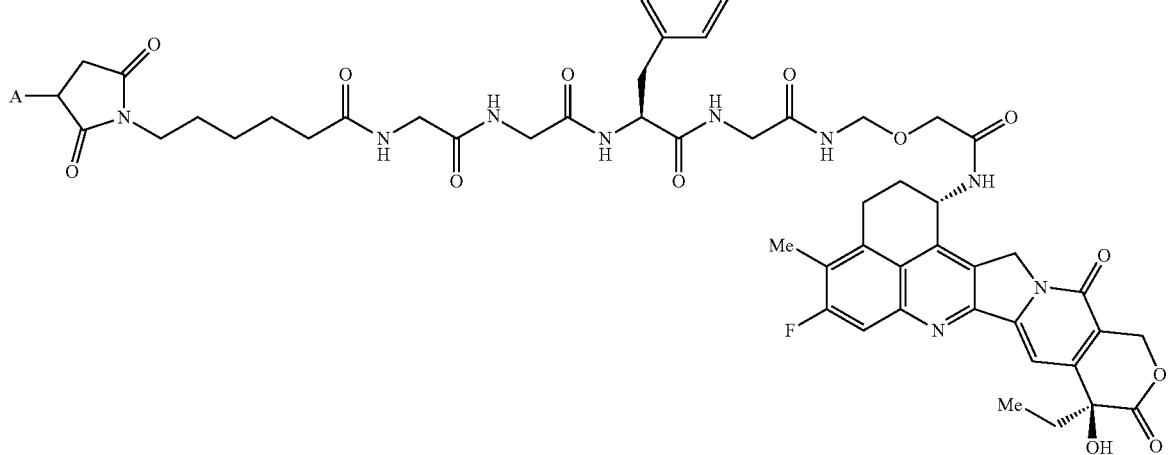

wherein A represents the connecting position to an antibody, is conjugated to the antibody via a thioether bond.

[2] The pharmaceutical composition according to [1], wherein the antibody in the antibody-drug conjugate is an anti-HER2 antibody, an anti-HER3 antibody, an anti-TROP2 antibody, or an anti-B7-H3 antibody.

[3] The pharmaceutical composition according to [2], wherein the antibody in the antibody-drug conjugate is an anti-HER2 antibody.

[4] The pharmaceutical composition according to [2] or [3], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[5] The pharmaceutical composition according to [2] or [3], wherein the anti-HER2 antibody is an antibody comprising a heavy chain consisting of the amino acid sequence represented by SEQ ID NO: 1 and a light chain consisting of the amino acid sequence represented by SEQ ID NO: 2.

[6] The pharmaceutical composition according to any one of [1] to [5], wherein the average number of units of the drug-linker conjugated per antibody molecule in the antibody-drug conjugate is in the range of from 2 to 8.

[7] The pharmaceutical composition according to any one of [1] to [5], wherein the average number of units of the drug-linker conjugated per antibody molecule in the antibody-drug conjugate is in the range of from 7 to 8.

[8] The pharmaceutical composition according to any one of [1] to [5], wherein the average number of units of the drug-linker conjugated per antibody molecule in the antibody-drug conjugate is in the range of from 7.5 to 8.

[9] The pharmaceutical composition according to any one of [1] to [8], wherein the immune checkpoint inhibitor is an anti-PD-1 antibody, an anti-PD-L1 antibody, or an anti-CTLA-4 antibody.

[10] The pharmaceutical composition according to [9], wherein the immune checkpoint inhibitor is an anti-PD-1 antibody.

[11] The pharmaceutical composition according to [9], wherein the immune checkpoint inhibitor is an anti-PD-L1 antibody.

[12] The pharmaceutical composition according to [9], wherein the immune checkpoint inhibitor is an anti-CTLA-4 antibody.

[13] The pharmaceutical composition according to any one of [1] to [12], wherein the antibody-drug conjugate and the immune checkpoint inhibitor are separately contained as active components in different formulations, and are administered simultaneously or at different times.

[14] The pharmaceutical composition according to any one of [1] to [12], wherein the antibody-drug conjugate and the immune checkpoint inhibitor are contained as active components in a single formulation and administered.

[15] The pharmaceutical composition according to any one of [1] to [14], wherein the composition is for treating cancer.

[16] The pharmaceutical composition according to [15], wherein the cancer is at least one selected from the group consisting of lung cancer, urothelial cancer, colorectal cancer, prostate cancer, ovarian cancer, pancreatic cancer, breast cancer, bladder cancer, gastric cancer, esophagogastric junction adenocarcinoma, gastrointestinal stromal tumor, uterine cervix cancer, esophageal cancer, squamous cell carcinoma, peritoneal cancer, liver cancer, hepatocellular cancer, endometrial cancer, uterine cancer, salivary gland cancer, kidney cancer, vulval cancer, thyroid cancer, penis cancer, leukemia, malignant lymphoma, plasmacytoma, myeloma, neuroepithelial tissue tumor, nerve sheath tumor, head-and-neck cancer, skin cancer, pharyngeal cancer, gallbladder cancer, bile duct cancer, mesothelioma, Paget's disease, and sarcoma.

[17] The pharmaceutical composition according to [16], wherein the cancer is colorectal cancer.

[18] The pharmaceutical composition according to [16], wherein the cancer is breast cancer.

[19] The pharmaceutical composition according to any one of [1] to [18], wherein the antibody-drug conjugate has an antitumor immunity-activating effect.

[20] The pharmaceutical composition according to any one of [1] to [19], wherein the antibody-drug conjugate has at least one effect selected from the group consisting of:
(1) a promoting effect on growth of intratumor CD8-positive T cells; and
(2) an activating effect on intratumor CD8-positive T cells.

[21] The pharmaceutical composition according to any one of [1] to [20], wherein the antibody-drug conjugate has a promoting effect on the formation of immune memory against tumor.

[22] The pharmaceutical composition according to [21], wherein the tumor is expressing an antigen for the antibody in the antibody-drug conjugate.

[23] The pharmaceutical composition according to [21], wherein a part of the cells of the tumor are not expressing an antigen for the antibody in the antibody-drug conjugate.

[24] The pharmaceutical composition according to any one of [1] to [23], wherein the antibody-drug conjugate has at least one effect selected from the group consisting of:
(1) a promoting effect on increase of the number of dendritic cells in a tumor;
(2) an activating effect on dendritic cells; and
(3) a promoting effect on elevation of the expression level of MHC class I on cancer cells.

[25] The pharmaceutical composition according to any one of [1] to [24], wherein the immune checkpoint inhibitor deactivates an immunosuppression signal generated through elevation of the expression level of PD-L1 on cancer cells promoted by the antibody-drug conjugate, and thereby the antibody-drug conjugate exhibits a higher antitumor effect.

[26] A pharmaceutical composition for use in treatment of a disease that can be ameliorated through an antitumor immunity-activating effect, wherein the pharmaceutical composition contains an antibody-drug conjugate in which a drug-linker represented by the following formula:

[Formula 2]

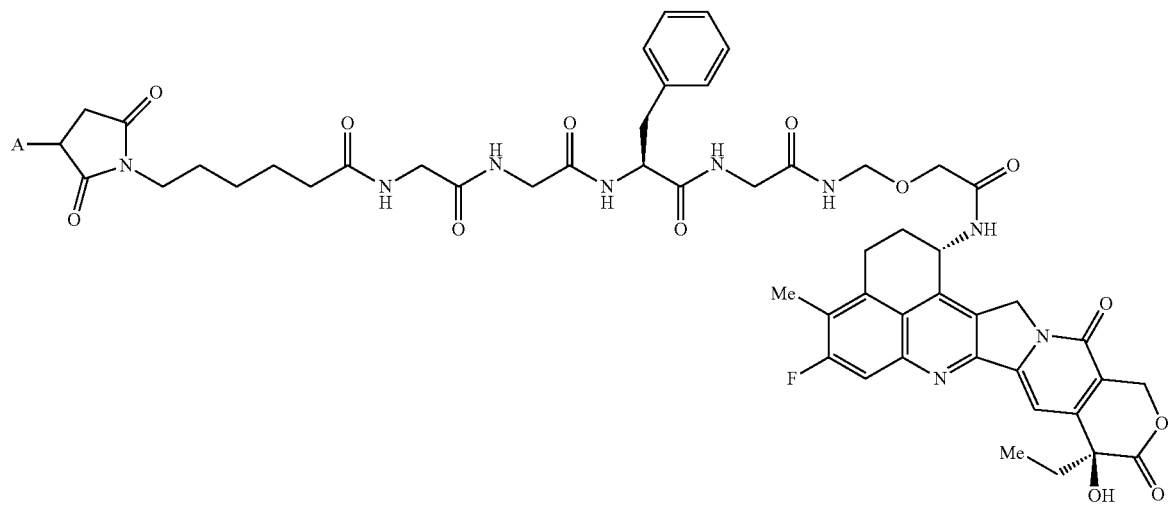

wherein A represents the connecting position to an antibody, is conjugated to the antibody via a thioether bond.

[27] The pharmaceutical composition according to [26], wherein the antibody-drug conjugate has at least one effect selected from the group consisting of:
(1) a promoting effect on growth of intratumor CD8-positive T cells; and
(2) an activating effect on intratumor CD8-positive T cells.

[28] The pharmaceutical composition according to [26] or [27], wherein the antibody-drug conjugate has a promoting effect on the formation of immune memory against tumor.

[29] The pharmaceutical composition according to [28], wherein the tumor is expressing an antigen for the antibody in the antibody-drug conjugate.

[30] The pharmaceutical composition according to [28], wherein a part of the cells of the tumor are not expressing an antigen for the antibody in the antibody-drug conjugate.

[31] The pharmaceutical composition according to any one of [26] to [30], wherein the antibody-drug conjugate has at least one effect selected from the group consisting of:
(1) a promoting effect on increase of the number of dendritic cells in a tumor;

(2) an activating effect on dendritic cells; and (3) a promoting effect on elevation of the expression level of MHC class I on cancer cells.

[32] The pharmaceutical composition according to any one of [26] to [31], wherein the antibody in the antibody-drug conjugate is an anti-HER2 antibody, an anti-HER3 antibody, an anti-TROP2 antibody, or an anti-B7-H3 antibody.

[33] The pharmaceutical composition according to [32], wherein the antibody in the antibody-drug conjugate is an anti-HER2 antibody.

[34] The pharmaceutical composition according to [32] or [33], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[35] The pharmaceutical composition according to [32] or [33], wherein the anti-HER2 antibody is an antibody comprising a heavy chain consisting of the amino acid sequence represented by SEQ ID NO: 1 and a light chain consisting of the amino acid sequence represented by SEQ ID NO: 2.

[36] The pharmaceutical composition according to any one of [26] to [35], wherein the average number of units of the drug-linker conjugated per antibody molecule in the antibody-drug conjugate is in the range of from 2 to 8.

[37] The pharmaceutical composition according to any one of [26] to [35], wherein the average number of units of the drug-linker conjugated per antibody molecule in the antibody-drug conjugate is in the range of from 7 to 8.

[38] The pharmaceutical composition according to any one of [26] to [35], wherein the average number of units of the drug-linker conjugated per antibody molecule in the antibody-drug conjugate is in the range of from 7.5 to 8.

[39] The pharmaceutical composition according to any one of [26] to [38], wherein the disease is at least one selected from the group consisting of lung cancer, urothelial cancer, colorectal cancer, prostate cancer, ovarian cancer, pancreatic cancer, breast cancer, bladder cancer, gastric cancer, esophagogastric junction adenocarcinoma, gastrointestinal stromal tumor, uterine cervix cancer, esophageal cancer, squamous cell carcinoma, peritoneal cancer, liver cancer, hepatocellular cancer, endometrial cancer, uterine cancer, salivary gland cancer, kidney cancer, vulval cancer, thyroid cancer, penis cancer, leukemia, malignant lymphoma, plasmacytoma, myeloma, neuroepithelial tissue tumor, nerve sheath tumor, head-and-neck cancer, skin cancer, pharyngeal cancer, gallbladder cancer, bile duct cancer, mesothelioma, Paget's disease, and sarcoma.

[40] The pharmaceutical composition according to [39], wherein the disease is colorectal cancer.

[41] The pharmaceutical composition according to [39], wherein the disease is breast cancer.

[42] A pharmaceutical composition for use in treatment of a disease that can be ameliorated through an antitumor immunity-activating effect, wherein the pharmaceutical composition releases the compound represented by the following formula:

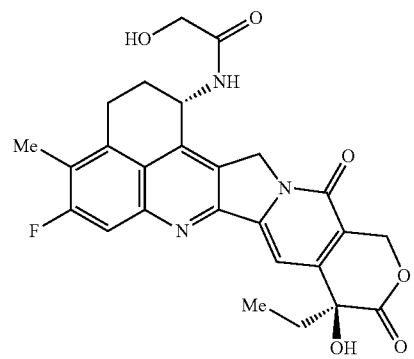

[Formula 3]

in a tumor.

[43] The pharmaceutical composition according to [42], wherein the compound has at least one effect selected from the group consisting of:

(1) a promoting effect on growth of intratumor CD8-positive T cells; and (2) an activating effect on intratumor CD8-positive T cells.

[44] The pharmaceutical composition according to [42] or [43], wherein the compound has a promoting effect on the formation of immune memory against tumor.

[45] The pharmaceutical composition according to any one of [42] to [44], wherein the compound has at least one effect selected from the group consisting of:

(1) a promoting effect on increase of the number of dendritic cells in a tumor;

(2) an activating effect on dendritic cells; and (3) a promoting effect on elevation of the expression level of MHC class I on cancer cells.

[46] The pharmaceutical composition according to any one of [42] to [45], wherein the disease is at least one selected from the group consisting of lung cancer, urothelial cancer, colorectal cancer, prostate cancer, ovarian cancer, pancreatic cancer, breast cancer, bladder cancer, gastric cancer, esophagogastric junction adenocarcinoma, gastrointestinal stromal tumor, uterine cervix cancer, esophageal cancer, squamous cell carcinoma, peritoneal cancer, liver cancer, hepatocellular cancer, endometrial cancer, uterine cancer, salivary gland cancer, kidney cancer, vulval cancer, thyroid cancer, penis cancer, leukemia, malignant lymphoma, plasmacytoma, myeloma, neuroepithelial tissue tumor, nerve sheath tumor, head-and-neck cancer, skin cancer, pharyngeal cancer, gallbladder cancer, bile duct cancer, mesothelioma, Paget's disease, and sarcoma.

[47] A therapeutic method wherein an antibody-drug conjugate and an immune checkpoint inhibitor are administered in combination, and the antibody-drug conjugate is an antibody-drug conjugate in which a drug-linker represented by the following formula:

[Formula 4]

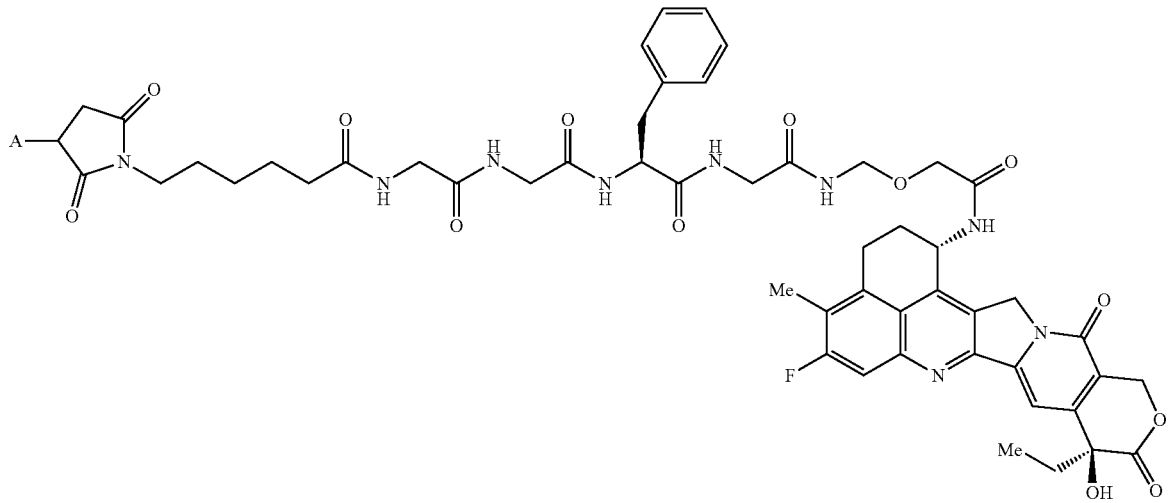

wherein A represents the connecting position to an antibody, is conjugated to the antibody via a thioether bond.

[48] The therapeutic method according to [47], wherein the antibody in the antibody-drug conjugate is an anti-HER2 antibody, an anti-HER3 antibody, an anti-TROP2 antibody, or an anti-B7-H3 antibody.

[49] The therapeutic method according to [48], wherein the antibody in the antibody-drug conjugate is an anti-HER2 antibody.

[50] The therapeutic method according to [48] or [49], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[51] The therapeutic method according to [48] or [49], wherein the anti-HER2 antibody is an antibody comprising a heavy chain consisting of the amino acid sequence represented by SEQ ID NO: 1 and a light chain consisting of the amino acid sequence represented by SEQ ID NO: 2.

[52] The therapeutic method according to any one of [47] to [51], wherein the average number of units of the drug-linker conjugated per antibody molecule in the antibody-drug conjugate is in the range of from 2 to 8.

[53] The therapeutic method according to any one of [47] to [51], wherein the average number of units of the drug-linker conjugated per antibody molecule in the antibody-drug conjugate is in the range of from 7 to 8.

[54] The therapeutic method according to any one of [47] to [51], wherein the average number of units of the drug-linker conjugated per antibody molecule in the antibody-drug conjugate is in the range of from 7.5 to 8.

[55] The therapeutic method according to any one of [47] to [54], wherein the immune checkpoint inhibitor is an anti-PD-1 antibody, an anti-PD-L1 antibody, or an anti-CTLA-4 antibody.

[56] The therapeutic method according to [55], wherein the immune checkpoint inhibitor is an anti-PD-1 antibody.

[57] The therapeutic method according to [55], wherein the immune checkpoint inhibitor is an anti-PD-L1 antibody.

[58] The therapeutic method according to [55], wherein the immune checkpoint inhibitor is an anti-CTLA-4 antibody.

[59] The therapeutic method according to any one of [47] to [58], wherein the antibody-drug conjugate and the immune checkpoint inhibitor are separately contained as active components in different formulations, and are administered simultaneously or at different times.

[60] The therapeutic method according to any one of [47] to [58], wherein the antibody-drug conjugate and the immune checkpoint inhibitor are contained as active components in a single formulation and administered.

[61] The therapeutic method according to any one of [47] to [60], wherein the therapeutic method is for treating cancer.

[62] The therapeutic method according to [61], wherein the cancer is at least one selected from the group consisting of lung cancer, urothelial cancer, colorectal cancer, prostate cancer, ovarian cancer, pancreatic cancer, breast cancer, bladder cancer, gastric cancer, esophagogastric junction adenocarcinoma, gastrointestinal stromal tumor, uterine cervix cancer, esophageal cancer, squamous cell carcinoma, peritoneal cancer, liver cancer, hepatocellular cancer, endometrial cancer, uterine cancer, salivary gland cancer, kidney cancer, vulval cancer, thyroid cancer, penis cancer, leukemia, malignant lymphoma, plasmacytoma, myeloma, neuroepithelial tissue tumor, nerve sheath tumor, head-and-neck cancer, skin cancer, pharyngeal cancer, gallbladder cancer, bile duct cancer, mesothelioma, Paget's disease, and sarcoma.

[63] The therapeutic method according to [62], wherein the cancer is colorectal cancer.

[64] The therapeutic method according to [62], wherein the cancer is breast cancer.

[65] The therapeutic method according to any one of [47] to [64], wherein the antibody-drug conjugate has an antitumor immunity-activating effect.

[66] The pharmaceutical composition according to any one of [47] to [65], wherein the antibody-drug conjugate has at least one effect selected from the group consisting of:

(1) a promoting effect on growth of intratumor CD8-positive T cells; and (2) an activating effect on intratumor CD8-positive T cells.

[67] The therapeutic method according to any one of [47] to [66], wherein the antibody-drug conjugate has a promoting effect on the formation of immune memory against tumor.

[68] The therapeutic method according to [67], wherein the tumor is expressing an antigen for the antibody in the antibody-drug conjugate.
[69] The therapeutic method according to [67], wherein a part of the cells of the tumor are not expressing an antigen for the antibody in the antibody-drug conjugate.
[70] The therapeutic method according to any one of [47] to [69], wherein the antibody-drug conjugate has at least one effect selected from the group consisting of:
 (1) a promoting effect on increase of the number of dendritic cells in a tumor;
 (2) an activating effect on dendritic cells; and
 (3) a promoting effect on elevation of the expression level of MHC class I on cancer cells.
[71] The therapeutic method according to any one of [47] to [70], wherein the immune checkpoint inhibitor deactivates an immunosuppression signal generated through elevation of the expression level of PD-L1 on cancer cells promoted by the antibody-drug conjugate, and thereby the antibody-drug conjugate exhibits a higher antitumor effect.
[72] A therapeutic method for use in treatment of a disease that can be ameliorated through an antitumor immunity-activating effect wherein an antibody-drug conjugate in which a drug-linker represented by the following formula:

[77] The therapeutic method according to any one of [72] to [76], wherein the antibody-drug conjugate has at least one effect selected from the group consisting of:
 (1) a promoting effect on increase of the number of dendritic cells in a tumor;
 (2) an activating effect on dendritic cells; and
 (3) a promoting effect on elevation of the expression level of MHC class I on cancer cells.
[78] The therapeutic method according to any one of [72] to [77], wherein the antibody in the antibody-drug conjugate is an anti-HER2 antibody, an anti-HER3 antibody, an anti-TROP2 antibody, or an anti-B7-H3 antibody.
[79] The therapeutic method according to [78], wherein the antibody in the antibody-drug conjugate is an anti-HER2 antibody.
[80] The therapeutic method according to [78] or [79], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.
[81] The therapeutic method according to [78] or [79], wherein the anti-HER2 antibody is an antibody comprising a heavy chain consisting of the amino acid sequence repre-

[Formula 5]

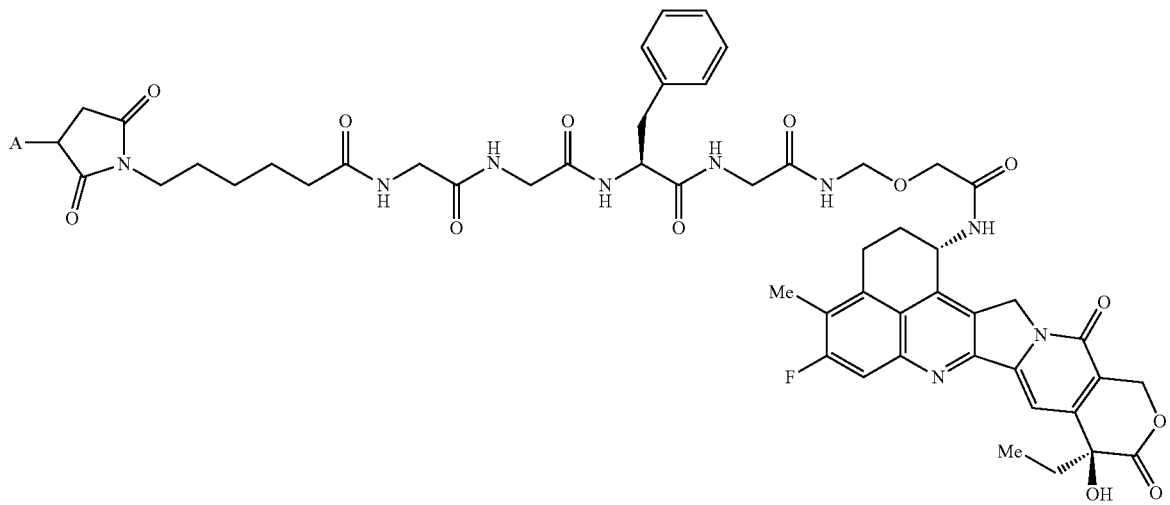

wherein A represents the connecting position to an antibody, is conjugated to the antibody via a thioether bond, is administered.
[73] The therapeutic method according to [72], wherein the antibody-drug conjugate has at least one effect selected from the group consisting of:
 (1) a promoting effect on growth of intratumor CD8-positive T cells; and
 (2) an activating effect on intratumor CD8-positive T cells.
[74] The therapeutic method according to [72] or [73], wherein the antibody-drug conjugate has a promoting effect on the formation of immune memory against tumor.
[75] The therapeutic method according to [74], wherein the tumor is expressing an antigen for the antibody in the antibody-drug conjugate.
[76] The therapeutic method according to [74], wherein a part of the cells of the tumor are not expressing an antigen for the antibody in the antibody-drug conjugate.

sented by SEQ ID NO: 1 and a light chain consisting of the amino acid sequence represented by SEQ ID NO: 2.
[82] The therapeutic method according to any one of [72] to [81], wherein the average number of units of the drug-linker conjugated per antibody molecule in the antibody-drug conjugate is in the range of from 2 to 8.
[83] The therapeutic method according to any one of [72] to [81], wherein the average number of units of the drug-linker conjugated per antibody molecule in the antibody-drug conjugate is in the range of from 7 to 8.
[84] The therapeutic method according to any one of [72] to [81], wherein the average number of units of the drug-linker conjugated per antibody molecule in the antibody-drug conjugate is in the range of from 7.5 to 8.
[85] The therapeutic method according to any one of [72] to [84], wherein the disease is at least one selected from the group consisting of lung cancer, urothelial cancer, colorectal cancer, prostate cancer, ovarian cancer, pancreatic cancer, breast cancer, bladder cancer, gastric cancer, esophagogastric junction adenocarcinoma, gastrointestinal stromal tumor, uterine cervix cancer, esophageal cancer, squamous cell carcinoma, peritoneal cancer, liver cancer, hepatocellular cancer, endometrial cancer, uterine cancer, salivary gland cancer, kidney cancer, vulval cancer, thyroid cancer, penis cancer, leukemia, malignant lymphoma, plasmacytoma, myeloma, neuroepithelial tissue tumor, nerve sheath tumor, head-and-neck cancer, skin cancer, pharyngeal cancer, gallbladder cancer, bile duct cancer, mesothelioma, Paget's disease, and sarcoma.

[86] The therapeutic method according to [85], wherein the disease is colorectal cancer.

[87] The therapeutic method according to [85], wherein the disease is breast cancer.

[88] A therapeutic method for use in treatment of a disease that can be ameliorated through an antitumor immunity-activating effect, wherein the therapeutic method releases the compound represented by the following formula:

[Formula 6]

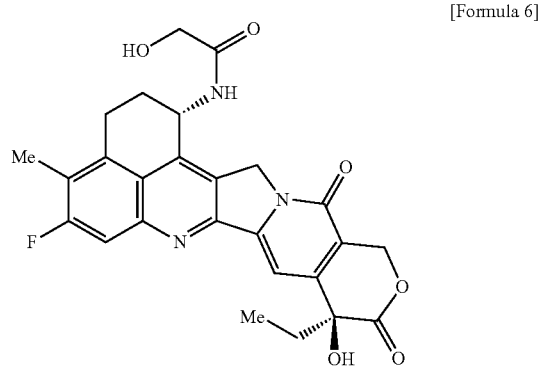

in a tumor.

[89] The therapeutic method according to [88], wherein the compound has at least one effect selected from the group consisting of:

(1) a promoting effect on growth of intratumor CD8-positive T cells; and (2) an activating effect on intratumor CD8-positive T cells.

[90] The therapeutic method according to [88] or [89], wherein the compound has a promoting effect on the formation of immune memory against tumor.

[91] The therapeutic method according to any one of [88] to [90], wherein the compound has at least one effect selected from the group consisting of:

(1) a promoting effect on increase of the number of dendritic cells in a tumor;

(2) an activating effect on dendritic cells; and (3) a promoting effect on elevation of the expression level of MHC class I on cancer cells.

[92] The therapeutic method according to any one of [88] to [91], wherein the disease is at least one selected from the group consisting of lung cancer, urothelial cancer, colorectal cancer, prostate cancer, ovarian cancer, pancreatic cancer, breast cancer, bladder cancer, gastric cancer, esophagogastric junction adenocarcinoma, gastrointestinal stromal tumor, uterine cervix cancer, esophageal cancer, squamous cell carcinoma, peritoneal cancer, liver cancer, hepatocellular cancer, endometrial cancer, uterine cancer, salivary gland cancer, kidney cancer, vulval cancer, thyroid cancer, penis cancer, leukemia, malignant lymphoma, plasmacytoma, myeloma, neuroepithelial tissue tumor, nerve sheath tumor, head-and-neck cancer, skin cancer, pharyngeal cancer, gallbladder cancer, bile duct cancer, mesothelioma, Paget's disease, and sarcoma.

[93] An antibody-drug conjugate for treating a disease through being administered in combination with an immune checkpoint inhibitor, wherein a drug-linker represented by the following formula:

[Formula 7]

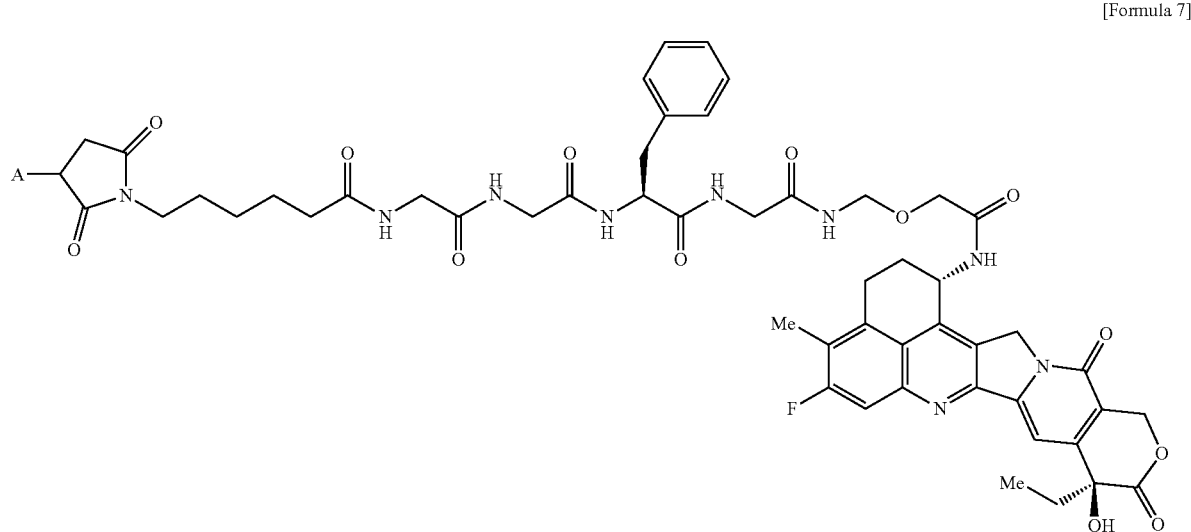

wherein A represents the connecting position to an antibody, is conjugated to the antibody via a thioether bond in the antibody-drug conjugate.

[94] The antibody-drug conjugate according to [93], wherein the antibody in the antibody-drug conjugate is an anti-HER2 antibody, an anti-HER3 antibody, an anti-TROP2 antibody, or an anti-B7-H3 antibody.

[95] The antibody-drug conjugate according to [94], wherein the antibody in the antibody-drug conjugate is an anti-HER2 antibody.

[96] The antibody-drug conjugate according to [94] or [95], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[97] The antibody-drug conjugate according to [94] or [95], wherein the anti-HER2 antibody is an antibody comprising a heavy chain consisting of the amino acid sequence represented by SEQ ID NO: 1 and a light chain consisting of the amino acid sequence represented by SEQ ID NO: 2.

[98] The antibody-drug conjugate according to any one of [93] to [97], wherein the average number of units of the drug-linker conjugated per antibody molecule in the antibody-drug conjugate is in the range of from 2 to 8.

[99] The antibody-drug conjugate according to any one of [93] to [97], wherein the average number of units of the drug-linker conjugated per antibody molecule in the antibody-drug conjugate is in the range of from 7 to 8.

[100] The antibody-drug conjugate according to any one of [93] to [97], wherein the average number of units of the drug-linker conjugated per antibody molecule in the antibody-drug conjugate is in the range of from 7.5 to 8.

[101] The antibody-drug conjugate according to any one of [93] to [100], wherein the immune checkpoint inhibitor is an anti-PD-1 antibody, an anti-PD-L1 antibody, or an anti-CTLA-4 antibody.

[102] The antibody-drug conjugate according to [101], wherein the immune checkpoint inhibitor is an anti-PD-1 antibody.

[103] The antibody-drug conjugate according to [101], wherein the immune checkpoint inhibitor is an anti-PD-L1 antibody.

[104] The antibody-drug conjugate according to [101], wherein the immune checkpoint inhibitor is an anti-CTLA-4 antibody.

[105] The antibody-drug conjugate according to any one of [93] to [104], wherein the antibody-drug conjugate and the immune checkpoint inhibitor are separately contained as active components in different formulations, and are administered simultaneously or at different times.

[106] The antibody-drug conjugate according to any one of [93] to [104], wherein the antibody-drug conjugate and the immune checkpoint inhibitor are contained as active components in a single formulation and administered.

[107] The antibody-drug conjugate according to any one of [93] to [106], wherein the antibody-drug conjugate is for treating cancer.

[108] The antibody-drug conjugate according to [107], wherein the cancer is at least one selected from the group consisting of lung cancer, urothelial cancer, colorectal cancer, prostate cancer, ovarian cancer, pancreatic cancer, breast cancer, bladder cancer, gastric cancer, esophagogastric junction adenocarcinoma, gastrointestinal stromal tumor, uterine cervix cancer, esophageal cancer, squamous cell carcinoma, peritoneal cancer, liver cancer, hepatocellular cancer, endometrial cancer, uterine cancer, salivary gland cancer, kidney cancer, vulval cancer, thyroid cancer, penis cancer, leukemia, malignant lymphoma, plasmacytoma, myeloma, neuroepithelial tissue tumor, nerve sheath tumor, head-and-neck cancer, skin cancer, pharyngeal cancer, gallbladder cancer, bile duct cancer, mesothelioma, Paget's disease, and sarcoma.

[109] The antibody-drug conjugate according to [108], wherein the cancer is colorectal cancer.

[110] The antibody-drug conjugate according to [108], wherein the cancer is breast cancer.

[111] The antibody-drug conjugate according to any one of [93] to [110], wherein the antibody-drug conjugate has an antitumor immunity-activating effect.

[112] The antibody-drug conjugate according to any one of [93] to [111], wherein the antibody-drug conjugate has at least one effect selected from the group consisting of:

(1) a promoting effect on growth of intratumor CD8-positive T cells; and (2) an activating effect on intratumor CD8-positive T cells.

[113] The antibody-drug conjugate according to any one of [93] to [112], wherein the antibody-drug conjugate has a promoting effect on the formation of immune memory against tumor.

[114] The antibody-drug conjugate according to [113], wherein the tumor is expressing an antigen for the antibody in the antibody-drug conjugate.

[115] The antibody-drug conjugate according to [113], wherein a part of the cells of the tumor are not expressing an antigen for the antibody in the antibody-drug conjugate.

[116] The antibody-drug conjugate according to any one of [93] to [115], wherein the antibody-drug conjugate has at least one effect selected from the group consisting of:

(1) a promoting effect on increase of the number of dendritic cells in a tumor;

(2) an activating effect on dendritic cells; and (3) a promoting effect on elevation of the expression level of MHC class I on cancer cells.

[117] The antibody-drug conjugate according to any one of [93] to [116], wherein the immune checkpoint inhibitor deactivates an immunosuppression signal generated through elevation of the expression level of PD-L1 on cancer cells promoted by the antibody-drug conjugate, and thereby the antibody-drug conjugate exhibits a higher antitumor effect.

[118] An antibody-drug conjugate for use in treatment of a disease that can be ameliorated through an antitumor immunity-activating effect, wherein a drug-linker represented by the following formula:

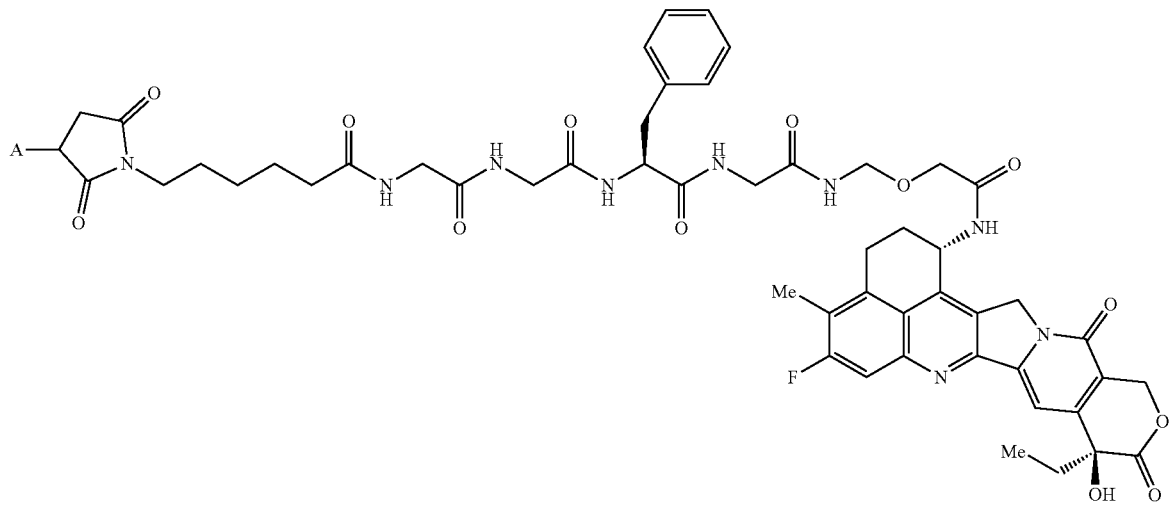

wherein A represents the connecting position to an antibody, is conjugated to the antibody via a thioether bond.

[119] The antibody-drug conjugate according to [118], wherein the antibody-drug conjugate has at least one effect selected from the group consisting of:

(1) a promoting effect on growth of intratumor CD8-positive T cells; and (2) an activating effect on intratumor CD8-positive T cells.

[120] The antibody-drug conjugate according to [118] or [119], wherein the antibody-drug conjugate has a promoting effect on the formation of immune memory against tumor.

[121] The antibody-drug conjugate according to [120], wherein the tumor is expressing an antigen for the antibody in the antibody-drug conjugate.

[122] The antibody-drug conjugate according to [120], wherein a part of the cells of the tumor are not expressing an antigen for the antibody in the antibody-drug conjugate.

[123] The antibody-drug conjugate according to any one of [118] to [122], for use in treatment of a disease that can be ameliorated through at least one effect selected from the group consisting of:

(1) a promoting effect on increase of the number of dendritic cells in a tumor;

(2) an activating effect on dendritic cells; and (3) a promoting effect on elevation of the expression level of MHC class I on cancer cells.

[124] The antibody-drug conjugate according to any one of [118] to [123], wherein the antibody in the antibody-drug conjugate is an anti-HER2 antibody, an anti-HER3 antibody, an anti-TROP2 antibody, or an anti-B7-H3 antibody.

[125] The antibody-drug conjugate according to [124], wherein the antibody in the antibody-drug conjugate is an anti-HER2 antibody.

[126] The antibody-drug conjugate according to [124] or [125], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[127] The antibody-drug conjugate according to [124] or [125], wherein the anti-HER2 antibody is an antibody comprising a heavy chain consisting of the amino acid sequence represented by SEQ ID NO: 1 and a light chain consisting of the amino acid sequence represented by SEQ ID NO: 2.

[128] The antibody-drug conjugate according to any one of [118] to [127], wherein the average number of units of the drug-linker conjugated per antibody molecule in the antibody-drug conjugate is in the range of from 2 to 8.

[129] The antibody-drug conjugate according to any one of [118] to [127], wherein the average number of units of the drug-linker conjugated per antibody molecule in the antibody-drug conjugate is in the range of from 7 to 8.

[130] The antibody-drug conjugate according to any one of [118] to [127], wherein the average number of units of the drug-linker conjugated per antibody molecule in the antibody-drug conjugate is in the range of from 7.5 to 8.

[131] The antibody-drug conjugate according to any one of [118] to [130], wherein the disease is at least one selected from the group consisting of lung cancer, urothelial cancer, colorectal cancer, prostate cancer, ovarian cancer, pancreatic cancer, breast cancer, bladder cancer, gastric cancer, esophagogastric junction adenocarcinoma, gastrointestinal stromal tumor, uterine cervix cancer, esophageal cancer, squamous cell carcinoma, peritoneal cancer, liver cancer, hepatocellular cancer, endometrial cancer, uterine cancer, salivary gland cancer, kidney cancer, vulval cancer, thyroid cancer, penis cancer, leukemia, malignant lymphoma, plasmacytoma, myeloma, neuroepithelial tissue tumor, nerve sheath tumor, head-and-neck cancer, skin cancer, pharyngeal cancer, gallbladder cancer, bile duct cancer, mesothelioma, Paget's disease, and sarcoma.

[132] The antibody-drug conjugate according to [131], wherein the disease is colorectal cancer.

[133] The antibody-drug conjugate according to [131], wherein the disease is breast cancer.

[134] A compound for use in treatment of a disease that can be ameliorated through an antitumor immunity-activating effect, wherein the compound is represented by the following formula:

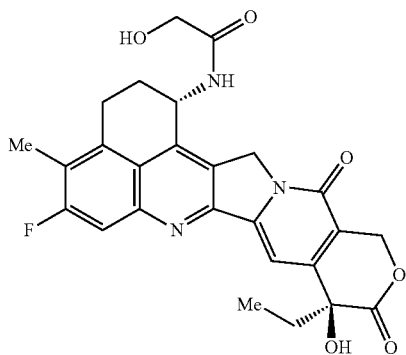

[Formula 9]

and released in a tumor.

The compound according to [134], wherein the compound has at least one effect selected from the group consisting of:

(1) a promoting effect on growth of intratumor CD8-positive T cells; and (2) an activating effect on intratumor CD8-positive T cells.

[136] The compound according to [134] or [135], wherein the compound has a promoting effect on the formation of immune memory against tumor.

[137] The compound according to any one of [134] to [136], wherein the compound has at least one effect selected from the group consisting of:

(1) a promoting effect on increase of the number of dendritic cells in a tumor;

(2) an activating effect on dendritic cells; and (3) a promoting effect on elevation of the expression level of MHC class I on cancer cells.

[138] The compound according to any one of [134] to [137], wherein the disease is at least one selected from the group consisting of lung cancer, urothelial cancer, colorectal cancer, prostate cancer, ovarian cancer, pancreatic cancer, breast cancer, bladder cancer, gastric cancer, esophagogastric junction adenocarcinoma, gastrointestinal stromal tumor, uterine cervix cancer, esophageal cancer, squamous cell carcinoma, peritoneal cancer, liver cancer, hepatocellular cancer, endometrial cancer, uterine cancer, salivary gland cancer, kidney cancer, vulval cancer, thyroid cancer, penis cancer, leukemia, malignant lymphoma, plasmacytoma, myeloma, neuroepithelial tissue tumor, nerve sheath tumor, head-and-neck cancer, skin cancer, pharyngeal cancer, gallbladder cancer, bile duct cancer, mesothelioma, Paget's disease, and sarcoma.

[139] Use of an antibody-drug conjugate for production of a medicine for treating a disease through being administered in combination with an immune checkpoint inhibitor, wherein a drug-linker represented by the following formula:

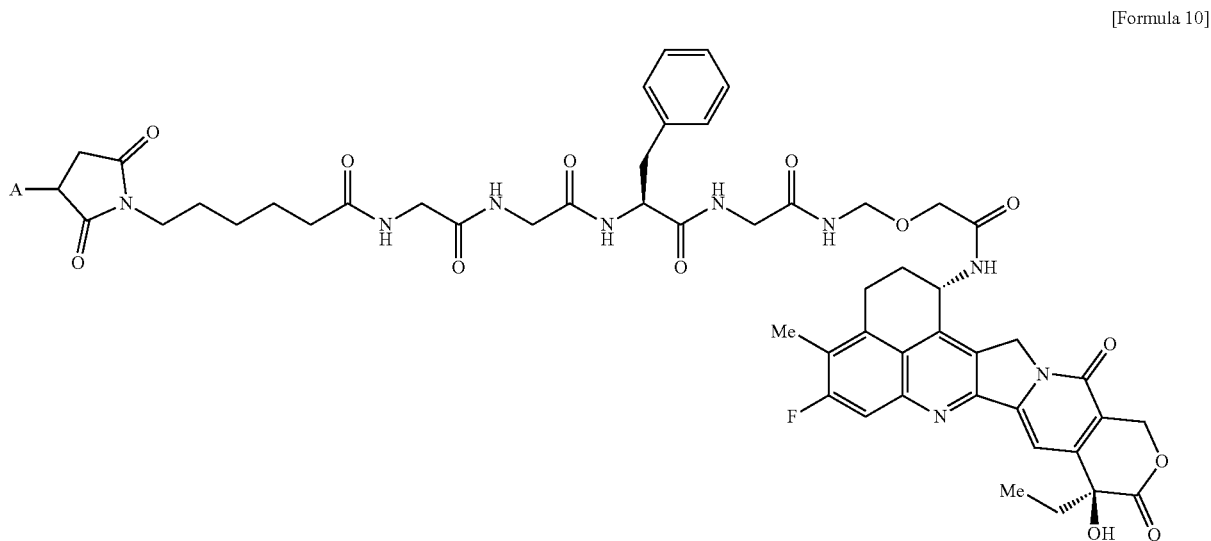

[Formula 10]

wherein A represents the connecting position to an antibody, is conjugated to the antibody via a thioether bond in the antibody-drug conjugate.

[140] The use according to [139], wherein the antibody in the antibody-drug conjugate is an anti-HER2 antibody, an anti-HER3 antibody, an anti-TROP2 antibody, or an anti-B7-H3 antibody.

[141] The use according to [140], wherein the antibody in the antibody-drug conjugate is an anti-HER2 antibody.

[142] The use according to [140] or [141], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[143] The use according to [140] or [141], wherein the anti-HER2 antibody is an antibody comprising a heavy chain consisting of the amino acid sequence represented by SEQ ID NO: 1 and a light chain consisting of the amino acid sequence represented by SEQ ID NO: 2.

[144] The use according to any one of [139] to [143], wherein the average number of units of the drug-linker conjugated per antibody molecule in the antibody-drug conjugate is in the range of from 2 to 8.

[145] The use according to any one of [139] to [143], wherein the average number of units of the drug-linker conjugated per antibody molecule in the antibody-drug conjugate is in the range of from 7 to 8.

[146] The use according to any one of [139] to [143], wherein the average number of units of the drug-linker conjugated per antibody molecule in the antibody-drug conjugate is in the range of from 7.5 to 8.

[147] The use according to any one of [139] to [146], wherein the immune checkpoint inhibitor is an anti-PD-1 antibody, an anti-PD-L1 antibody, or an anti-CTLA-4 antibody.

[148] The use according to [147], wherein the immune checkpoint inhibitor is an anti-PD-1 antibody.

[149] The use according to [147], wherein the immune checkpoint inhibitor is an anti-PD-L1 antibody.

[150] The use according to [147], wherein the immune checkpoint inhibitor is an anti-CTLA-4 antibody.

[151] The use according to any one of [139] to [150], wherein the antibody-drug conjugate and the immune checkpoint inhibitor are separately contained as active components in different formulations, and are administered simultaneously or at different times.

[152] The use according to any one of [139] to [150], wherein the antibody-drug conjugate and the immune checkpoint inhibitor are contained as active components in a single formulation and administered.

[153] The use according to any one of [139] to [152], wherein the use is for treating cancer.

[154] The use according to [153], wherein the cancer is at least one selected from the group consisting of lung cancer, urothelial cancer, colorectal cancer, prostate cancer, ovarian cancer, pancreatic cancer, breast cancer, bladder cancer, gastric cancer, esophagogastric junction adenocarcinoma, gastrointestinal stromal tumor, uterine cervix cancer, esophageal cancer, squamous cell carcinoma, peritoneal cancer, liver cancer, hepatocellular cancer, endometrial cancer, uterine cancer, salivary gland cancer, kidney cancer, vulval cancer, thyroid cancer, penis cancer, leukemia, malignant lymphoma, plasmacytoma, myeloma, neuroepithelial tissue tumor, nerve sheath tumor, head-and-neck cancer, skin cancer, pharyngeal cancer, gallbladder cancer, bile duct cancer, mesothelioma, Paget's disease, and sarcoma.

[155] The use according to [154], wherein the cancer is colorectal cancer.

[156] The use according to [154], wherein the cancer is breast cancer.

[157] The use according to any one of [139] to [156], wherein the antibody-drug conjugate has an antitumor immunity-activating effect.

[158] The use according to any one of [139] to [157], wherein the antibody-drug conjugate has at least one effect selected from the group consisting of:

(1) a promoting effect on growth of intratumor CD8-positive T cells; and (2) an activating effect on intratumor CD8-positive T cells.

[159] The use according to any one of [139] to [158], wherein the antibody-drug conjugate has a promoting effect on the formation of immune memory against tumor.

[160] The use according to [159], wherein the tumor is expressing an antigen for the antibody in the antibody-drug conjugate.

[161] The use according to [159], wherein a part of the cells of the tumor are not expressing an antigen for the antibody in the antibody-drug conjugate.

[162] The use according to any one of [139] to [161], wherein the antibody-drug conjugate has at least one effect selected from the group consisting of:

(1) a promoting effect on increase of the number of dendritic cells in a tumor;

(2) an activating effect on dendritic cells; and (3) a promoting effect on elevation of the expression level of MHC class I on cancer cells.

[163] The use according to any one of [139] to [162], wherein the immune checkpoint inhibitor deactivates an immunosuppression signal generated through elevation of the expression level of PD-L1 on cancer cells promoted by the antibody-drug conjugate, and thereby the antibody-drug conjugate exhibits a higher antitumor effect.

[164] Use of an antibody-drug conjugate for production of a medicine for use in treatment of a disease that can be ameliorated through an antitumor immunity-activating effect, wherein a drug-linker represented by the following formula:

[Formula 11]

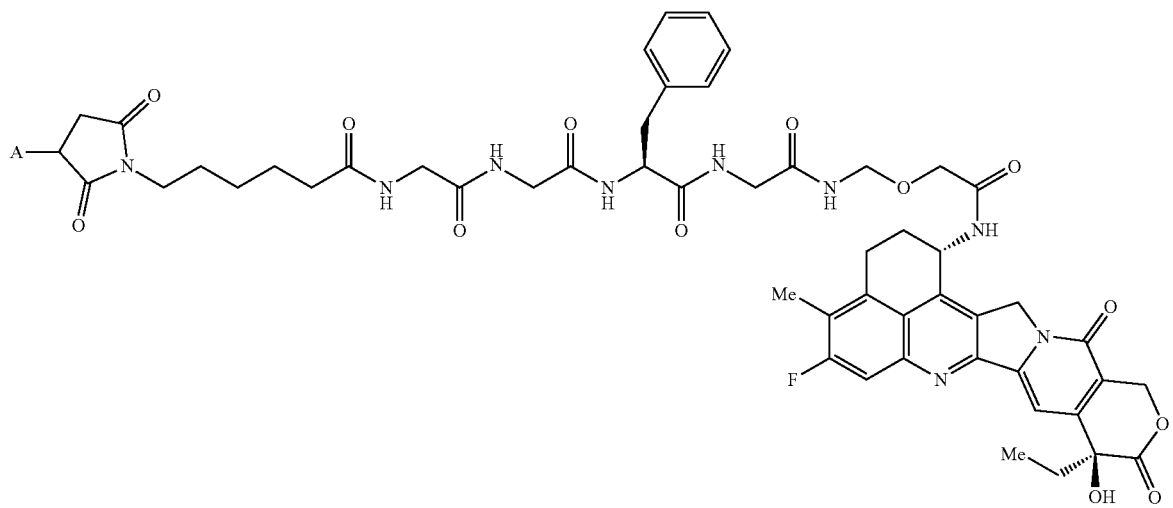

wherein A represents the connecting position to an antibody, is conjugated to the antibody via a thioether bond in the antibody-drug conjugate.

[165] The use according to [164], wherein the antibody-drug conjugate has at least one effect selected from the group consisting of:

(1) a promoting effect on growth of intratumor CD8-positive T cells; and (2) an activating effect on intratumor CD8-positive T cells.

[166] The use according to [164] or [165], wherein the antibody-drug conjugate has a promoting effect on the formation of immune memory against tumor.

[167] The use according to [166], wherein the tumor is expressing an antigen for the antibody in the antibody-drug conjugate.

[168] The use according to [166], wherein a part of the cells of the tumor are not expressing an antigen for the antibody in the antibody-drug conjugate.

[169] The use according to any one of [164] to [168], wherein the use is for production of a medicine for use in treatment of a disease that can be ameliorated through at least one effect selected from the group consisting of:

(1) a promoting effect on increase of the number of dendritic cells in a tumor;

(2) an activating effect on dendritic cells; and (3) a promoting effect on elevation of the expression level of MHC class I on cancer cells.

[170] The use according to any one of [164] to [169], wherein the antibody in the antibody-drug conjugate is an anti-HER2 antibody, an anti-HER3 antibody, an anti-TROP2 antibody, or an anti-B7-H3 antibody.

[171] The use according to [170], wherein the antibody in the antibody-drug conjugate is an anti-HER2 antibody.

[172] The use according to [170] or [171], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[173] The use according to [170] or [171], wherein the anti-HER2 antibody is an antibody comprising a heavy chain consisting of the amino acid sequence represented by SEQ ID NO: 1 and a light chain consisting of the amino acid sequence represented by SEQ ID NO: 2.

[174] The use according to any one of [164] to [173], wherein the average number of units of the drug-linker conjugated per antibody molecule in the antibody-drug conjugate is in the range of from 2 to 8.

[175] The use according to any one of [164] to [173], wherein the average number of units of the drug-linker conjugated per antibody molecule in the antibody-drug conjugate is in the range of from 7 to 8.

[176] The use according to any one of [164] to [173], wherein the average number of units of the drug-linker conjugated per antibody molecule in the antibody-drug conjugate is in the range of from 7.5 to 8.

[177] The use according to any one of [164] to [176], wherein the disease is at least one selected from the group consisting of lung cancer, urothelial cancer, colorectal cancer, prostate cancer, ovarian cancer, pancreatic cancer, breast cancer, bladder cancer, gastric cancer, esophagogastric junction adenocarcinoma, gastrointestinal stromal tumor, uterine cervix cancer, esophageal cancer, squamous cell carcinoma, peritoneal cancer, liver cancer, hepatocellular cancer, endometrial cancer, uterine cancer, salivary gland cancer, kidney cancer, vulval cancer, thyroid cancer, penis cancer, leukemia, malignant lymphoma, plasmacytoma, myeloma, neuroepithelial tissue tumor, nerve sheath tumor, head-and-neck cancer, skin cancer, pharyngeal cancer, gallbladder cancer, bile duct cancer, mesothelioma, Paget's disease, and sarcoma.

[178] The use according to [177], wherein the disease is colorectal cancer.

[179] The use according to [177], wherein the disease is breast cancer.

[180] Use of a compound for production of a medicine for use in treatment of a disease that can be ameliorated through an antitumor immunity-activating effect, wherein the compound is represented by the following formula:

[Formula 12]

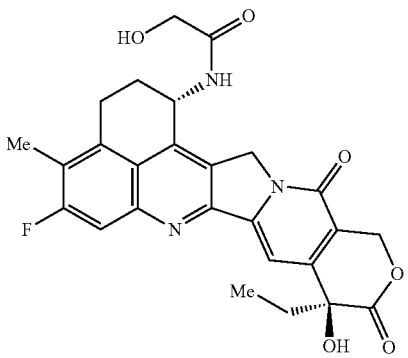

and released in a tumor.

[181] The use according to [180], wherein the compound has at least one effect selected from the group consisting of:
 (1) a promoting effect on growth of intratumor CD8-positive T cells; and
 (2) an activating effect on intratumor CD8-positive T cells.

[182] The use according to [180] or [181], wherein the compound has a promoting effect on the formation of immune memory against tumor.

[183] The use according to any one of [180] to [182], wherein the compound has at least one effect selected from the group consisting of:
 (1) a promoting effect on increase of the number of dendritic cells in a tumor;
 (2) an activating effect on dendritic cells; and
 (3) a promoting effect on elevation of the expression level of MHC class I on cancer cells.

[184] The use according to any one of [180] to [183], wherein the disease is at least one selected from the group consisting of lung cancer, urothelial cancer, colorectal cancer, prostate cancer, ovarian cancer, pancreatic cancer, breast cancer, bladder cancer, gastric cancer, esophagogastric junction adenocarcinoma, gastrointestinal stromal tumor, uterine cervix cancer, esophageal cancer, squamous cell carcinoma, peritoneal cancer, liver cancer, hepatocellular cancer, endometrial cancer, uterine cancer, salivary gland cancer, kidney cancer, vulval cancer, thyroid cancer, penis cancer, leukemia, malignant lymphoma, plasmacytoma, myeloma, neuroepithelial tissue tumor, nerve sheath tumor, head-and-neck cancer, skin cancer, pharyngeal cancer, gallbladder cancer, bile duct cancer, mesothelioma, Paget's disease, and sarcoma.

Advantageous Effects of Invention

The present invention can provide a pharmaceutical composition and a therapeutic method which exert a particularly superior antitumor effect and safety through administering a specific antibody-drug conjugate and an immune checkpoint inhibitor in combination. In addition, the present invention can provide a pharmaceutical composition and a therapeutic method for treating a disease that can be ameliorated through a promoting effect on the formation of immune memory against tumor wherein a specific antibody-drug conjugate is included.

BRIEF DESCRIPTION OF DRAWINGS

FIG. 1 shows an amino acid sequence of a heavy chain of a humanized anti-HER2 antibody (SEQ ID NO: 1).

FIG. 2 shows an amino acid sequence of a light chain of a humanized anti-HER2 antibody (SEQ ID NO: 2).

FIG. 3 is a diagram showing life-prolonging effects of different agents on mice with subcutaneously transplanted CT26.WT-hHER2 cells. Comparison was made on life-prolonging effect between a single administration group with each of an antibody-drug conjugate (1) and an anti-PD-1 antibody (clone RMP1-14) and a combined administration group.

FIG. 4 is a diagram showing life-prolonging effects of different agents on mice with subcutaneously transplanted CT26.WT-hHER2 cells. Comparison was made on life-prolonging effect between a single administration group with each of an antibody-drug conjugate (1) and an anti-PD-1 antibody (clone RMP1-14) and a combined administration group.

FIG. 5 is a diagram showing transition of tumor volume in antibody-drug conjugate (1)-treated cured mice and control mice with subcutaneously transplanted (retransplanted) CT26.WT-hHER2 cells or CT26.WT-mock cells.

FIG. 6 is a diagram showing immune response to an antigen derived from CT26.WT-hHER2 cells (the number of IFNγ-producing splenocytes) in antibody-drug conjugate (1)-treated cured mice and control mice with subcutaneously transplanted (retransplanted) CT26.WT-hHER2 cells.

FIG. 7 is a diagram showing immune response to an antigen derived from CT26.WT-mock cells (the number of IFNγ-producing splenocytes) in antibody-drug conjugate (1)-treated cured mice and control mice with subcutaneously transplanted (retransplanted) CT26.WT-hHER2 cells.

FIG. 8 is a diagram showing immune response to an antigen derived from CT26.WT-hHER2 cells (the number of IFNγ-producing splenocytes) in antibody-drug conjugate (1)-treated cured mice and control mice with subcutaneously transplanted (retransplanted) CT26.WT-mock cells.

FIG. 9 is a diagram showing immune response to an antigen derived from CT26.WT-mock cells (the number of IFNγ-producing splenocytes) in antibody-drug conjugate (1)-treated cured mice and control mice with subcutaneously transplanted (retransplanted) CT26.WT-mock cells.

FIG. 10 is a series of diagrams showing expression levels of CD86 in bone marrow-derived dendritic cells treated with a compound (A) and those treated with DMSO as determined with flow cytometry.

FIG. 11 is a series of diagrams showing expression levels of MHC class II in bone marrow-derived dendritic cells treated with a compound (A) and those treated with DMSO as determined with flow cytometry.

FIG. 12 is a diagram showing the number of dendritic cells among intratumor lymphocytes as determined with flow cytometry for an antibody-drug conjugate (1)-administered group of mice with subcutaneously transplanted CT26.WT-hHER2 cells and a control group thereof.

FIG. 13 is a diagram showing the number of CD86-positive cells among intratumor dendritic cells as determined with flow cytometry for an antibody-drug conjugate (1)-administered group of mice with subcutaneously transplanted CT26.WT-hHER2 cells and a control group thereof.

FIG. 14 is a diagram showing expression levels of CD86 on intratumor dendritic cells as determined with flow cytometry and expressed as MFI for an antibody-drug conjugate (1)-administered group of mice with subcutaneously transplanted CT26.WT-hHER2 cells and a control group thereof.

FIG. 15 is a diagram showing expression levels of MHC class I on cancer cells (human HER2-positive cells) as determined with flow cytometry and expressed as MFI for an antibody-drug conjugate (1)-administered group of mice with subcutaneously transplanted CT26.WT-hHER2 cells and a control group thereof.

FIG. 16 is a diagram showing expression levels of PD-L1 on cancer cells (human HER2-positive cells) as determined with flow cytometry and expressed as MFI for an antibody-drug conjugate (1)-administered group of mice with subcutaneously transplanted CT26.WT-hHER2 cells and a control group thereof.

FIG. 17 is a diagram showing expression levels of MHC class I as determined with flow cytometry for cancer cells treated with a compound (A) and those treated with DMSO.

FIG. 18 is a diagram showing transition of tumor volume for an antibody-drug conjugate (1)-administered group of mouse models of nude mice with subcutaneously transplanted CT26.WT-hHER2 cells and a control group thereof.

FIG. 19 is a diagram showing transition of tumor volume for an antibody-drug conjugate (1)-administered group of mice with subcutaneously transplanted CT26.WT-hHER2 cells, a control antibody-drug conjugate-administered group thereof, and a control group thereof.

FIG. 20 is a diagram showing transition of tumor volume for single administration groups of mice with subcutaneously transplanted EMT6-hHER2 cells with each of an antibody-drug conjugate (1) and an anti-PD-1 antibody (clone RMP1-14), and a combined administration group thereof.

FIG. 21 is a diagram showing life-prolonging effects of different agents on mice with subcutaneously transplanted CT26.WT-hHER2 cells. Comparison was made on life-prolonging effect between a single administration group with each of an antibody-drug conjugate (1) and an anti-PD-L1 antibody (clone 10F.9G2) and a combined administration group.

FIG. 22 is a diagram showing life-prolonging effects of different agents on mice with subcutaneously transplanted EMT6-hHER2 cells. Comparison was made on life-prolonging effect between a single administration group with each of an antibody-drug conjugate (1) and an anti-PD-L1 antibody (clone 10F.9G2) and a combined administration group.

FIG. 23 is a diagram showing transition of tumor volume for single administration groups of mice with subcutaneously transplanted CT26.WT-hHER2 cells with each of an antibody-drug conjugate (1) and an anti-CD4 antibody, and a combined administration group thereof.

FIG. 24 is a diagram showing transition of tumor volume for single administration groups of mice with subcutaneously transplanted CT26.WT-hHER2 cells with each of an antibody-drug conjugate (1) and an anti-CD8 antibody, and a combined administration group thereof.

FIG. 25 is a diagram showing the fraction of CD8-positive T cells among intratumor living cells as determined with flow cytometry for an antibody-drug conjugate (1)-administered group of mice with subcutaneously transplanted CT26.WT-hHER2 cells and a control group thereof.

FIG. 26 is a diagram showing the fraction of Granzyme B-positive cells among intratumor CD8-positive T cells as determined with flow cytometry for an antibody-drug conjugate (1)-administered group of mice with subcutaneously transplanted CT26.WT-hHER2 cells and a control group thereof.

FIG. 27 is a diagram showing the fraction of CD8-positive T cells being Granzyme B-positive among intratumor living cells as determined with flow cytometry for an antibody-drug conjugate (1)-administered group of mice with subcutaneously transplanted CT26.WT-hHER2 cells and a control group thereof.

FIG. 28 is a diagram showing the fraction of CD4-positive T cells among intratumor living cells as determined with flow cytometry for an antibody-drug conjugate (1)-administered group of mice with subcutaneously transplanted CT26.WT-hHER2 cells and a control group thereof.

FIG. 29 is a series of images of excised tumors stained with an anti-CD8 antibody for an antibody-drug conjugate (1)-administered group of mice with subcutaneously transplanted CT26.WT-hHER2 cells and a control group thereof.

FIG. 30 is a diagram showing the number of CD8-positive cells per unit area in tumors for an antibody-drug conjugate (1)-administered group of mice with subcutaneously transplanted CT26.WT-hHER2 cells and a control group thereof, as counted through analysis of images of excised tumors stained with an anti-CD8 antibody.

FIG. 31 is a diagram showing expression levels of MHC class I as determined with flow cytometry for cancer cells treated with a compound (A), those treated with DM1-SMe, those treated with DM4-SMe, those treated with MMAE, and those treated with DMSO.

FIG. 32 is a diagram showing transition of tumor volume for single administration groups of mice with subcutaneously transplanted EMT6-hHER2 cells with each of an antibody-drug conjugate (1) and an anti-CTLA-4 antibody (clone 9H10), and a combined administration group thereof.

DESCRIPTION OF EMBODIMENTS

Hereinafter, preferred modes for carrying out the present invention are described with reference to the drawings. The embodiments described below are given merely for illustrating one example of a typical embodiment of the present invention and are not intended to limit the scope of the present invention.

[Antibody-Drug Conjugate]

The antibody-drug conjugate used in the present invention is an antibody-drug conjugate in which a drug-linker represented by the following formula:

[Formula 13]

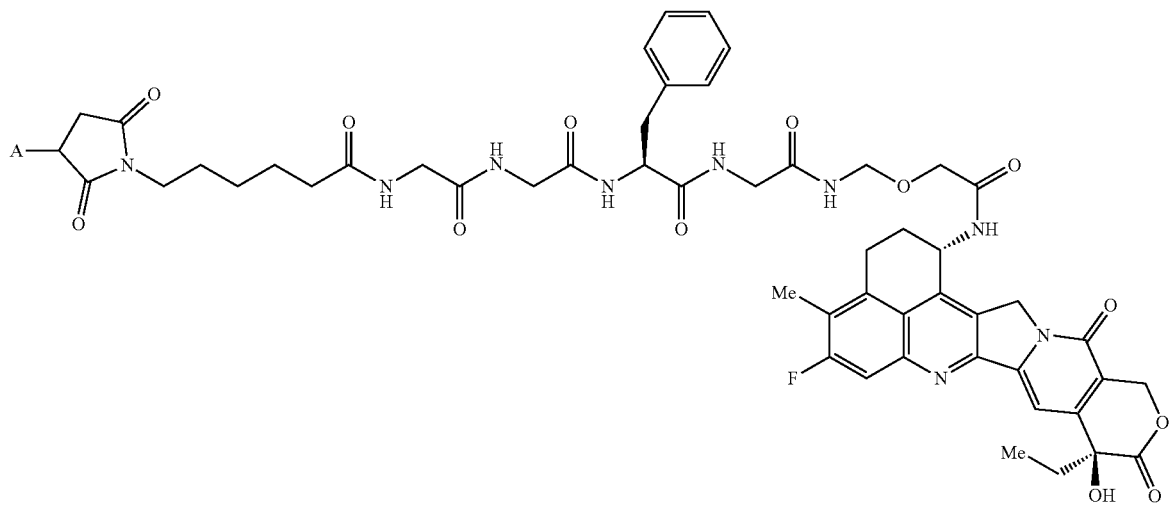

wherein A represents the connecting position to an antibody, is conjugated to the antibody via a thioether bond.

In the present invention, the partial structure consisting of a linker and a drug in the antibody-drug conjugate is referred to as a "drug-linker". The drug-linker is connected to a thiol group (in other words, the sulfur atom of a cysteine residue) formed at an interchain disulfide bond site (two sites between heavy chains, and two sites between a heavy chain and a light chain).

The drug-linker of the present invention includes exatecan (IUPAC name: (1S,9S)-1-amino-9-ethyl-5-fluoro-1,2,3,9,12,15-hexahydro-9-hydroxy-4-methyl-10H,13H-benzo[de]pyrano[3',4':6,7]indolizino[1,2-b]quinolin-10,13-dione, (also expressed as chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinolin-10,13(9H,15H)-dione)), which is a topoisomerase I inhibitor, as a component. Exatecan is a camptothecin derivative having an antitumor effect, represented by the following formula:

[Formula 14]

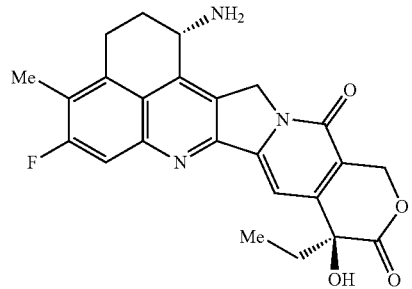

The antibody-drug conjugate used in the present invention can be also represented by the following formula.

[Formula 15]

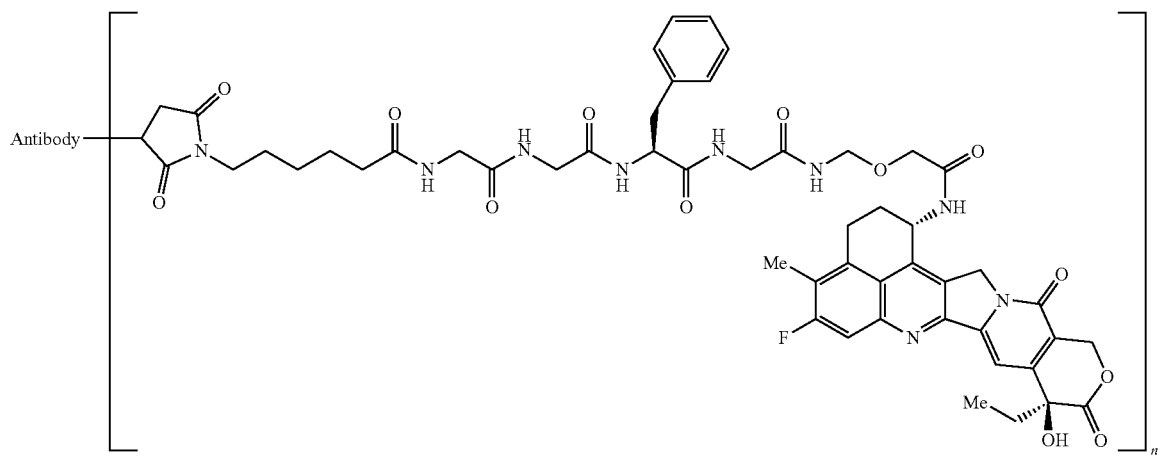

Here, the drug-linker is conjugated to an antibody via a thioether bond. The meaning of n is the same as that of what is called the average number of conjugated drug molecules (DAR; Drug-to-Antibody Ratio), and indicates the average number of units of the drug-linker conjugated per antibody molecule.

The antibody-drug conjugate used in the present invention has an antitumor immunity-activating effect.

In the present invention, the term "antitumor immunity-activating" refers to a property of promoting exertion of an antitumor effect by activating at least one selected from the group consisting of T cells and B cells (Bracci L. et al., Cell Death Differ. (2014) 21, 15-25, Chen D S. Et al., Immunity (2013) 39, 1-10, Andersen M H. et al., Journal of Investigative Dermatology (2006) 126, 32-41).

The situation that the antibody-drug conjugate used in the present invention is promoting exertion of an antitumor effect by activating at least one selected from the group consisting of T cells and B cells can be confirmed through comparison for the antibody-drug conjugate used in the present invention between an antitumor effect in mice with normal immune functions and that in mice with immune functions of T cells and B cells impaired (nude mice).

The antibody-drug conjugate used in the present invention has at least one effect selected from the group consisting of:

(1) a promoting effect on growth of intratumor CD8-positive T cells; and (2) an activating effect on intratumor CD8-positive T cells.

The "promoting effect on growth of intratumor CD8-positive T cells" possessed by the antibody-drug conjugate used in the present invention can be confirmed, for example, by determining the fraction of CD45-, CD3-, CD8-positive cells (CD8-positive T cells) among living cells with flow cytometry to examine the increase rate for an antibody-drug conjugate-administered group of cancer-bearing mice and a control group thereof. Alternatively, the effect can be confirmed by analyzing images of an excised tumor stained with an anti-CD8 antibody and counting the number of CD8-positive cells per unit area in the tumor to examine the increase rate for an antibody-drug conjugate-administered group of cancer-bearing mice and a control group thereof.

The "activating effect on intratumor CD8-positive T cells" possessed by the antibody-drug conjugate used in the present invention can be confirmed, for example, by determining the fraction of Granzyme B-positive cells among CD8-positive T cells with flow cytometry to examine the increase rate for an antibody-drug conjugate-administered group of cancer-bearing mice and a control group thereof. Alternatively, the effect can be confirmed by determining the fraction of Granzyme B-positive cells among living cells with flow cytometry to examine the increase rate.

The antibody-drug conjugate used in the present invention has a promoting effect on the formation of immune memory against tumor. This effect contributes to the above-described "antitumor immunity-activating effect".

On being presented with a tumor-derived antigen from dendritic cells or cancer cells, T cells are activated to cause an immune response, exerting an antitumor effect.

In the present invention, the phrase "formation of immune memory against tumor" refers to the phenomenon that T cells presented with a tumor-derived antigen generate memory T cells therefrom and thereby memory of an immune response against the antigen is formed. The phenomenon allows exertion of a sustained antitumor effect against tumor having the antigen, and further allows exertion of an antitumor effect again on the recurrence of tumor having the antigen.

The "promoting effect on the formation of immune memory against tumor" possessed by the antibody-drug conjugate used in the present invention can be confirmed, for example, by administering the antibody-drug conjugate to cancer-bearing mice and retransplanting tumor to mice which have undergone complete tumor regression to determine the tumor proliferation (regression)-suppressing rate. Alternatively, the effect can be confirmed by excising the spleen from each of the mice and adding a tumor-derived antigen to the spleen to determine the increase rate of an immune response (e.g., the number of IFNγ-producing splenocytes).

The antibody-drug conjugate used in the present invention has a promoting effect on the formation of immune memory not only against tumor expressing an antigen for the antibody in the antibody-drug conjugate, but also against tumor not expressing the antigen for the antibody in the antibody-drug conjugate in the same individual.

In the case that the antibody in the antibody-drug conjugate is an anti-HER2 antibody, for example, the antibody-drug conjugate used in the present invention not only has a promoting effect on the formation of immune memory against tumor expressing HER2, but also has a promoting effect on the formation of immune memory against tumor not expressing HER2 in the same individual.

In addition, the antibody-drug conjugate used in the present invention has at least one effect selected from the group consisting of:

(1) a promoting effect on increase of the number of dendritic cells in a tumor;

(2) an activating effect on dendritic cells; and (3) a promoting effect on elevation of the expression level of MHC class I on cancer cells.

These effects contribute to the above-described "promoting effect on the formation of immune memory against tumor", and eventually contribute to the above-described "antitumor immunity-activating effect".

The "promoting effect on increase of the number of dendritic cells in a tumor" possessed by the antibody-drug conjugate used in the present invention can be confirmed, for example, by determining the fraction of CD11c-, MHC class II-, CD45-positive cells (dendritic cells, DCs) among CD45-positive cells (lymphocytic cells) with flow cytometry to examine the increase rate for an antibody-drug conjugate-administered group of cancer-bearing mice and a control group thereof.

The "activating effect on dendritic cells" possessed by the antibody-drug conjugate used in the present invention can be confirmed, for example, by determining the fraction of dendritic cells expressing CD86 (activation marker) with flow cytometry to examine the increase rate for an antibody-drug conjugate-administered group of cancer-bearing mice and a control group thereof. Alternatively, the effect can be confirmed by determining the expression level (MFI (mean fluorescence intensity)) of CD86 on dendritic cells with flow cytometry to examine the increase rate for an antibody-drug conjugate-administered group of cancer-bearing mice and a control group thereof.

The "promoting effect on elevation of the expression level of MHC class I on cancer cells" possessed by the antibody-drug conjugate used in the present invention can be confirmed, for example, by determining the expression level (MFI) of MHC class I on cancer cells with flow cytometry to examine the increase rate for an antibody-drug conjugate-administered group of cancer-bearing mice and a control group thereof.

The antibody-drug conjugate used in the present invention occasionally has a promoting effect on elevation of the expression level of PD-L1 on cancer cells. Immune checkpoint inhibitors deactivate an immunosuppressive signal generated through the effect, and thereby the antibody-drug conjugate can exhibit a higher antitumor effect. Accordingly, the antibody-drug conjugate used in the present invention is expected to exhibit a higher antitumor effect if being used in combination with an immune checkpoint inhibitor.

The "promoting effect on elevation of the expression level of PD-L1 on cancer cells" possessed by the antibody-drug conjugate used in the present invention can be confirmed, for example, by determining the expression level (MFI) of PD-L1 on cancer cells with flow cytometry to examine the increase rate for an antibody-drug conjugate-administered group of cancer-bearing mice and a control group thereof.

After migrating into cancer cells, the antibody-drug conjugate used in the present invention is cleaved at the linker portion to release a compound represented by the following formula:

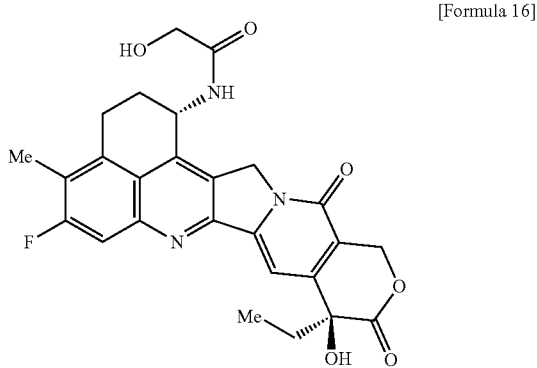 [SMILES: CC[C@@]1(O)C(=O)OCc2c1cc1n(c2=O)Cc2c-1nc1cc(F)c(C)c3c1c2[C@@H](NC(=O)CO)CC3]

[Formula 16]

(hereinafter, referred to as the "compound (A)").

The compound (A) is inferred to be the original source of the antitumor activity of the antibody-drug conjugate used in the present invention, and has been confirmed to have a topoisomerase I inhibitory effect (Ogitani Y. et al., Clinical Cancer Research, 2016, Oct. 15; 22(20):5097-5108, Epub 2016 Mar. 29).

The compound (A) has an activating effect on dendritic cells and a promoting effect on elevation of the expression level of MHC class I on cancer cells.

The "activating effect on dendritic cells" possessed by the compound (A) can be confirmed, for example, by determining the expression level of CD86 with flow cytometry to examine the increase rate for bone marrow-derived dendritic cells treated with the compound (A) and those treated with DMSO.

The "promoting effect on elevation of the expression level of MHC class I on cancer cells" possessed by the compound (A) can be confirmed, for example, by determining the expression level of MHC class I with flow cytometry to examine the increase rate for cancer cells treated with the compound (A) and those treated with DMSO.

The "activating effect on dendritic cells" and "promoting effect on elevation of the expression level of MHC class I on cancer cells" possessed by the compound (A) are effects associated with the "activating effect on dendritic cells" and "promoting effect on elevation of the expression level of MHC class I on cancer cells" possessed by the antibody-drug conjugate used in the present invention. As described above, the compound (A) is a compound which is released from the antibody-drug conjugate used in the present invention after the antibody-drug conjugate used in the present invention migrates into cancer cells.

Accordingly, pharmaceutical compositions which release the compound (A) in a tumor are expected to have at least one effect selected from the group consisting of:
(1) a promoting effect on increase of the number of dendritic cells in a tumor;
(2) an activating effect on dendritic cells; and
(3) a promoting effect on elevation of the expression level of MHC class I on cancer cells, as the antibody-drug conjugate used in the present invention.

Further, pharmaceutical compositions which release the compound (A) in a tumor are expected to have a promoting effect on the formation of immune memory against tumor, as the antibody-drug conjugate used in the present invention.

As described above, the compound (A) is a compound which is generated from the antibody-drug conjugate used in the present invention after the antibody-drug conjugate used in the present invention migrates into cancer cells.

Accordingly, pharmaceutical compositions which release the compound (A) in a tumor are expected to have at least one effect selected from the group consisting of:
(1) a promoting effect on growth of intratumor CD8-positive T cells; and
(2) an activating effect on intratumor CD8-positive T cells,
as the antibody-drug conjugate used in the present invention, and in addition are expected to have an "antitumor immunity-activating effect".

The antibody-drug conjugate used in the present invention is known to have a bystander effect (Ogitani Y. et al., Cancer Science (2016) 107, 1039-1046).

The bystander effect is exerted through a process such that the antibody-drug conjugate used in the present invention is internalized in cancer cells expressing a target and the compound (A) released then exerts an antitumor effect also on cancer cells which are present therearound and not expressing the target.

The bystander effect possessed by the antibody-drug conjugate used in the present invention is exerted as an excellent antitumor effect even when using in combination with an immune checkpoint inhibitor.

[Antibody for Use in Production of Antibody-Drug Conjugate]

The antibody for use in production of the antibody-drug conjugate according to the present invention may be derived from any species, and is preferably an antibody derived from a human, a rat, a mouse, or a rabbit. In cases when the antibody is derived from species other than human species, it is preferably chimerized or humanized using a well known technique. The antibody of the present invention may be a polyclonal antibody or a monoclonal antibody and is preferably a monoclonal antibody.

The antibody for use in production of the antibody-drug conjugate according to the present invention is an antibody preferably having a characteristic of being capable of targeting cancer cells, and is preferably an antibody possessing, for example, a property of recognizing a cancer cell, a property of binding to a cancer cell, a property of internalizing in a cancer cell, and/or cytocidal activity against cancer cells.

The binding activity of the antibody against cancer cells can be confirmed using flow cytometry. The internalization of the antibody into tumor cells can be confirmed using (1) an assay of visualizing an antibody incorporated in cells under a fluorescence microscope using a secondary antibody (fluorescently labeled) binding to the therapeutic antibody (Cell Death and Differentiation (2008) 15, 751-761), (2) an assay of measuring a fluorescence intensity incorporated in cells using a secondary antibody (fluorescently labeled) binding to the therapeutic antibody (Molecular Biology of the Cell, Vol. 15, 5268-5282, December 2004), or (3) a Mab-ZAP assay using an immunotoxin binding to the therapeutic antibody wherein the toxin is released upon incorporation into cells to inhibit cell growth (Bio Techniques 28: 162-165, January 2000). As the immunotoxin, a recombinant complex protein of a diphtheria toxin catalytic domain and protein G may be used.

The antitumor activity of the antibody can be confirmed in vitro by determining inhibitory activity against cell growth. For example, a cancer cell line overexpressing a target protein for the antibody is cultured, and the antibody is added at varying concentrations into the culture system to determine inhibitory activity against focus formation, colony formation, and spheroid growth. The antitumor activity can be confirmed in vivo, for example, by administering the antibody to a nude mouse with a transplanted cancer cell line highly expressing the target protein, and determining change in the cancer cell.

Since the compound conjugated in the antibody-drug conjugate exerts an antitumor effect, it is preferred but not essential that the antibody itself should have an antitumor effect. For the purpose of specifically and selectively exerting the cytotoxic activity of the antitumor compound against cancer cells, it is important and also preferred that the antibody should have the property of internalizing to migrate into cancer cells.

The antibody for use in production of the antibody-drug conjugate according to the present invention can be obtained by a procedure known in the art. For example, the antibody of the present invention can be obtained using a method usually carried out in the art, which involves immunizing animals with an antigenic polypeptide and collecting and purifying antibodies produced in vivo. The origin of the antigen is not limited to humans, and the animals may be immunized with an antigen derived from a non-human animal such as a mouse, a rat and the like. In this case, the cross-reactivity of antibodies binding to the obtained heterologous antigen with human antigens can be tested to screen for an antibody applicable to a human disease.

Alternatively, antibody-producing cells which produce antibodies against the antigen are fused with myeloma cells according to a method known in the art (e.g., Kohler and Milstein, Nature (1975) 256, p. 495-497; and Kennet, R. ed., Monoclonal Antibodies, p. 365-367, Plenum Press, N.Y. (1980)) to establish hybridomas, from which monoclonal antibodies can in turn be obtained.

The antigen can be obtained by genetically engineering host cells to produce a gene encoding the antigenic protein. Specifically, vectors that permit expression of the antigen gene are prepared and transferred to host cells so that the gene is expressed. The antigen thus expressed can be purified. The antibody can also be obtained by a method of immunizing animals with the above-described genetically engineered antigen-expressing cells or a cell line expressing the antigen.

The antibody for use in production of the antibody-drug conjugate according to the present invention is preferably a recombinant antibody obtained by artificial modification for the purpose of decreasing heterologous antigenicity to humans such as a chimeric antibody or a humanized antibody, or is preferably an antibody having only the gene sequence of an antibody derived from a human, that is, a human antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived antibody constant region can be exemplified (Proc. Natl. Acad. Sci. USA, 81, 6851-6855, (1984)).

As the humanized antibody, an antibody obtained by integrating only the complementarity determining region (CDR) of a heterologous antibody into a human-derived antibody (Nature (1986) 321, pp. 522-525), and an antibody obtained by grafting a part of the amino acid residues of the framework of a heterologous antibody as well as the CDR sequence of the heterologous antibody to a human antibody by a CDR-grafting method (WO 90/07861), and an antibody humanized using a gene conversion mutagenesis strategy (U.S. Pat. No. 5,821,337) can be exemplified.

As the human antibody, an antibody generated by using a human antibody-producing mouse having a human chromosome fragment including genes of a heavy chain and light chain of a human antibody (see Tomizuka, K. et al., Nature Genetics (1997) 16, p. 133-143; Kuroiwa, Y. et. al., Nucl. Acids Res. (1998) 26, p. 3447-3448; Yoshida, H. et. al., Animal Cell Technology: Basic and Applied Aspects vol. 10, p. 69-73 (Kitagawa, Y., Matsuda, T. and Iijima, S. eds.), Kluwer Academic Publishers, 1999; Tomizuka, K. et. al., Proc. Natl. Acad. Sci. USA (2000) 97, p. 722-727, etc.) can be exemplified. As an alternative, an antibody obtained by phage display, the antibody being selected from a human antibody library (see Wormstone, I. M. et. al, Investigative Ophthalmology & Visual Science. (2002)43 (7), p. 2301-2308; Carmen, S. et. al., Briefings in Functional Genomics and Proteomics (2002), 1(2), p. 189-203; Siriwardena, D. et. al., Ophthalmology (2002) 109(3), p. 427-431, etc.) can be exemplified.

In the present invention, modified variants of the antibody for use in production of the antibody-drug conjugate according to the present invention are also included. The modified variant refers to a variant obtained by subjecting the antibody according to the present invention to chemical or biological modification. Examples of the chemically modified variant include variants including a linkage of a chemical moiety to an amino acid skeleton, variants including a linkage of a chemical moiety to an N-linked or O-linked carbohydrate chain, etc. Examples of the biologically modified variant include variants obtained by post-translational modification (such as N-linked or O-linked glycosylation, N- or C-terminal processing, deamidation, isomerization of aspartic acid, or oxidation of methionine), and variants in which a methionine residue has been added to the N terminus by being expressed in a prokaryotic host cell. Further, an antibody labeled so as to enable the detection or isolation of the antibody or an antigen according to the present invention, for example, an enzyme-labeled antibody, a fluorescence-labeled antibody, and an affinity-labeled antibody are also included in the meaning of the modified variant. Such a modified variant of the antibody according to the present invention is useful for improving the stability and blood retention of the antibody, reducing the antigenicity thereof, detecting or isolating an antibody or an antigen, and so on.

Further, by regulating the modification of a glycan which is linked to the antibody according to the present invention (glycosylation, defucosylation, etc.), it is possible to enhance antibody-dependent cellular cytotoxic activity. As the technique for regulating the modification of a glycan of antibodies, WO 99/54342, WO 00/61739, WO 02/31140, etc. are known. However, the technique is not limited thereto. In the antibody according to the present invention, antibodies in which the modification of a glycan is regulated are also included.

It is known that a lysine residue at the carboxyl terminus of the heavy chain of an antibody produced in a cultured mammalian cell is deleted (Journal of Chromatography A, 705: 129-134 (1995)), and it is also known that two amino acid residues (glycine and lysine) at the carboxyl terminus of the heavy chain of an antibody produced in a cultured mammalian cell are deleted and a proline residue newly located at the carboxyl terminus is amidated (Analytical Biochemistry, 360: 75-83 (2007)). However, such deletion and modification of the heavy chain sequence do not affect the antigen-binding affinity and the effector function (the activation of complement, antibody-dependent cellular cytotoxicity, etc.) of the antibody. Therefore, in the antibody according to the present invention, antibodies subjected to such modification and functional fragments of the antibody are also included, and deletion variants in which one or two amino acids have been deleted at the carboxyl terminus of the heavy chain, variants obtained by amidation of deletion variants (for example, a heavy chain in which the carboxyl terminal proline residue has been amidated), and the like are also included. The type of deletion variant having a deletion at the carboxyl terminus of the heavy chain of the antibody according to the present invention is not limited to the above variants as long as the antigen-binding affinity and the effector function are conserved. The two heavy chains constituting the antibody according to the present invention may be of one type selected from the group consisting of a full-length heavy chain and the above-described deletion variant, or may be of two types in combination selected therefrom. The ratio of the amount of each deletion variant can be affected by the type of cultured mammalian cells which produce the antibody according to the present invention and the culture conditions; however, an antibody in which one amino acid residue at the carboxyl terminus has been deleted in both of the two heavy chains in the antibody according to the present invention can be preferably exemplified.

As isotypes of the antibody according to the present invention, for example, IgG (IgG1, IgG2, IgG3, IgG4) can be exemplified, and IgG1 or IgG2 can be exemplified preferably.

Examples of antibodies applicable to production of the antibody-drug conjugate according to the present invention can include, but are not particularly limited to, an anti-HER2 antibody, an anti-HER3 antibody, an anti-TROP2 antibody, an anti-B7-H3 antibody, an anti-CD3 antibody, an anti-CD30 antibody, an anti-CD33 antibody, an anti-CD37 antibody, an anti-CD56 antibody, an anti-CD98 antibody, an anti-DR5 antibody, an anti-EGFR antibody, an anti-EPHA2 antibody, an anti-FGFR2 antibody, an anti-FGFR4 antibody, an anti-FOLR1 antibody, an anti-VEGF antibody, an anti-CD20 antibody, an anti-CD22 antibody, an anti-CD70 antibody, an anti-PSMA antibody, an anti-CEA antibody, and an anti-Mesothelin antibody, and an anti-HER2 antibody, an anti-HER3 antibody, an anti-TROP2 antibody, and an anti-B7-H3 antibody can be preferably exemplified, and an anti-HER2 antibody can be more preferably exemplified.

In the present invention, the term "anti-HER2 antibody" refers to an antibody which specifically binds to HER2 (Human Epidermal Growth Factor Receptor Type 2; ErbB-2), and preferably has an activity of internalizing in HER2-expressing cells by binding to HER2.

Examples of the anti-HER2 antibody include trastuzumab (U.S. Pat. No. 5,821,337) and pertuzumab (International Publication No. WO 01/00245), and trastuzumab can be preferably exemplified.

In the present invention, the term "trastuzumab" is also called HERCEPTIN (registered trademark), huMAb4D5-8, or rhuMAb4D5-8 and is a humanized anti-HER2 antibody comprising a heavy chain consisting of an amino acid sequence consisting of amino acid residues 1 to 449 of SEQ ID NO: 1 (FIG. 1) and a light chain consisting of an amino acid sequence consisting of amino acid residues 1 to 214 of SEQ ID NO: 2 (FIG. 2).

A preferred anti-HER2 antibody for use in production of the antibody-drug conjugate according to the present invention is:

(1) an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2; or (2) an antibody comprising a heavy chain consisting of the amino acid sequence represented by SEQ ID NO: 1 and a light chain consisting of the amino acid sequence represented by SEQ ID NO: 2.

In the present invention, the term "anti-HER3 antibody" refers to an antibody which specifically binds to HER3 (Human Epidermal Growth Factor Receptor Type 3; ErbB-3), and preferably has an activity of internalizing in HER3-expressing cells by binding to HER3.

Examples of the anti-HER3 antibody include patritumab (U3-1287), U1-59 (International Publication No. WO 2007/077028), MM-121 (seribantumab), an anti-ERBB3 antibody described in International Publication No. WO 2008/100624, RG-7116 (lumretuzumab), and LJM-716 (elgemtumab), and patritumab and U1-59 can be preferably exemplified.

In the present invention, the term "anti-TROP2 antibody" refers to an antibody which specifically binds to TROP2 (TACSTD2: Tumor-associated calcium signal transducer 2; EGP-1), and preferably has an activity of internalizing in TROP2-expressing cells by binding to TROP2.

Examples of the anti-TROP2 antibody include hTINA1-H1L1 (International Publication No. WO 2015/098099).

In the present invention, the term "anti-B7-H3 antibody" refers to an antibody which specifically binds to B7-H3, and preferably has an activity of internalizing in B7-H3-expressing cells by binding to B7-H3.

Examples of the anti-B7-H3 antibody include M30-H1-L4 (International Publication No. WO 2014/057687).

[Drug-Linker Intermediate for Use in Production of Antibody-Drug Conjugate]

A drug-linker intermediate for use in production of the antibody-drug conjugate according to the present invention is represented by the following formula.

[Formula 17]

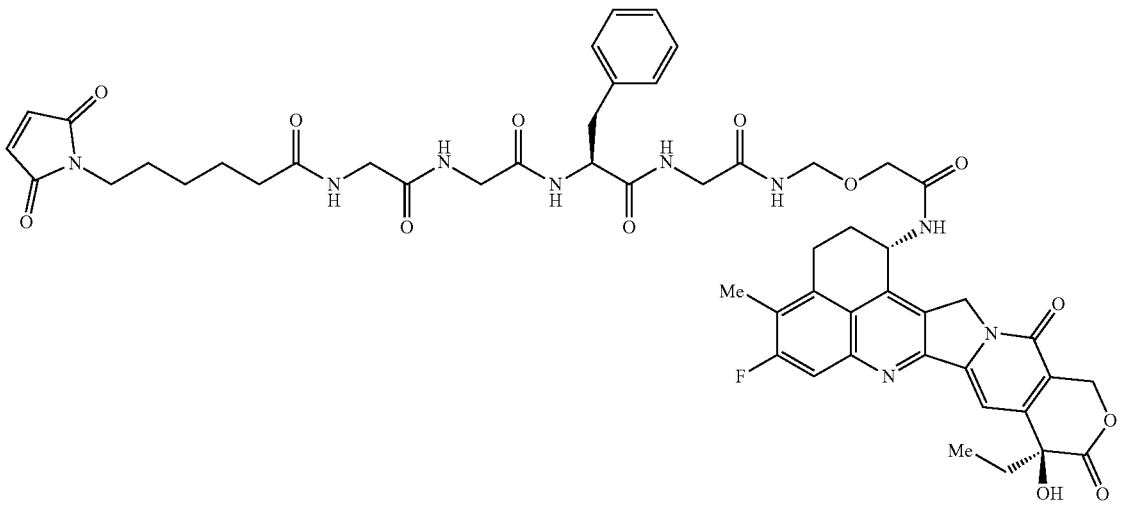

The drug-linker intermediate can be expressed as the chemical name N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide, and can be produced with reference to descriptions in International Publication No. WO 2014/057687, International Publication No. WO 2015/098099, International Publication No. WO 2015/115091, International Publication No. WO 2015/155998, and so on.

[Conjugation Between Antibody and Drug-Linker Intermediate]

The antibody-drug conjugate used in the present invention can be produced by reacting the above-described drug-linker intermediate and an antibody having a thiol group (or referred to as a sulfhydryl group).

The antibody having a sulfhydryl group can be obtained by a method well known in the art (Hermanson, G. T, Bioconjugate Techniques, pp. 56-136, pp. 456-493, Academic Press (1996)). For example, by using 0.3 to 3 molar equivalents of a reducing agent such as tris(2-carboxyethyl)phosphine hydrochloride (TCEP) per interchain disulfide within the antibody and reacting with the antibody in a buffer solution containing a chelating agent such as ethylenediamine tetraacetic acid (EDTA), an antibody having a sulfhydryl group with partially or completely reduced interchain disulfides within the antibody can be obtained.

Further, by using 2 to 20 molar equivalents of the drug-linker intermediate per the antibody having a sulfhydryl group, an antibody-drug conjugate in which 2 to 8 drug molecules are conjugated per antibody molecule can be produced.

The average number of conjugated drug molecules per antibody molecule of the antibody-drug conjugate produced can be determined, for example, by a method of calculation based on measurement of UV absorbance for the antibody-drug conjugate and the conjugation precursor thereof at two wavelengths of 280 nm and 370 nm (UV method), or a method of calculation based on quantification through HPLC measurement for fragments obtained by treating the antibody-drug conjugate with a reducing agent (HPLC method).

Conjugation between the antibody and the drug-linker intermediate and calculation of the average number of conjugated drug molecules per antibody molecule of the antibody-drug conjugate can be performed with reference to descriptions in International Publication No. WO 2014/057687, International Publication No. WO 2015/098099, International Publication No. WO 2015/115091, International Publication No. WO 2015/155998, and so on.

In the present invention, the term "anti-HER2 antibody-drug conjugate" refers to an antibody-drug conjugate such that the antibody in an antibody-drug conjugate is an anti-HER2 antibody.

The average number of units of the drug-linker conjugated per antibody molecule in the anti-HER2 antibody-drug conjugate used in the present invention is preferably 2 to 8, more preferably 3 to 8, even more preferably 7 to 8, even more preferably 7.5 to 8, and even more preferably about 8.

The anti-HER2 antibody-drug conjugate used in the present invention can be produced with reference to descriptions in International Publication No. WO 2015/115091 and so on.

In the present invention, the term "anti-HER3 antibody-drug conjugate" refers to an antibody-drug conjugate such that the antibody in an antibody-drug conjugate is an anti-HER3 antibody.

The average number of units of the drug-linker conjugated per antibody molecule in the anti-HER3 antibody-drug conjugate used in the present invention is preferably 2 to 8, more preferably 3 to 8, even more preferably 7 to 8, even more preferably 7.5 to 8, and even more preferably about 8.

The anti-HER3 antibody-drug conjugate used in the present invention can be produced with reference to descriptions in International Publication No. WO 2015/155998 and so on.

In the present invention, the term "anti-TROP2 antibody-drug conjugate" refers to an antibody-drug conjugate such that the antibody in an antibody-drug conjugate is an anti-TROP2 antibody.

The average number of units of the drug-linker conjugated per antibody molecule in the anti-TROP2 antibody-drug conjugate used in the present invention is preferably 2 to 8, more preferably 3 to 5, even more preferably 3.5 to 4.5, and even more preferably about 4.

The anti-TROP2 antibody-drug conjugate used in the present invention can be produced with reference to descriptions in International Publication No. WO 2015/098099 and so on.

In the present invention, the term "anti-B7-H3 antibody-drug conjugate" refers to an antibody-drug conjugate such that the antibody in an antibody-drug conjugate is an anti-B7-H3 antibody.

The average number of units of the drug-linker conjugated per antibody molecule in the anti-B7-H3 antibody-drug conjugate used in the present invention is preferably 2 to 8, more preferably 3 to 5, even more preferably 3.5 to 4.5, and even more preferably about 4.

The anti-B7-H3 antibody-drug conjugate used in the present invention can be produced with reference to descriptions in International Publication No. WO 2014/057687 and so on.

[Immune Checkpoint Inhibitor]

In the present invention, the term "immune checkpoint inhibitor" refers to an agent which inhibits the immune suppression system to activate tumor immunity.

Preferred examples of the immune checkpoint inhibitor used in the present invention can include, but not particularly limited to, an anti-PD-1 antibody, an anti-PD-L1 antibody, and an anti-CTLA-4 antibody, and an anti-PD-1 antibody and an anti-PD-L1 antibody can be more preferably exemplified.

In the present invention, the term "anti-PD-1 antibody" refers to an antibody which specifically binds to PD-1 (Programmed cell death-1; CD279; PDCD1), and has an activity of reducing, inhibiting, and/or interfering with signal transduction caused by interaction between PD-1 and PD-L1 or PD-L2 as a binding partner. The anti-PD-1 antibody used in the present invention is not particularly limited as long as the clinical efficacy and safety thereof have been confirmed, and nivolumab (International Publication No. WO 2006/121168, etc.) and pembrolizumab (International Publication No. WO 2008/156712, etc.) can be preferably exemplified. For the purpose of confirming the effect of use in combination with the antibody-drug conjugate used in the present invention in a preclinical study, a commercially available anti-PD-1 antibody for research (e.g., clone RMP1-14) and so on can be used.

In the present invention, the term "anti-PD-L1 antibody" refers to an antibody which specifically binds to PD-L1 (Programmed cell death ligand 1; CD274; B7-H1), and has an activity of reducing, inhibiting, and/or interfering with signal transduction caused by interaction between PD-L1 and PD-1 or B7.1 (CD80) as a binding partner. The anti-PD-L1 antibody used in the present invention is not particularly limited as long as the clinical efficacy and safety thereof have been confirmed, and atezolizumab (International Publication No. WO 2010/077634, etc.), durvalumab (International Publication No. WO 2011/066389, etc.), and avelumab (International Publication No. WO 2013/079174, etc.) can be preferably exemplified. For the purpose of confirming the effect of use in combination with the antibody-drug conjugate used in the present invention in a preclinical study, a commercially available anti-PD-L1 antibody for research (e.g., clone 10F.9G2) and so on can be used.

In the present invention, the term "anti-CTLA-4 antibody" refers to an antibody which specifically binds to CTLA-4 (Cytotoxic T-lymphocyte-associated protein 4; CD152), and has an activity of reducing, inhibiting, and/or interfering with signal transduction caused by interaction between CTLA-4 and B7.1 (CD80) or B7.2 (CD86) as a binding partner. The anti-CTLA-4 antibody used in the present invention is not particularly limited as long as the clinical efficacy and safety thereof have been confirmed, and ipilimumab (International Publication No. WO 2001/014424, etc.) and tremelimumab (International Publication No. WO 2000/037504, etc.) can be preferably exemplified. For the purpose of confirming the effect of use in combination with the antibody-drug conjugate used in the present invention in a preclinical study, a commercially available anti-CTLA-4 antibody for research (e.g., clone 9H10) and so on can be used.

[Medicines]

Described in the following are a pharmaceutical composition and a therapeutic method wherein the antibody-drug conjugate according to the present invention and an immune checkpoint inhibitor are administered in combination, and a pharmaceutical composition and a therapeutic method for use in treatment of a disease that can be ameliorated through an antitumor immunity-activating effect wherein the antibody-drug conjugate according to the present invention is included.

The pharmaceutical composition and therapeutic method of the present invention may be characterized in that the antibody-drug conjugate and the immune checkpoint inhibitor are separately contained as active components in different formulations, and are administered simultaneously or at different times, or characterized in that the antibody-drug conjugate and the immune checkpoint inhibitor are contained as active components in a single formulation and administered. The pharmaceutical composition and therapeutic method according to the present invention may be such that the antibody-drug conjugate according to the present invention is contained as an active component in a single formulation and administered for treating a disease that can be ameliorated through an antitumor immunity-activating effect.

The pharmaceutical composition and therapeutic method of the present invention can be used for treating cancer, and can be preferably used for treating at least one disease selected from the group consisting of lung cancer (including non-small cell lung cancer), urothelial cancer, colorectal cancer (also called colon and rectal cancer, and including colon cancer and rectal cancer), prostate cancer, ovarian cancer, pancreatic cancer, breast cancer, bladder cancer, gastric cancer (also called gastric adenocarcinoma), esophagogastric junction adenocarcinoma, gastrointestinal stromal tumor, uterine cervix cancer, esophageal cancer, squamous cell carcinoma, peritoneal cancer, liver cancer, hepatocellular cancer, endometrial cancer, uterine cancer, salivary gland cancer, kidney cancer, vulval cancer, thyroid cancer, penis cancer, leukemia, malignant lymphoma, plasmacytoma, myeloma, neuroepithelial tissue tumor, nerve sheath tumor, head-and-neck cancer, skin cancer, pharyngeal cancer, gallbladder cancer, bile duct cancer, mesothelioma, Paget's disease, and sarcoma.

The pharmaceutical composition and therapeutic method of the present invention can be selectively used as an agent for drug therapy, which is a main method for treating cancer, and as a result, can delay development of cancer cells, inhibit growth thereof, and further kill cancer cells. These effects can allow cancer patients to be free from symptoms caused by cancer or achieve improvement in QOL of cancer patients and attain a therapeutic effect by sustaining the lives of the cancer patients. Even if the pharmaceutical composition and therapeutic method of the present invention do not accomplish killing cancer cells, they can achieve higher QOL of cancer patients while achieving longer-term survival, by inhibiting or controlling the growth of cancer cells.

In such drug therapy, the pharmaceutical composition and therapeutic method of the present invention can be used as an agent alone and in addition, they can be used as an agent in combination with an additional therapy in adjuvant therapy and can be combined with surgical operation, radiotherapy, hormone therapy, or the like. Furthermore, they can also be used as an agent for drug therapy in neoadjuvant therapy.

In addition to the therapeutic use as described above, for example, a prophylactic effect such as suppressing the growth of small metastatic cancer cells and further killing them can also be expected for the pharmaceutical composition and therapeutic method according to the present invention. For example, an effect of inhibiting and killing cancer cells in a body fluid in the course of metastasis or an effect of, for example, inhibiting and killing small cancer cells immediately after implantation in any tissue can be expected. Accordingly, inhibition of cancer metastasis or a prophylactic effect can be expected, particularly, after surgical removal of cancer.

The pharmaceutical composition and therapeutic method of the present invention can be expected to exert a therapeutic effect by application as systemic therapy to patients, and additionally, by local application to cancer tissues.

The pharmaceutical composition and therapeutic method of the present invention can be preferably used for a mammal, but are more preferably used for a human.

The pharmaceutical composition of the present invention can be administered as a pharmaceutical composition containing at least one pharmaceutically suitable ingredient. Substances used in the pharmaceutical composition of the present invention can be suitably selected and applied from formulation additives or the like that are generally used in the art, in view of the dosage or administration concentration. For example, the pharmaceutical composition above typically contains at least one pharmaceutical carrier (for example, sterilized liquid). Herein, the liquid includes, for example, water and oil (petroleum oil and oil of animal origin, plant origin, or synthetic origin). The oil may be, for example, peanut oil, soybean oil, mineral oil, or sesame oil. Water is a more typical carrier when the pharmaceutical composition above is intravenously administered. Saline solution, an aqueous dextrose solution, and an aqueous glycerol solution can be also used as a liquid carrier, in particular, for an injection solution. A suitable pharmaceutical vehicle can be selected from ones known in the art. If desired, the composition above may also contain a trace amount of a moisturizing agent, an emulsifying agent, or a pH buffering agent. Examples of suitable pharmaceutical carriers are disclosed in "Remington's Pharmaceutical Sciences" by E. W. Martin. The formulations correspond to the administration mode.

Various delivery systems are known and they can be used for administering the pharmaceutical composition of the present invention. Examples of the administration route can include intradermal, intramuscular, intraperitoneal, intravenous, and subcutaneous routes, but are not limited thereto. The administration can be made by injection or bolus injection, for example. According to a specific preferred embodiment, the administration of the antibody-drug conjugate and immune checkpoint inhibitor used in the present invention is performed by injection. Parenteral administration is a preferred administration route.

According to a representative embodiment, the pharmaceutical composition is prescribed, as a pharmaceutical composition suitable for intravenous administration to humans, according to conventional procedures. The composition for intravenous administration is typically a solution in a sterile and isotonic aqueous buffer solution. If necessary, the pharmaceutical composition may contain a solubilizing agent and local anesthetics to alleviate pain at an injection site (for example, lignocaine). Generally, the ingredient above is provided individually as any one of a lyophilized powder or an anhydrous concentrate contained in a container which is obtained by sealing in an ampoule or a sachet having an amount of the active agent or as a mixture in a unit dosage form. When the pharmaceutical composition is to be administered by injection, it may be administered from an injection bottle containing water or saline of sterile pharmaceutical grade. When the pharmaceutical composition is administered by injection, an ampoule of sterile water or saline for injection may be provided such that the aforementioned ingredients are admixed with each other before administration.

The pharmaceutical composition and therapeutic method of the present invention may include a cancer treating agent other than the antibody-drug conjugate and immune checkpoint inhibitor according to the present invention. The pharmaceutical composition and therapeutic method of the present invention can be administered in combination with other cancer treating agents. The anti-cancer effect may be enhanced accordingly. Other anti-cancer agents used for such purpose may be administered to an individual simultaneously with, separately from, or subsequently to the pharmaceutical composition of the present invention, and may be administered while varying the administration interval for each. Examples of cancer treating agents include 5-fluorouracil (5-FU), pertuzumab, trastuzumab, paclitaxel, carboplatin, cisplatin, gemcitabine, capecitabine, irinotecan (CPT-11), docetaxel, pemetrexed, sorafenib, vinblastin, vinorelbine, everolims, tanespimycin, bevacizumab, oxaliplatin, lapatinib, trastuzumab emtansine (T-DM1) or agents described in International Publication No. WO 2003/038043, LH-RH alagogues (leuprorelin, goserelin, or the like), estramustine phosphate, estrogen antagonists (tamoxifen, raloxifene, or the like), and aromatase inhibitors (anastrozole, letrozole, exemestane, or the like), but are not limited as long as they are agents having an antitumor activity.

The pharmaceutical composition can be formulated into a lyophilization formulation or a liquid formulation as a formulation having the desired composition and required purity. When formulated as a lyophilization formulation, it may be a formulation containing suitable formulation additives that are used in the art. Also for a liquid formulation, it can be formulated as a liquid formulation containing various formulation additives that are used in the art.

The composition and concentration of the pharmaceutical composition may vary depending on the administration method. However, the antibody-drug conjugate and immune checkpoint inhibitor contained in the pharmaceutical composition of the present invention can exhibit a pharmaceutical effect even at a small dosage when the antibody-drug conjugate has a higher affinity for an antigen, that is, a higher affinity (=lower Kd value) in terms of the dissociation constant (that is, Kd value) for the antigen. Thus, for determining the dosage of the antibody-drug conjugate and immune checkpoint inhibitor, the dosage can be determined in view of the situation relating to the affinity with the antigen. When the antibody-drug conjugate and immune checkpoint inhibitor according to the present invention are administered to a human, for example, about 0.001 to 100 mg/kg can be administered once or administered in several portions with intervals of 1 to 180 days.

Examples of administration methods for the antibody-drug conjugate according to the present invention include a method of administering 0.8 mg/kg to 8 mg/kg once every three weeks. Examples of the dose include 0.8 mg/kg, 1.6 mg/kg, 3.2 mg/kg, 5.4 mg/kg, 6.4 mg/kg, 7.4 mg/kg, and 8 mg/kg. Although it is sufficient to administer once every three weeks (q3w), administration may be performed once a week (q1w), once every two weeks (q2w), or once every four weeks (q4w).

EXAMPLES

The present invention is specifically described in view of the examples shown below. However, the present invention is not limited to these. Further, it is by no means to be interpreted in a limited way.

Production Example 1: Preparation of Antibody-Drug Conjugate

In accordance with a production method described in International Publication No. WO 2015/115091 with use of a humanized anti-HER2 antibody (trastuzumab), an antibody-drug conjugate in which a drug-linker represented by the following formula:

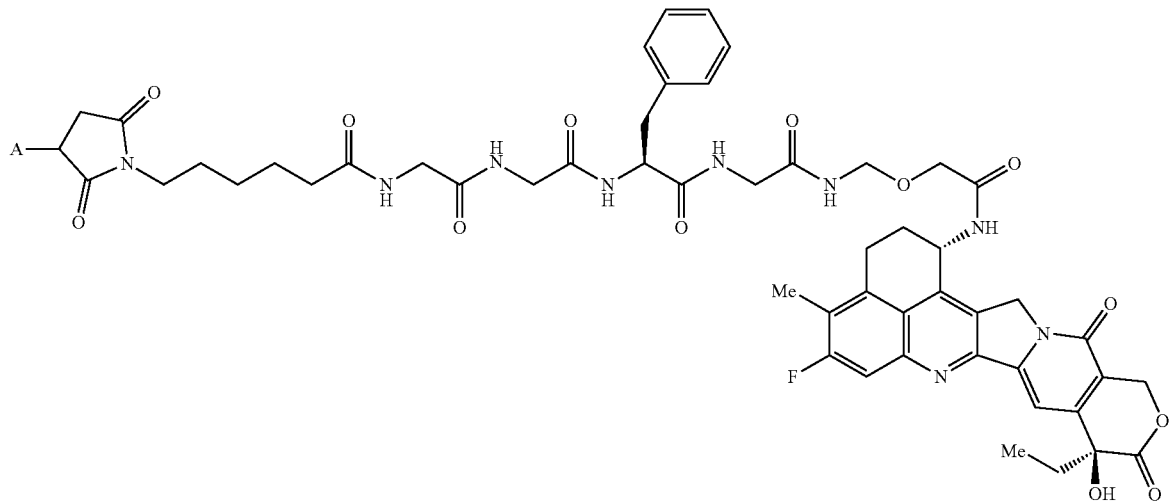

wherein A represents the connecting position to an antibody, is conjugated to the anti-HER2 antibody via a thioether bond (hereinafter, referred to as "the antibody-drug conjugate (1)") was produced.

Production Example 2: Preparation of Compound (A)

In accordance with a production method described in International Publication No. WO 2014/057687, a compound represented by the following formula:

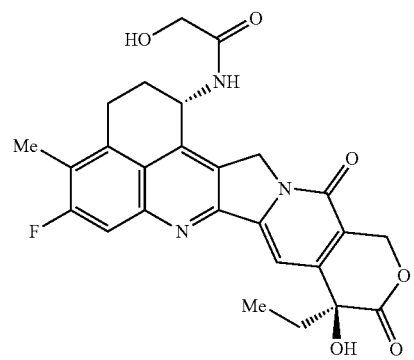

(compound (A)) was produced.

Evaluation Example 1: Life Prolongation Test

Mouse: 6-week-old female BALB/c mice (BALB/c AnN-CrlCrlj) (Charles River Laboratories Japan, Inc.) were subjected to experiment.

Assay and calculation expression: The major axis and minor axis of a tumor were measured twice a week by using an electronic digital caliper (CD15-CX, Mitutoyo Corp.), and the tumor volume (mm$^3$) was calculated. The calculation expression is as shown below.

Tumor volume (mm$^3$)=0.5×Major axis (mm)×[Minor axis (mm)]$^2$

From the viewpoint of animal testing ethics, individuals whose tumor volume exceeded 3000 mm$^3$ were euthanized.

The antibody-drug conjugate (1) (Drug-to-Antibody Ratio: 7.6) was diluted with special solvent (10 mM Histidine, 10% Trehalose, 0.02% Polysorbate 20, pH 5.5) for use. An anti-PD-1 antibody (clone RMP1-14) was purchased from Bio X Cell, and diluted with DPBS (Sigma-Aldrich Co. LLC) for use. In administration, a dose of 10 mL/kg was intravenously administered to the tail vein of each mouse.

A human HER2 gene was transfected into the mouse colorectal cancer cell line CT26.WT (CRL2638) purchased from American Type Culture Collection with a retrovirus vector to prepare CT26.WT-hHER2 cells for use. These cells were expressing human HER2 protein on their cell membranes. The CT26.WT-hHER2 cells were suspended in physiological saline, and $5.0 \times 10^6$ cells were subcutaneously transplanted to the right axilla of each BALB/c mouse, and the mice were randomly grouped 6 days thereafter (Day 0). The antibody-drug conjugate (1) was intravenously administered to the tail vein of each mouse at a dose of 10 mg/kg on Days 0 and 7, twice in total. The anti-PD-1 antibody was intravenously administered to the tail vein of each mouse at a dose of 2.5 mg/kg on Days 0, 3, 7, 10, and 14, five times in total. A combined administration group with the antibody-drug conjugate (1) and the anti-PD-1 antibody was established, and a group with administration of the special solvent for the antibody-drug conjugate (1) was established as a control group. The number of mice in each group was six, and tumor volumes were measured until Day 43.

The results are shown in FIG. 3. Kaplan-Meier curves are shown therein, where the timing when tumor volume exceeded 3000 mm$^3$ was regarded as the end point. The ordinate depicts survival rates (%) and the abscissa depicts days from the day of initial administration. For the control group, drop-out was found from Day 17, and all of the mice were determined as subjects of euthanasia by Day 24. For the antibody-drug conjugate (1) group, in contrast, drop-out was found from Day 28, and three mice survived until Day 43. For the anti-PD-1 antibody group, drop-out was found from Day 21, and two mice survived until Day 43. Moreover, for the combined administration group with these two agents, all the mice survived until Day 43. Weight loss was observed for none of the mice in all of the groups in this test. From the results, the antitumor effect of single administration of each agent was confirmed, and it was further confirmed that such effect is dramatically enhanced through use of the two agents in combination.

Evaluation Example 2: Life Prolongation Test

A test was conducted in the same manner as in Evaluation Example 1. The anti-PD-1 antibody was intravenously administered to the tail vein of each mouse at a dose of 5 mg/kg on Days 0, 3, 7, and 10, four times in total, where the number of mice in each group was 20, and tumor volumes were measured until Day 38. Comparison on pharmaceutical effect between the control group and each of the antibody-drug conjugate (1) group and the anti-PD-1 antibody group, and comparison on pharmaceutical effect between each of the antibody-drug conjugate (1) group and the anti-PD-1 antibody group and the combined administration group with both agents were performed by using the Kaplan-Meier method/logrank test (comparison among multiple groups). The day when estimated tumor volume exceeded 3000 mm$^3$ (day of euthanasia) was defined as the day of event occurrence (day of death). P values adjusted for multiplicity were expressed as numerical values to the fourth decimal place, and values of P<0.05 (two-tailed test) were regarded as significant differences.

The results are shown in FIG. 4. The antibody-drug conjugate (1) group exhibited a significantly superior antitumor effect to the control group (P=0.0001). The anti-PD-1 antibody group exhibited a significantly superior antitumor effect to the control group (P=0.0010). Further, the combined administration group exhibited a significantly superior antitumor effect to the antibody-drug conjugate (1) group (P=0.0006). The combined administration group exhibited a significantly superior antitumor effect to the anti-PD-1 antibody group (P<0.0001).

Evaluation Example 3: Retransplantation Test

The antibody-drug conjugate (1) was administered to mice with subcutaneously transplanted CT26.WT-hHER2 cells in the same manner as in Evaluation Example 1. The mice were randomly grouped 5 days after the transplantation. From these mice, mice whose tumor completely disappeared were selected (hereinafter, referred to as "antibody-drug conjugate (1)-treated cured mice"). Untreated mice were used for a control (hereinafter, referred to as "control mice").

Subsequently, $5.0 \times 10^6$ cells of CT26.WT-hHER2 cells or CT26.WT-mock cells were subcutaneously transplanted to the left axilla of each of the antibody-drug conjugate (1)-treated cured mice and the control mice (retransplantation, Day 0), and tumor volumes were measured until Day 17. The number of mice in each group was nine.

The results are shown in FIG. 5. The ordinate depicts tumor volumes (mm$^3$) and the abscissa depicts days from the day of retransplantation. Tumor growth was found for the control mice with retransplanted CT26.WT-hHER2 cells and those with retransplanted CT26.WT-mock cells. In contrast, almost no tumor growth, thus, tumor rejection was found for the antibody-drug conjugate (1)-treated cured mice with retransplanted CT26.WT-hHER2 cells and those with retransplanted CT26.WT-mock cells. From these results, administration of the antibody-drug conjugate (1) was confirmed to cause the formation of immune memory against the tumor.

Evaluation Example 4: ELISPOT Analysis

This analysis was performed by using Murine IFNγ Single-Color Enzymatic ELISPOT Assay. The spleen was excised from each of the mice used in Evaluation Example 3, and $1.0 \times 10^6$ cells/mL of splenocytes were prepared therefrom with CTL test medium. CT26.WT-hHER2 cells and CT26.WT-mock cells were each treated with 10 μg/mL of mitomycin C for 2 hours and washed, and the cells were then collected, and $1.0 \times 10^6$ cells/mL of cells were prepared with CTL test medium, which was used as an antigen. The splenocytes and the antigen were added to an anti-IFNγ antibody-coated PVDF-membrane plate each at 100 μL/well, and co-cultured at 37° C. for 24 hours, and then the number of IFNγ-producing splenocytes was counted. Comparison between the control group and the antibody-drug conjugate (1) group was performed by using the Wilcoxon rank sum test, P values were expressed as numerical values to the fourth decimal place, and values of P<0.05 (two-tailed test) were regarded as significant differences.

The results are shown in FIGS. 6 to 9. The CT26.WT-hHER2 cell-derived antigen was found to give a significantly larger number of IFNγ-producing splenocytes for the splenocytes of the antibody-drug conjugate (1)-treated cured mice with retransplanted CT26.WT-hHER2 cells than for the splenocytes of the control mice (P=0.0012, FIG. 6). The CT26.WT-mock cell-derived antigen was also found to give a significantly larger number of IFNγ-producing splenocytes (P=0.0008, FIG. 7).

Further, even in the cases involving retransplantation of CT26.WT-mock cells, the CT26.WT-hHER2 cell-derived antigen was found to give a significantly larger number of IFNγ-producing splenocytes for the splenocytes of the antibody-drug conjugate (1)-treated cured mice than for the splenocytes of the control mice (P=0.0116, FIG. 8). The CT26.WT-mock cell-derived antigen was also found to give a significantly larger number of IFNγ-producing splenocytes (P=0.0052, FIG. 9).

These results suggested that T cells which recognize a CT26.WT cell-derived antigen other than human HER2 had been induced in the antibody-drug conjugate (1)-treated cured mice.

The results of Evaluation Examples 3 and 4 demonstrated that the antibody-drug conjugate (1) had a promoting effect on the formation of immune memory against tumor. The effect was found not only for tumor expressing HER2 but also for tumor derived from the same origin and not expressing HER2.

Thus, it was revealed that the antibody-drug conjugate used in the present invention has a promoting effect on the formation of immune memory, not only against tumor expressing the antigen for the antibody in the antibody-drug conjugate, but also against tumor not expressing the antigen for the antibody in the antibody-drug conjugate in the same individual.

Evaluation Example 5: Evaluation of Effect on In Vitro Dendritic Cells

BALB/c mice were euthanized, and bone marrow cells were then separated from each femur, and cultured with an RPMI 1640 medium containing 10% FBS, 55 µM 2-mercaptoethanol, 100 U/mL penicillin, 100 U/mL streptomycin, 1 mM sodium pyruvate, 1×non-essential amino acid, 2 mM L-glutamine, and 10 ng/mL mouse GM-CSF for 11 days to induce bone marrow-derived dendritic cells. To the culture solution for the induced dendritic cells, the compound (A) was added to a concentration of 0.0625 µM, 0.125 µM, 0.25 µM, 0.5 µM, or 1 µM. For a control, DMSO in a quantity equal to that of the compound (A) was added. After 24 hours, staining was performed by using a Pacific Blue labeled anti-mouse CD45 Antibody (103126, BioLegend), PE labeled anti-mouse CD86 (B7-2) (553692, Becton Dickinson), APC labeled anti-mouse CD11c (550261, Becton Dickinson), and FITC labeled anti-mouse MHC Class II (I-A/I-E) (11-5321-85, Thermo Fisher Scientific), and analysis was performed by using an FACS Canto II. Dead cells had been stained with a LIVE/DEAD Fixable Near-IR Dead Cell Stain Kit purchased from Thermo Fisher Scientific, and excluded from the analysis.

FIGS. 10 and 11 show measurement results of flow cytometry for CD11c-positive cells in terms of expression levels of CD86 and MHC class II, respectively. It was found that treatment with the compound (A) elevated expression levels of both CD86 and MHC class II, which are mature/activation markers for dendritic cells, as compared with the case with DMSO as the control.

The results of Evaluation Example 5 demonstrated that the compound (A) has an activating effect on dendritic cells.

Evaluation Example 6: Analysis of Intratumor Dendritic Cells

CT26.WT-hHER2 cells were transplanted to mice in the same manner as in Evaluation Example 1, and the mice were randomly grouped 8 days thereafter (Day 0). The antibody-drug conjugate (1) was intravenously administered to the tail vein of each mouse at a dose of 10 mg/kg on Day 0. A group with administration of the special solvent for the antibody-drug conjugate (1) was established as a control group. The number of mice in each group was seven. The mice were euthanized on Day 8, and tumors were excised. Single cell suspensions were prepared from the tumors by using a Tumor Dissociation Kit, mouse, purchased from Miltenyi Biotec, and stained and analyzed in the same manner as in Evaluation Example 5. Comparison between the control group and the antibody-drug conjugate (1) group was performed by using Student's t-test, P values were expressed as numerical values to the fourth decimal place, and values of P<0.05 (two-tailed test) were regarded as significant differences.

The results are shown in FIGS. 12 to 14.

It was found that the fraction of CD11c-, MHC class II-, CD45-positive cells (dendritic cells, DC) among CD45-positive cells (lymphocytic cells) in tumors significantly increased by administration of the antibody-drug conjugate (1) (FIG. 12).

Further, it was found that the number of dendritic cells expressing CD86 (activation marker) significantly increased by administration of the antibody-drug conjugate (1) (FIG. 13).

Furthermore, it was found that the expression level of CD86 on dendritic cells determined in terms of MFI (mean fluorescence intensity) was significantly elevated by administration of the antibody-drug conjugate (1) (FIG. 14).

These results confirmed that administration of the antibody-drug conjugate (1) to cancer-bearing mice results in increase of the number of dendritic cells among intratumor lymphocytes, increase of the number of CD86-positive cells among intratumor dendritic cells, and elevation of the expression level of CD86 on dendritic cells.

It has been demonstrated from the results of Evaluation Example 5 that the compound (A), which is a drug released from the antibody-drug conjugate (1), itself has an activating effect on dendritic cells. The "activating effect on dendritic cells" possessed by the compound (A) is an effect associated with the "activating effect on dendritic cells" possessed by the antibody-drug conjugate used in the present invention. The compound (A) is a compound which is generated from the antibody-drug conjugate used in the present invention after the antibody-drug conjugate used in the present invention migrates into cancer cells. Accordingly, the compound (A) is expected to have the same effect even in an antibody-drug conjugate in which the antibody portion is not an anti-HER2 antibody.

Evaluation Example 7: Analysis of Intratumor Cancer Cells

Cell suspensions were prepared in the same manner as in Evaluation Example 6, and then staining was performed with PE labeled anti-human Her2/neu (340552, Becton Dickinson), APC labeled anti-mouse CD274 (B7-H1, PD-L1) (124312, BioLegend), and FITC labeled anti-mouse H-2Dd (110606, BioLegend), and expression levels of MHC class I and expression levels of PD-L1 on cancer cells were determined with flow cytometry. Dead cells had been stained with a LIVE/DEAD Fixable Near-IR Dead Cell Stain Kit purchased from Thermo Fisher Scientific, and excluded from the analysis. Comparison between the control group and the antibody-drug conjugate (1) group was performed by using Student's t-test, P values were expressed as numerical values to the fourth decimal place, and values of P<0.05 (two-tailed test) were regarded as significant differences.

The results are shown in FIGS. 15 and 16.

It was found that the expression level of MHC class I on cancer cells (human HER2-positive cells) was significantly elevated by administration of the antibody-drug conjugate (1) (FIG. 15). MHC class I is a molecule necessary when T cells recognize cancer cells. Hence, it was suggested that the antibody-drug conjugate (1) activates antitumor immunity through promoting elevation of the expression level of MHC class I on cancer cells.

It was further found that the expression level of PD-L1 on cancer cells was significantly elevated by the antibody-drug conjugate (1) (FIG. 16). PD-L1 is known to act on PD-1 on T cells to elicit an immunosuppressive signal. Hence, it was suggested that the antibody-drug conjugate (1) activates antitumor immunity through promoting elevation of the expression level of PD-L1 on cancer cells, and combined use with a PD-1 antibody is expected to deactivate the suppressive signal, resulting in a higher antitumor effect.

Evaluation Example 8: Analysis of In Vitro Cancer Cells

To culture solution for CT26.WT-hHER2 cells, the compound (A) was added to a concentration of 0.0625 µM, 0.125 µM, 0.25 µM, 0.5 µM, or 1 µM. For a control, DMSO in a quantity equal to that of the compound (A) was added. After 24 hours, staining was performed by using PE labeled anti-human Her2/neu (340552, Becton Dickinson) and FITC labeled anti-mouse H-2Dd (110606, BioLegend), and expression levels of MHC class I on cancer cells were determined with flow cytometry. Dead cells had been stained with a LIVE/DEAD Fixable Near-IR Dead Cell Stain Kit purchased from Thermo Fisher Scientific, and excluded from the analysis. The mean fluorescence intensity (MFI) of MHC class I was calculated, and MFI for cells treated with an Isotype control was subtracted from the MFI for stained cells, and the resulting value was used as adjusted MFI. Comparison between the control group and the compound (A) group was performed by using Dunnett's test, P values were expressed as numerical values to the fourth decimal place, and values of P<0.05 (two-tailed test) were regarded as significant differences.

The results are shown in FIG. 17.

It was found that the expression level of MHC class I on CT26.WT-hHER2 cells was significantly elevated by the compound (A) (FIG. 17). Hence, it was suggested that the compound (A) activates antitumor immunity through promoting elevation of the expression level of MHC class I on cancer cells.

Evaluation Example 9: Antitumor Test Using Nude Mice

Mouse: 6-week-old female BALB/c-nu mice (CAnN.Cg-Foxn1[nu]/CrlCrlj [Foxn1nu/Foxn1nu]) (Charles River Laboratories Japan, Inc.) were subjected to experiment.

Assay and calculation expression: The major axis and minor axis of a tumor were measured twice a week by using an electronic digital caliper (CD15-CX, Mitutoyo Corp.), and the tumor volume ($mm^3$) was calculated. The calculation expression is as shown below.

Tumor volume ($mm^3$)=0.5×Major axis (mm)×[Minor axis (mm)]$^2$

From the viewpoint of animal testing ethics, individuals whose tumor volume exceeded 3000 $mm^3$ were euthanized.

The antibody-drug conjugate (1) was intravenously administered to the tail vein of each mouse at a dose of 10 mg/kg. CT26.WT-hHER2 cells were suspended in physiological saline, and $5.0 \times 10^6$ cells were subcutaneously transplanted to the right axilla of each BALB/c-nu mouse, and the mice were randomly grouped 3 days thereafter (Day 0). The antibody-drug conjugate (1) was intravenously administered to the tail vein of each mouse at a dose of 10 mg/kg on Days 0 and 7, twice in total. A group with administration of the solvent for the antibody-drug conjugate (1) was established as a control group. The number of mice in each group was 12, and tumor volumes were measured until Day 13.

The results are shown in FIG. 18. The ordinate depicts tumor volumes ($mm^3$) and the abscissa depicts days from the day of initial administration. The antitumor effect by administration of the antibody-drug conjugate (1), which had been found for BALB/c mice, was not found for the BALB/c-nu mice. From the finding that the number of T cells and that of B cells were reduced and the functions were impaired in the BALB/c-nu mice, it was inferred that these cells play an important role for the antitumor effect of the antibody-drug conjugate (1).

Evaluation Example 10: Antitumor Test

In the same manner as in Evaluation Example 1, transition of tumor volume in mice with subcutaneously transplanted CT26.WT-hHER2 cells was determined for an antibody-drug conjugate (1)-administered group, a control antibody-drug conjugate-administered group, and a control group.

The control antibody-drug conjugate (Drug-to-Antibody Ratio: 7.8), using a human IgG1 antibody which binds to molecules other than those derived from mice and humans, was diluted with special solvent for use. Grouping was performed 5 days after the transplantation (Day 0). The control antibody-drug conjugate or antibody-drug conjugate (1) was intravenously administered to the tail vein of each mouse at a dose of 10 mg/kg on Days 0 and 7, twice in total. The number of mice in each group was 10, and tumor volumes were measured until Day 10. Comparison on pharmaceutical effect between the control antibody-drug conjugate group and the antibody-drug conjugate (1) group was performed by using the Wilcoxon rank sum test, P values were expressed as numerical values to the fourth decimal place, and values of P<0.05 (two-tailed test) were regarded as significant differences.

The results are shown in FIG. 19. The ordinate depicts tumor volumes ($mm^3$) and the abscissa depicts days from the day of initial administration. On Day 10, the antibody-drug conjugate (1) group exhibited a significantly superior antitumor effect to the control antibody-drug conjugate group (P=0.0003). From the result, the antitumor effect of the antibody-drug conjugate (1) was found to be target-dependent.

Evaluation Example 11: Antitumor Test

In the same manner as in Evaluation Example 1, transition of tumor volume in mice with subcutaneously transplanted EMT6-hHER2 cells was determined for single administration groups with each of the antibody-drug conjugate (1) and an anti-PD-1 antibody (clone RMP1-14), and a combined administration group. The EMT6-hHER2 cells were prepared through transfection of a human HER2 gene into the mouse breast cancer cell line EMT6 (CRL-2755) purchased from American Type Culture Collection by using a lentivirus vector. These cells were expressing human HER2 protein on their cell membranes. The EMT6-hHER2 cells were suspended in physiological saline, and $1.0 \times 10^6$ cells were subcutaneously transplanted to the right axilla of each 5-week-old BALB/c mouse, and the mice were randomly grouped 4 days after the transplantation (Day 0). The antibody-drug conjugate (1) was intravenously administered to the tail vein of each mouse at a dose of 10 mg/kg once on Day 0. An anti-PD-1 antibody (clone RMP1-14) was prepared with D-PBS(-) (WAKO), and intravenously administered to the tail vein of each mouse at a dose of 5.0 mg/kg on Days 0, 3, 7, and 10, four times in total. A combined administration group with the antibody-drug conjugate (1) and the anti-PD-1 antibody was established, and a group with administration of the special solvent for the antibody-drug conjugate (1) was established as a control group. The number of mice in each group was 11, and tumor volumes were measured until Day 17. Comparison on pharmaceutical effect between the control group and each of the antibody-drug conjugate (1) group and the anti-PD-1 antibody group, and comparison on pharmaceutical effect between each of the antibody-drug conjugate (1) group and the anti-PD-1 antibody group and the combined administration group with both agents were performed by using Dunnett's test (comparison among multiple groups). P values adjusted for multiplicity were expressed as numerical values to the fourth decimal place, and values of P<0.05 (two-tailed test) were regarded as significant differences.

The results are shown in FIG. 20. The ordinate depicts tumor volumes ($mm^3$) and the abscissa depicts days from the day of initial administration. On Day 17, the antibody-drug conjugate (1) group exhibited a significantly superior antitumor effect to the control group (P<0.0001). The anti-PD-1 antibody group exhibited a significantly superior antitumor effect to the control group (P<0.0001). Further, the combined administration group exhibited a significantly superior antitumor effect to the antibody-drug conjugate (1) group (P=0.0136). The combined administration group exhibited a significantly superior antitumor effect to the anti-PD-1 antibody group (P=0.0372). Weight loss was observed for none of the mice in all of the groups in this test. From the results, the antitumor effect of single administration of each agent was confirmed, and it was further confirmed that such effect is dramatically enhanced through use of the two agents in combination.

Evaluation Example 12: Life Prolongation Test

In the same manner as in Evaluation Example 1, life-prolonging effects on mice with subcutaneously transplanted CT26.WT-hHER2 cells were determined for single administration groups with each of the antibody-drug conjugate (1) and an anti-PD-L1 antibody, and a combined administration group. An anti-PD-L1 antibody (clone 10F.9G2) was purchased from Bio X Cell, and diluted with InVivoPure pH 6.5 Dilution Buffer (Bio X Cell) for use. The mice were randomly grouped 6 days after the transplantation (Day 0), and the antibody-drug conjugate (1) was intravenously administered to the tail vein of each mouse at a dose of 10 mg/kg on Days 0 and 7, twice in total. The anti-PD-L1 antibody was intravenously administered to the tail vein of each mouse at a dose of 5 mg/kg on Days 0 and 3, twice in total. A combined administration group with the antibody-drug conjugate (1) and the anti-PD-L1 antibody was established, and a group with administration of the special solvent for the antibody-drug conjugate (1) was established as a control group. The number of mice in each group was 15, and tumor volumes were measured until Day 38. The day when estimated tumor volume exceeded 3000 $mm^3$ (day of euthanasia) was defined as the day of event occurrence (day of death), and comparison on survival time between the control group and each of the antibody-drug conjugate (1) group and the anti-PD-L1 antibody group, and comparison on survival time between each of the antibody-drug conjugate (1) group and the anti-PD-L1 antibody group and the combined administration group with both agents were performed by using the Kaplan-Meier method/logrank test (comparison among multiple groups). P values adjusted for multiplicity were expressed as numerical values to the fourth decimal place, and values of P<0.05 (two-tailed test) were regarded as significant differences.

The results are shown in FIG. 21. The antibody-drug conjugate (1) group exhibited a significantly superior antitumor effect to the control group (P=0.0069). The anti-PD-L1 antibody group exhibited a significantly superior antitumor effect to the control group (P=0.0037). Further, the combined administration group exhibited a significantly superior antitumor effect to the antibody-drug conjugate (1) group (P=0.0059). The combined administration group exhibited a significantly superior antitumor effect to the anti-PD-L1 antibody group (P=0.0091). Weight loss was observed for none of the mice in all of the groups in this test. From the results, the antitumor effect of single administration of each agent was confirmed, and it was further confirmed that such effect is dramatically enhanced through use of the two agents in combination.

Evaluation Example 13: Life Prolongation Test

EMT6-hHER2 cells were subcutaneously transplanted to mice in the same manner as in Evaluation Example 11, and life-prolonging effects were determined for single administration groups with each of the antibody-drug conjugate (1) and an anti-PD-L1 antibody, and a combined administration group in the same manner as in Evaluation Example 12. The mice were randomly grouped 5 days after the transplantation (Day 0), and the antibody-drug conjugate (1) was intravenously administered to the tail vein of each mouse at a dose of 10 mg/kg once on Day 0. The anti-PD-L1 antibody was intravenously administered to the tail vein of each mouse at a dose of 5 mg/kg on Days 0 and 3, twice in total. A combined administration group with the antibody-drug conjugate (1) and the anti-PD-L1 antibody was established, and a group with administration of the special solvent for the antibody-drug conjugate (1) was established as a control group. The number of mice in each group was six, and tumor volumes were measured until Day 60. Comparison on survival time between the control group and each of the antibody-drug conjugate (1) group and the anti-PD-L1 antibody group, and comparison on survival time between each of the antibody-drug conjugate (1) group and the anti-PD-L1 antibody group and the combined administration group with both agents were performed by using the Kaplan-Meier method/logrank test (comparison among multiple groups). P values adjusted for multiplicity were expressed as numerical values to the fourth decimal place, and values of P<0.05 (two-tailed test) were regarded as significant differences.

The results are shown in FIG. 22. The antibody-drug conjugate (1) group exhibited a significantly superior antitumor effect to the control group (P=0.0006). The anti-PD-L1 antibody group exhibited a significantly superior antitumor effect to the control group (P=0.0227). Further, the combined administration group exhibited a significantly superior antitumor effect to the antibody-drug conjugate (1) group (P=0.0039). Weight loss was observed for none of the mice in all of the groups in this test. From the results, the antitumor effect of single administration of each agent was confirmed, and it was further confirmed that such effect is dramatically enhanced through use of the two agents in combination.

Evaluation Example 14: In Vivo CD4/8 Depletion Test

In the same manner as in Evaluation Example 1, transition of tumor volume in mice with subcutaneously transplanted CT26.WT-hHER2 cells was determined for single administration groups with each of the antibody-drug conjugate (1) and an anti-CD4 antibody, and a combined administration group, and for single administration groups with each of the antibody-drug conjugate (1) and an anti-CD8 antibody, and a combined administration group. The antibody-drug conjugate (1) was prepared to reach 10 mg/kg, and the anti-CD4 antibody (Bio X Cell, clone GK1.5) and anti-CD8 antibody (Bio X Cell, clone 53.6.7), each of which is a depletion antibody, were each prepared to reach 1 mg/mL with D-PBS (−) immediately before administration, and each of them was intravenously administered to the tail vein of each mouse at a dose of 200 µg/head on Days 0 and 7. A group with administration of the special solvent for the antibody-drug conjugate (1) was established as a control group. Grouping was performed 5 days after the transplantation (Day 0), tumor volumes were measured until Day 11.

The results are shown in FIGS. 23 and 24. The tumor volume on Day 11 was 651 mm$^3$ for the antibody-drug conjugate (1) group, and 561 mm$^3$ for the combined administration group with the antibody-drug conjugate (1) and the anti-CD4 antibody, suggesting that CD4-positive cells do not contribute to the antitumor effect of the antibody-drug conjugate (1) (FIG. 23). The tumor volume on Day 11 was 651 mm$^3$ for the antibody-drug conjugate (1) group, and 2247 mm$^3$ for the combined administration group with the antibody-drug conjugate (1) and the anti-CD8 antibody, suggesting that CD8-positive cells contribute to the antitumor effect of the antibody-drug conjugate (1) (FIG. 24). Tumor volume had exceeded 3000 mm$^3$ in some individuals in the anti-CD4 antibody group and the anti-CD8 antibody group, and hence the individuals were euthanized during the test. Thus, each of the tumor growth curves ends at the timing of euthanasia. In combination with the finding from the tumor model using immunodeficient nude mice in Evaluation Example 9 that T cells or B cells are partly involved in the pharmaceutical effect of the antibody-drug conjugate (1), the present results suggested that CD8-positive T cells contribute to the antitumor effect of the antibody-drug conjugate (1).

Evaluation Example 15: Analysis of Intratumor T Cells

The fraction of CD8-positive T cells among intratumor living cells, the fraction of Granzyme B-positive cells among intratumor CD8-positive T cells, the fraction of CD8-positive T cells being Granzyme B-positive among intratumor living cells, and the fraction of CD4-positive T cells among intratumor living cells were determined with flow cytometry for the case that the antibody-drug conjugate (1) was administered to mice with subcutaneously transplanted CT26.WT-hHER2 cells. Cell suspensions were prepared in the same manner as in Evaluation Example 6, and then staining was performed with a Pacific Blue labeled anti-mouse CD45 antibody (103126, BioLegend), PE labeled anti-mouse CD3e antibody (553064, Becton Dickinson), PerCP/Cy5.5 labeled anti-mouse CD4 antibody (100434, BioLegend), PE-Cy 7 labeled anti-mouse CD8a antibody (552877, Becton Dickinson), and Alexa FluorR 647 labeled anti-human/mouse Granzyme B antibody (515405, BioLegend), and assayed with flow cytometry. Dead cells had been stained with a LIVE/DEAD Fixable Near-IR Dead Cell Stain Kit purchased from Thermo Fisher Scientific, and excluded from the analysis. Comparison between the control group and the antibody-drug conjugate (1) group was performed by using Student's t-test, P values were expressed as numerical values to the fourth decimal place, and values of P<0.05 (two-tailed test) were regarded as significant differences.

The results are shown in FIGS. 25 to 28. It was found that the fraction of CD45-, CD3-, CD8-positive cells (CD8-positive T cells) among living cells significantly increased by administration of the antibody-drug conjugate (1) (FIG. 25). It was found that the fraction of Granzyme B-positive cells among CD8-positive T cells significantly increased by administration of the antibody-drug conjugate (1) (FIG. 26). It was found that the fraction of CD8-positive T cells being Granzyme B-positive among living cells significantly increased by administration of the antibody-drug conjugate (1) (FIG. 27). Although the fraction of CD45-, CD3-, CD4-positive cells (CD4-positive T cells) among living cells had an increasing tendency by administration of the antibody-drug conjugate (1), the difference was not significant (FIG. 28).

Thus, these results suggested that the antibody-drug conjugate (1) activates antitumor immunity by increasing the number of intratumor CD8-positive T cells and promoting activation thereof.

Evaluation Example 16: CD8 IHC Analysis

The number of CD8-positive cells per unit area in tumors was counted by using IHC for the case that the antibody-drug conjugate (1) was administered to mice with subcutaneously transplanted CT26.WT-hHER2 cells. In the same manner as in Evaluation Example 6, the control and the antibody-drug conjugate (1) were administered, and the mice were euthanized 8 days after the administration. The number of mice in each group was five, and tumors were excised from the intermediate number of mice, namely, three mice, and each soaked in paraformaldehyde/phosphate buffer to produce a paraffin block. Each paraffin block was stained with an anti-CD8 antibody (clone: 4SM16), and the sample image was taken by using a NanoZoomer 2.0-HT (Hamamatsu Photonics K.K.), and the whole region of tissue was analyzed by using the image analysis software Tissue Studio3.0 (Definiens).

The results are shown in FIGS. 29 and 30. It was found that the number of CD8-positive cells per unit area in tumors tended to increase by the action of the antibody-drug conjugate (1).

Evaluation Example 17: Analysis of In Vitro Cancer Cells

Expression levels of MHC class I were determined for cancer cells treated with different compounds. In the same manner as in Evaluation Example 8, each of the compound (A), DM1-SMe, DM4-SMe (J. Med. Chem. (2014), 57, 16, 6949-6964), and MMAE (Molecular Cancer Therapeutics (2011), 10, 9, 1728-1739) was added to a concentration of 20 nM, 100 nM, or 500 nM, and the expression level of MHC class I on cancer cells was determined with flow cytometry. The experiment was performed in triplicate. Comparison between the control group and each of the agent groups at each concentration was performed by using Dunnett's test, P values were expressed as numerical values to the fourth decimal place, and values of P<0.05 (two-tailed test) were regarded as significant differences (*: P<0.001, : P<0.01).

The results are shown in FIG. 31. At the concentrations examined (20 nM, 100 nM, 500 nM), all of the agents evaluated were found to significantly elevate the expression level of MHC class I on CT26.WT-hHER2 cells as compared with the control group. Among them, the compound (A) was found to exhibit the maximum elevation effect on expression of MHC class I on CT26.WT-hHER2 cells.

Evaluation Example 18: Antitumor Test

In the same manner as in Evaluation Example 11, transition of tumor volume in mice with subcutaneously transplanted EMT6-hHER2 cells was determined for single administration groups with each of the antibody-drug conjugate (1) and an anti-CTLA-4 antibody, and a combined administration group. An anti-CTLA-4 antibody (clone 9H10) was purchased from Bio X Cell, and diluted with D-PBS(−) for use. Grouping was performed 5 days after the transplantation (Day 0). The antibody-drug conjugate (1) was intravenously administered to the tail vein of each mouse at a dose of 10 mg/kg once on Day 0. The anti-CTLA-4 antibody was intravenously administered to the tail vein of each mouse at a dose of 5.0 mg/kg on Days 0, 3, and 7, three times in total. A combined administration group with the antibody-drug conjugate (1) and the anti-CTLA-4 antibody was established, and a group with administration of the special solvent for the antibody-drug conjugate (1) was established as a control group. The number of mice in each group was 10, and tumor volumes were measured until Day 14. Comparison on pharmaceutical effect between the control group and each of the antibody-drug conjugate (1) group and the anti-CTLA-4 antibody group, and comparison on pharmaceutical effect between each of the antibody-drug conjugate (1) and the anti-CTLA-4 antibody group and the combined administration group with both agents were performed by using Dunnett's test (comparison among multiple groups). P values adjusted for multiplicity were expressed as numerical values to the fourth decimal place, and values of P<0.05 (two-tailed test) were regarded as significant differences.

The results are shown in FIG. 32. The ordinate depicts tumor volumes ($mm^3$) and the abscissa depicts days from the day of initial administration. On Day 14, the antibody-drug conjugate (1) group exhibited a significantly superior antitumor effect to the control group (P=0.0011). The anti-CTLA-4 antibody group exhibited a significantly superior antitumor effect to the control group (P=0.0006). Further, the combined administration group exhibited a significantly superior antitumor effect to the antibody-drug conjugate (1) group (P=0.0115). The combined administration group exhibited a significantly superior antitumor effect to the anti-CTLA-4 antibody group (P=0.0309). From the results, the antitumor effect of single administration of each agent was confirmed, and it was further confirmed that such effect is dramatically enhanced through use of the two agents in combination.

From the above experimental results, the antibody-drug conjugate according to the present invention was revealed to exhibit a dramatically excellent antitumor effect through being administered in combination with an immune checkpoint inhibitor. In addition, the antibody-drug conjugate according to the present invention was demonstrated to have an antitumor immunity-activating effect. Accordingly, the antibody-drug conjugate can provide a pharmaceutical composition and therapeutic method superior in antitumor effect and safety.

Free Text of Sequence Listing
SEQ ID NO: 1—Amino acid sequence of a heavy chain of the humanized anti-HER2 antibody
SEQ ID NO: 2—Amino acid sequence of a light chain of the humanized anti-HER2 antibody

The invention claimed is:

1. A therapeutic method wherein an antibody-drug conjugate and an immune checkpoint inhibitor are administered in combination to a subject in need thereof, and the antibody-drug conjugate is an antibody-drug conjugate in which a drug-linker represented by the following formula:

[Formula 4]

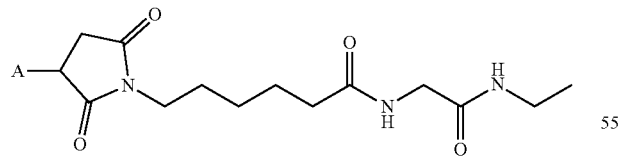

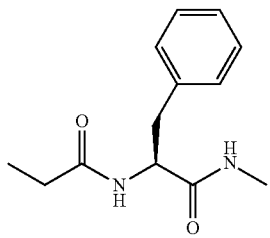

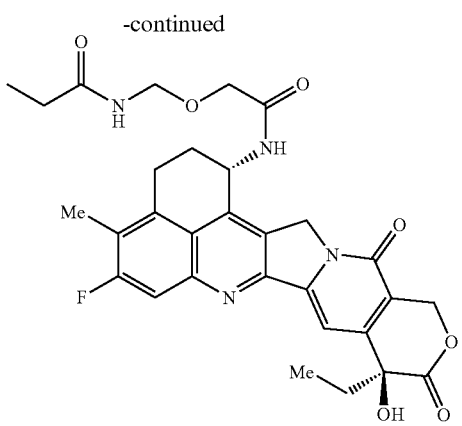

wherein A represents the connecting position to an antibody, is conjugated to the antibody via a thioether bond.

2. The therapeutic method according to claim 1, wherein the antibody in the antibody-drug conjugate is an anti-HER2 antibody, an anti-HER3 antibody, an anti-TROP2 antibody, or an anti-B7-H3 antibody.

3. The therapeutic method according to claim 2, wherein the antibody in the antibody-drug conjugate is an anti-HER2 antibody.

4. The therapeutic method according to claim 2, wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

5. The therapeutic method according to claim 2, wherein the anti-HER2 antibody is an antibody comprising a heavy chain consisting of the amino acid sequence represented by SEQ ID NO: 1 and a light chain consisting of the amino acid sequence represented by SEQ ID NO: 2.

6. The therapeutic method according to claim 1, wherein the average number of units of the drug-linker conjugated per antibody molecule in the antibody-drug conjugate is in the range of from 2 to 8.

7. The therapeutic method according to claim 1, wherein the average number of units of the drug-linker conjugated per antibody molecule in the antibody-drug conjugate is in the range of from 7 to 8.

8. The therapeutic method according to claim 1, wherein the average number of units of the drug-linker conjugated per antibody molecule in the antibody-drug conjugate is in the range of from 7.5 to 8.

9. The therapeutic method according to claim 1, wherein the immune checkpoint inhibitor is an anti-PD-1 antibody, an anti-PD-L1 antibody, or an anti-CTLA-4 antibody.

10. The therapeutic method according to claim 9, wherein the immune checkpoint inhibitor is an anti-PD-1 antibody.

11. The therapeutic method according to claim 9, wherein the immune checkpoint inhibitor is an anti-PD-L1 antibody.

12. The therapeutic method according to claim 9, wherein the immune checkpoint inhibitor is an anti-CTLA-4 antibody.

13. The therapeutic method according to claim 1, wherein the antibody-drug conjugate and the immune checkpoint inhibitor are separately contained as active components in different formulations, and are administered simultaneously or at different times.

14. The therapeutic method according to claim 1, wherein the antibody-drug conjugate and the immune checkpoint inhibitor are contained as active components in a single formulation and administered.

15. The therapeutic method according to claim 1, wherein the method is for treating cancer.

16. The therapeutic method according to claim 15, wherein the cancer is at least one selected from the group consisting of lung cancer, urothelial cancer, colorectal cancer, prostate cancer, ovarian cancer, pancreatic cancer, breast cancer, bladder cancer, gastric cancer, esophagogastric junction adenocarcinoma, gastrointestinal stromal tumor, uterine cervix cancer, esophageal cancer, squamous cell carcinoma, peritoneal cancer, liver cancer, hepatocellular cancer, endometrial cancer, uterine cancer, salivary gland cancer, kidney cancer, vulval cancer, thyroid cancer, penis cancer, leukemia, malignant lymphoma, plasmacytoma, myeloma, neuroepithelial tissue tumor, nerve sheath tumor, head-and-neck cancer, skin cancer, pharyngeal cancer, gallbladder cancer, bile duct cancer, mesothelioma, Paget's disease, and sarcoma.

17. The therapeutic method according to claim 16, wherein the cancer is colorectal cancer.

18. The therapeutic method according to claim 16, wherein the cancer is breast cancer.

19. The therapeutic method according to claim 1, wherein the antibody-drug conjugate has an antitumor immunity-activating effect.

20. The therapeutic method according to claim 1, wherein the antibody-drug conjugate has at least one effect selected from the group consisting of:
(1) a promoting effect on growth of intratumor CD8-positive T cells; and
(2) an activating effect on intratumor CD8-positive T cells.

21. The therapeutic method according to claim 1, wherein the antibody-drug conjugate has a promoting effect on the formation of immune memory against tumor.

22. The therapeutic method according to claim 21, wherein the tumor is expressing an antigen for the antibody in the antibody-drug conjugate.

23. The therapeutic method according to claim 21, wherein a part of the cells of the tumor are not expressing an antigen for the antibody in the antibody-drug conjugate.

24. The therapeutic method according to claim 1, wherein the antibody-drug conjugate has at least one effect selected from the group consisting of:
(1) a promoting effect on increase of the number of dendritic cells in a tumor;
(2) an activating effect on dendritic cells; and
(3) a promoting effect on elevation of the expression level of WIC class I on cancer cells.

25. The therapeutic method according to claim 1, wherein the immune checkpoint inhibitor deactivates an immunosuppression signal generated through elevation of the expression level of PD-L1 on cancer cells promoted by the antibody-drug conjugate, and thereby the antibody-drug conjugate exhibits a higher antitumor effect.

* * * * *